United States Patent
Denison et al.

(10) Patent No.: US 9,197,173 B2
(45) Date of Patent: *Nov. 24, 2015

(54) CHOPPER-STABILIZED INSTRUMENTATION AMPLIFIER FOR IMPEDANCE MEASUREMENT

(75) Inventors: Timothy J. Denison, Minneapolis, MN (US); Wesley A. Santa, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 496 days.

This patent is subject to a terminal disclaimer.

(21) Appl. No.: 12/579,276

(22) Filed: Oct. 14, 2009

(65) Prior Publication Data

US 2010/0033240 A1 Feb. 11, 2010

Related U.S. Application Data

(63) Continuation of application No. 12/058,066, filed on Mar. 28, 2008, now Pat. No. 7,622,988, which is a continuation of application No. 11/700,405, filed on Jan. 31, 2007, now Pat. No. 7,391,257.

(51) Int. Cl.
*H03F 1/02* (2006.01)
*H03F 3/387* (2006.01)
(Continued)

(52) U.S. Cl.
CPC .............. *H03F 3/387* (2013.01); *A61B 5/0002* (2013.01); *A61B 5/04004* (2013.01);
(Continued)

(58) Field of Classification Search
CPC ..................................... H03F 1/02; H03F 3/00
USPC ........................... 330/9, 10, 69; 327/124, 707
See application file for complete search history.

(56) References Cited

U.S. PATENT DOCUMENTS

| 1,342,885 A | 6/1920 | Armstrong |
| 3,130,373 A | 4/1964 | Braymer |

(Continued)

FOREIGN PATENT DOCUMENTS

| EP | 0 354 060 | 2/1990 |
| EP | 0568197 A2 | 3/1993 |

(Continued)

OTHER PUBLICATIONS

Harrison et al., "Local Field Potential Measurement with Low-Power Analog Integrated Circuit," Engineering in Medicine and Biology Society, 2004, IEMBS '04, 26th Annual International Conference of the IEEE, vol. 2, on pp. 4067-4070 vol. 6, Sep. 1-5, 2004.

(Continued)

*Primary Examiner* — Henry Choe
(74) *Attorney, Agent, or Firm* — Shumaker & Sieffert, P.A.

(57) ABSTRACT

This disclosure describes a chopper stabilized instrumentation amplifier. The amplifier is configured to achieve stable measurements at low frequency with very low power consumption. The instrumentation amplifier uses a differential architecture and a mixer amplifier to substantially eliminate noise and offset from an output signal produced by the amplifier. Dynamic limitations, i.e., glitching, that result from chopper stabilization at low power are substantially eliminated through a combination of chopping at low impedance nodes within the mixer amplifier and feedback. The signal path of the amplifier operates as a continuous time system, providing minimal aliasing of noise or external signals entering the signal pathway at the chop frequency or its harmonics. The amplifier can be used in a low power system, such as an implantable medical device, to provide a stable, low-noise output signal.

24 Claims, 17 Drawing Sheets

(51) Int. Cl.

| | |
|---|---|
| *A61B 5/00* | (2006.01) |
| *A61B 5/04* | (2006.01) |
| *A61B 5/0428* | (2006.01) |
| *A61B 5/053* | (2006.01) |
| *A61N 1/37* | (2006.01) |
| *H03F 1/26* | (2006.01) |
| *H03F 3/45* | (2006.01) |
| *A61B 5/103* | (2006.01) |
| *A61N 1/365* | (2006.01) |
| *A61N 1/08* | (2006.01) |

(52) U.S. Cl.
CPC ............ *A61B 5/0428* (2013.01); *A61B 5/053* (2013.01); *A61B 5/7203* (2013.01); *A61B 5/7217* (2013.01); *A61B 5/7228* (2013.01); *A61N 1/3702* (2013.01); *H03F 1/26* (2013.01); *H03F 3/45183* (2013.01); *H03F 3/45192* (2013.01); *H03F 3/45475* (2013.01); *H03F 3/45744* (2013.01); *H03F 3/45968* (2013.01); *A61B 5/103* (2013.01); *A61B 2560/0209* (2013.01); *A61N 1/36521* (2013.01); *A61N 1/3704* (2013.01); *A61N 2001/083* (2013.01); *H03F 2200/153* (2013.01); *H03F 2200/252* (2013.01); *H03F 2200/261* (2013.01); *H03F 2200/271* (2013.01); *H03F 2200/372* (2013.01); *H03F 2200/375* (2013.01); *H03F 2203/45028* (2013.01); *H03F 2203/45138* (2013.01); *H03F 2203/45212* (2013.01); *H03F 2203/45264* (2013.01); *H03F 2203/45396* (2013.01); *H03F 2203/45512* (2013.01); *H03F 2203/45534* (2013.01); *H03F 2203/45551* (2013.01)

(56) References Cited

U.S. PATENT DOCUMENTS

| | | | |
|---|---|---|---|
| 3,603,997 A | 9/1971 | Brouwer | |
| 3,735,274 A * | 5/1973 | Nelson | 330/1 A |
| 3,780,725 A | 12/1973 | Goldberg | |
| 4,138,649 A | 2/1979 | Schaffer | |
| 4,177,819 A | 12/1979 | Kofsky et al. | |
| 4,188,586 A | 2/1980 | Egami | |
| 4,279,258 A | 7/1981 | John | |
| 4,579,125 A | 4/1986 | Strobl et al. | |
| 4,610,259 A | 9/1986 | Cohen et al. | |
| 4,612,934 A | 9/1986 | Borkan | |
| 4,733,667 A | 3/1988 | Olive et al. | |
| 4,810,960 A | 3/1989 | Owen et al. | |
| 4,933,642 A | 6/1990 | Lee | |
| 4,979,230 A | 12/1990 | Marz | |
| 5,024,221 A | 6/1991 | Morgan | |
| 5,061,593 A | 10/1991 | Yoerger et al. | |
| 5,105,167 A | 4/1992 | Peczalski | |
| 5,113,143 A | 5/1992 | Wei | |
| 5,179,947 A | 1/1993 | Meyerson et al. | |
| 5,206,602 A | 4/1993 | Baumgartner et al. | |
| 5,282,840 A | 2/1994 | Hudrlik | |
| 5,311,876 A | 5/1994 | Olsen et al. | |
| 5,334,222 A | 8/1994 | Salo et al. | |
| 5,458,117 A | 10/1995 | Chamoun et al. | |
| 5,477,481 A | 12/1995 | Kerth | |
| 5,619,536 A | 4/1997 | Gourgue | |
| 5,663,680 A | 9/1997 | Nordeng | |
| 5,725,558 A | 3/1998 | Warnke | |
| 5,777,235 A | 7/1998 | Altwein | |
| 5,782,884 A | 7/1998 | Stotts et al. | |
| 5,843,139 A | 12/1998 | Goedeke et al. | |
| 5,928,272 A | 7/1999 | Adkins et al. | |
| 6,011,990 A | 1/2000 | Schultz et al. | |
| 6,016,444 A | 1/2000 | John | |
| 6,018,682 A | 1/2000 | Rise | |
| 6,061,593 A | 5/2000 | Fischell et al. | |
| 6,064,257 A | 5/2000 | Sauer | |
| 6,066,163 A | 5/2000 | John | |
| 6,070,101 A | 5/2000 | Struble et al. | |
| 6,129,681 A | 10/2000 | Kuroda et al. | |
| 6,130,578 A | 10/2000 | Tang | |
| 6,161,042 A | 12/2000 | Hartley et al. | |
| 6,262,626 B1 * | 7/2001 | Bakker et al. | 330/9 |
| 6,287,263 B1 | 9/2001 | Briskin | |
| 6,360,123 B1 | 3/2002 | Kimchi et al. | |
| 6,456,159 B1 * | 9/2002 | Brewer | 330/9 |
| 6,463,328 B1 | 10/2002 | John | |
| 6,483,355 B1 | 11/2002 | Lee et al. | |
| 6,522,914 B1 | 2/2003 | Huvelle et al. | |
| 6,539,261 B2 | 3/2003 | Dal Molin | |
| 6,584,351 B1 | 6/2003 | Ekwall | |
| 6,617,838 B1 | 9/2003 | Miranda et al. | |
| 6,621,334 B2 * | 9/2003 | Ausserlechner et al. | 330/9 |
| 6,625,436 B1 | 9/2003 | Tolson et al. | |
| 6,667,760 B1 | 12/2003 | Limberg | |
| 6,674,322 B2 * | 1/2004 | Motz | 330/9 |
| 6,725,091 B2 | 4/2004 | Dal Molin | |
| 6,753,731 B2 * | 6/2004 | Maki | 330/255 |
| 6,754,535 B2 | 6/2004 | Noren et al. | |
| 6,810,285 B2 | 10/2004 | Pless et al. | |
| 6,876,842 B2 | 4/2005 | Davie | |
| 6,904,321 B1 | 6/2005 | Bornzin et al. | |
| 6,914,539 B2 | 7/2005 | Hoctor et al. | |
| 6,993,380 B1 | 1/2006 | Modarres | |
| 7,006,872 B2 | 2/2006 | Gielen et al. | |
| 7,010,347 B2 | 3/2006 | Schecter | |
| 7,038,532 B1 | 5/2006 | Bocko et al. | |
| 7,098,823 B2 | 8/2006 | O'Dowd et al. | |
| 7,146,208 B2 | 12/2006 | Holmstrom et al. | |
| 7,146,218 B2 | 12/2006 | Esteller et al. | |
| 7,171,258 B2 | 1/2007 | Goode | |
| 7,177,609 B1 | 2/2007 | Wong | |
| 7,233,198 B2 * | 6/2007 | Niederkorn | 330/9 |
| 7,239,927 B2 | 7/2007 | Ganion | |
| 7,253,685 B2 * | 8/2007 | Chung | 330/255 |
| 7,295,061 B1 * | 11/2007 | Dasgupta | 330/9 |
| 7,336,123 B2 * | 2/2008 | Yoshida et al. | 330/9 |
| 7,376,463 B2 | 5/2008 | Salo et al. | |
| 7,385,443 B1 | 6/2008 | Denison | |
| 7,391,257 B1 | 6/2008 | Denison et al. | |
| 7,504,882 B2 * | 3/2009 | Saito | 330/253 |
| 7,595,648 B2 * | 9/2009 | Ungaretti et al. | 324/678 |
| 7,622,988 B2 | 11/2009 | Denison et al. | |
| 7,671,672 B2 | 3/2010 | McConnell | |
| 7,847,628 B2 | 12/2010 | Denison | |
| 8,139,015 B2 * | 3/2012 | Kawaguchi et al. | 345/100 |
| 2002/0091332 A1 | 7/2002 | Bombardini | |
| 2003/0146786 A1 | 8/2003 | Gulati et al. | |
| 2004/0002635 A1 | 1/2004 | Hargrove et al. | |
| 2004/0077967 A1 | 4/2004 | Jordan | |
| 2004/0141558 A1 | 7/2004 | Plisch et al. | |
| 2004/0158119 A1 | 8/2004 | Osorio et al. | |
| 2004/0167418 A1 | 8/2004 | Nguyen et al. | |
| 2005/0007091 A1 | 1/2005 | Makeig et al. | |
| 2005/0081847 A1 | 4/2005 | Lee et al. | |
| 2005/0118968 A1 | 6/2005 | Cowley | |
| 2005/0182447 A1 | 8/2005 | Schecter | |
| 2005/0282517 A1 | 12/2005 | Cowley | |
| 2006/0055456 A1 | 3/2006 | Niederkorn | |
| 2006/0116591 A1 | 6/2006 | Cooper | |
| 2006/0133550 A1 | 6/2006 | Bolton et al. | |
| 2006/0135877 A1 | 6/2006 | Giftakis et al. | |
| 2006/0139192 A1 | 6/2006 | Morrow et al. | |
| 2006/0139193 A1 | 6/2006 | Morrow et al. | |
| 2006/0173501 A1 | 8/2006 | Stickney et al. | |
| 2006/0184060 A1 | 8/2006 | Belalcazar et al. | |
| 2006/0241357 A1 | 10/2006 | Chirife | |
| 2006/0281427 A1 | 12/2006 | Isaac et al. | |
| 2006/0293720 A1 | 12/2006 | DiLorenzo | |
| 2007/0010755 A1 | 1/2007 | Sarkela et al. | |
| 2007/0032737 A1 | 2/2007 | Causevic et al. | |
| 2007/0077907 A1 | 4/2007 | Rector | |
| 2007/0216477 A1 | 9/2007 | McConnell | |
| 2007/0249953 A1 | 10/2007 | Frei et al. | |
| 2008/0015659 A1 | 1/2008 | Zhang et al. | |

(56) References Cited

U.S. PATENT DOCUMENTS

| | | | |
|---|---|---|---|
| 2008/0180278 | A1 | 7/2008 | Denison |
| 2008/0269630 | A1 | 10/2008 | Denison et al. |
| 2008/0269631 | A1 | 10/2008 | Denison et al. |
| 2008/0269841 | A1 | 10/2008 | Grevious et al. |
| 2009/0082691 | A1 | 3/2009 | Denison et al. |
| 2010/0033240 | A1 | 2/2010 | Denison et al. |
| 2010/0113964 | A1 | 5/2010 | Wahlstrand et al. |
| 2010/0114223 | A1 | 5/2010 | Wahlstrand et al. |
| 2010/0324442 | A1 | 12/2010 | Blomqvist |
| 2010/0327887 | A1 | 12/2010 | Denison et al. |
| 2011/0068861 | A1 | 3/2011 | Denison |

FOREIGN PATENT DOCUMENTS

| | | |
|---|---|---|
| EP | 0789449 A2 | 8/1997 |
| GB | 1 249 395 | 10/1971 |
| JP | 4717841 | 0/1972 |
| JP | 5615112 | 2/1981 |
| JP | 6224659 A | 8/1994 |
| JP | 7120207 A | 5/1995 |
| JP | 10504099 T | 4/1998 |
| JP | 2006279377 A | 10/2006 |
| WO | 9710747 A1 | 3/1997 |
| WO | WO 02/01711 | 1/2002 |
| WO | WO 02/03087 | 1/2002 |
| WO | WO 2006/066098 | 6/2006 |
| WO | 2006126186 A2 | 11/2006 |
| WO | 2008103078 A1 | 8/2008 |
| WO | 2008105692 A1 | 9/2008 |
| WO | 2009042172 A | 4/2009 |
| WO | 2009042313 A | 4/2009 |

OTHER PUBLICATIONS

Martins et al., "A CMOS IC for Portable EEG Acquisition Systems," IEEE Transactions on Instrumentation and Measurement, vol. 47, No. 5, pp. 1191-1196, Oct. 1998.
Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997.
Sanduleanu et al., "A Low Noise, Low Residual Offset, Chopped Amplifier for Mixed Level Applications," IEEE, 0-7803-5008-1/98, pp. 333-336, Sep. 1998.
Hadiashar et al., "A Chopper Stabilized CMOS Analog Multiplier with Ultra Low DC Offsets," Solid-State Circuits Conference, pp. 364-367, Sep. 2006.
Yazicioglu et al., "A 60uW 60nV/rtHz Readout Front-End for Portable Biopotential Acquisition Systems," ISSCC Digest of Technical Papers 2006, paper 2.6, Feb. 2006.
Makinwa, "Dynamic Offset Cancellation Techniques," Smart Sensor Systems '02, May 2002.
Ng et al., "A CMOS Analog Front-End IC for Portable EEG/ECG Monitoring Applications," IEEE Trans. On Circuits and Systems, vol. 52 No. 11, Nov. 2005.
Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006.
Harrison et al., "A Low-Power Low-Noise CMOS Amplifier for Neural Recording Applications," IEEE J. of Solid-State Circuits, vol. 38, No. 6, pp. 958-965, Jun. 2003.
Wu et al., "A 1V 2.3mW Biomedical Signal Acquisition IC," ISSCC Digest of Technical Papers 2006, paper 2.7, Feb. 2006.
Harrison et al., "A Low-Power Integrated Circuit for a Wireless 100-Electrode Neural Recording System," ISSCC Digest of Technical Papers 2006, paper 30.2, Feb. 2006.
Bakker et al., "A CMOS Nested-Chopper Instrumentation Amplifier with 100-nV Offset," IEEE Journal of Solid-State Circuits, vol. 35, No. 12, pp. 1877-1883, Dec. 2000.

Yiqian Ying, "Chopper Sabilized Amplifiers," Term Paper, Department of Electrical and Computer Engineering, University of Toronto, 17 pgs., Nov. 12, 2001.
Enz et al., "Circuit Techniques for Reducing the Effects of Opamp Imperfections," Proc. of the IEEE, vol. 84, No. 11, pp. 1584-1614, Nov. 1996.
Notification of Transmittal of the International Search Report and the Written Opinion dated Nov. 22, 2007 for corresponding PCT Application No. PCT/US2007/064788, (14 pgs.).
U.S. Appl. No. 11/609,388, filed Dec. 12, 2006, entitled "Method and Apparatus for Detection of Nervous System Disorders," by Carlson et al.
U.S. Appl. No. 11/700,738, filed Jan. 31, 2007, entitled "Chopper-Stabilized Instrumentation Amplifier for Wireless Telemetry," by Denison.
U.S. Appl. No. 11/700,404, filed Jan. 31, 2007, entitled "Chopper-Stabilized Instrumentation Amplifier for Impedance Measurement," by Denison et al.
U.S. Appl. No. 11/700,405, filed Jan. 31, 2007, entitled "Chopper-Stabilized Instrumentation Amplifier for Impedance Measurement," by Denison et al.
Notification of Transmittal of the International Preliminary Report on Patentability dated Feb. 19, 2009 for corresponding PCT Application No. PCT/US2007/064788, (16 pgs.).
Declaration Under 37 C.F.R. 1.132, 4 pgs., (signed by Michael W. Heinks on May 26, 2009).
Office Action dated Oct. 30, 2009 for U.S. Appl. No. 11/700,738 (13 pgs.).
Responsive Amendment dated Feb. 1, 2010 for U.S. Appl. No. 11/700,738 (19 pgs.).
Office Action dated Feb. 24, 2011 for U.S. Appl. No. 11/700,738, (9 pgs.).
Office Action dated Mar. 15, 2001 for U.S. Appl. No. 12/959,135, 4 pages.
Response dated Jun. 15, 2011 for U.S. Appl. No. 12/959,135, 3 pages.
Office Action dated Apr. 7, 2010 for U.S. Appl. No. 12/121,267 (4 pgs.).
Response dated Jul. 7, 2010 for U.S. Appl. No. 12/121,267 (4 pgs.).
Office Action dated May 13, 2010 for U.S. Appl. No. 11/700,738 (12 pgs.).
Response dated Sep. 13, 2010 for U.S. Appl. No. 11/700,738 (11 pgs.).
Heinks, "Declaration Under 37 C.F.R. 1.132," dated May 26, 2009, 4 pp.
Avestruz et al., "A 5 µW/Channel Spectral Analysis IC for Chronic Bidirectional Brain-Machine Interfaces," IEEE Journal of Solid-State Circuits, vol. 43, No. 12, Dec. 2008, 19 pp.
Denison et al., "A 2.2µW 94nV/$\sqrt{Hz}$, Chopper-Stabilized Instrumentation Amplifier for EEG Detection in Chronic Implants" JSSC, vol. 42, No. 12, Feb. 13, 2007, pp. 2934-2945.
Sarpeshkar, "Borrowing from biology makes for low-power computing," IEEE Spectrum, pp. 24-29, May 2006.
Denison et al., "An 8µW heterodyning chopper amplifier for direct extraction of 2µVrms Neuronal Biomarkers" ISSCC, paper 8.1, Feb. 5, 2008, 3 pp.
Andersen et al., "Recording Advances for Neural Prosthetics," in Engineering in Medicine and Biology Society, IEMBS 2004, 26th Annual International Conference of the IEEE, vol. 7, Sep. 1-5, 2004, pp. 5352-5355.
Andersen et al., "Selecting the signals for a brain-machine interface," Current Opinion in Neurobiology, vol. 14, 2004, pp. 720-726.
Denison et al., "A 2µW 100 nV/rtHz Chopper-Stabilized Instrumentation Amplifier for Chronic Measurement of Neural Field Potentials," Solid-state circuits, IEEE Journal, vol. 42, pp. 2934-2945, Dec. 2007.
Smart et al., "Automatic Detection of High Frequency Epileptiform Oscillations from Intracranial EEG Recordings of Patients with Neocortical Epilepsy," in Technical, Professional and Student Development Workshop, 2005 IEEE Region 5 and IEEE Denver Section, Apr. 7-8, 2005, pp. 53-58.
Krusienski et al., "A µ-Rhythm Matched Filter for Continuous Control of a Brain-Computer Interface," Biomedical Engineering, IEEE Transactions on, vol. 54, Feb. 2007, pp. 273-280.

(56) References Cited

OTHER PUBLICATIONS

Harrison et al., "A Low-Power Integrated Circuit for a Wireless 100—Electrode Neural Recording System," Solid state circuits. IEEE Journal of, vol. 42, Jan. 2007, pp. 123-133.
Haddad et al., "An ultra low-power dynamic translinear cardiac sense amplifier for pacemakers," Circuits and Systems, May 25-28, 2003, vol. 5, pp. V37-V40.
Haddad et al., "Analog wavelet transform employing dynamic translinear circuits for cardiac signal characterization," Circuits and Systems, May 2003, vol. 1, pp. 1-121-1-124.
Sarpeshkar et al., "An ultra-low-power programmable analog bionic ear processor," Biomedical Engineering, IEEE Transactions, vol. 52, Apr. 2005, pp. 711-727.
Sarpeshkar et al., "Low power circuits for brain—machine interfaces," IEEE Transactions on Biomedical Circuits and Systems, Sep. 2008, vol. 2, No. 3, pp. 173-183.
Yazicioglu et al., "A 200μW Eight-Channel Acquisition ASIC for Ambulatory EEG Systems," Solid-State Circuits Conference, Feb. 5, 2008, 3 pp.
Bakker et al., "A CMOS nested chopper instrumentation amplifier with 100nV offset," IEEE Journal of Solid-State Circuits, Digest of Technical Papers, IEEE International, Dec. 2000, vol. 35, No. 12, pp. 1877-1883.
Makinaw et al., "A CMOS Temperature-to-frequency converter with an Inaccuracy of less than ±0.5 °C. (3o) from -40 °C. to 105 °C.," IEEE Journal of Solid State Circuits, vol. 41, No. 12 , Dec. 2006, pp. 2992-2997.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, Jun. 18-20, 2008, pp. 76-77.
Kun et al., "Algorithm for Tissue Ischemia Estimation Based on Electrical Impedance Spectroscopy," IEEE Transactions on Biomedical Engineering, IEEE Service Center, vol. 50, No. 12, Dec. 2003, pp. 1352-1359.
Dzwonczyk et al., "Myocardial Electrical Impedance Responds to Ischemia and Reperfusion in Humans," IEEE Transactions on Biomedical Engineering, IEEE Service Center, vol. 51, No. 12, Dec. 2004, pp. 2206-2209.
Salthouse et al., "A practical micropower programmable bandpass filter for use in bionic ears," Solid-State Circuits, IEEE Journal, vol. 38, No. 1, Jan. 2003, pp. 63-70.
Wattanapanitch et al., "An energy-efficient micropower neural recording amplifier," Biomedical Circuits and Systems, IEEE Transactions, vol. 1, No. 2, Jun. 2007, pp. 136-147.
Min et al., "Electrical Impedance and Cardiac Monitoring—Technology, Potential and Applications," International Journal of Bioelectromagnetism, International Society for Bioelectromagnetism, vol. 5, No. 1, Jan 2003, pp. 53-56.
Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, Jan. 29-30, 2007, 15 pp.
Bakker, "High-Accuracy CMOS Smart Temperature Sensors," Thesis Delft University of Technology, Apr. 17, 2000, pp. 20, 21, 51 and 52.
Rajan et al., "Offset cancellation and 1/f noise suppression scheme for chopper amplifiers," IEEE, 2000, pp. 68-71.
Response to Office Action dated Feb. 24, 2011, from U.S. Appl. No. 11/700,738, filed Jun. 24, 2011, 14 pp.
Japanese Office Action from Japanese application No. 2009-548232, dated Apr. 20, 2011, 4 pp. (citing JP 56/5112 and JP 4717841).
Japanese Office Action from Japanese application No. 2009-548231, dated May 18, 2011, 11 pp. (citing JP 4717841).
Liu, "Operational amplifiers," in: Demystifying Switched Capacitor Circuits (Demystifying Technology, vol. 1), May 11, 2006, pp. 15-26.
Moualla et al., "Chopped Folded Cascode Bulk Driven OTA", Proceedings of the International Interdisciplinary Honeywell EMI 2005, May 26, 2005, pp. 185-189.
Abidi, "CMOS wireless transceivers: the new wave," IEEE Communications Magazine 37, 119-124 (1999).
Rauscher, "Practical Realization of an Analyzer Operating on the Heterodyne Principle," Chapter 4 (partial) of Fundamentals of Spectrum Analysis (Rohde & Schwarz, 2001). pp. 34-64. With 2 pages of front matter and 2 pages of diagrams.
Yates, "An ultra low power low noise chopper amplifier for wireless EEG". In 49th IEEE International Midwest Symposium on Circuits and Systems, 2006. MWSCAS '06., vol. 2, 449-452 (IEEE, 2006).
Response to Office Action dated Sep. 14, 2012, from U.S. Appl. No. 11/799,108, filed Dec. 14, 2012, 23 pp.
Office Action for U.S. Appl. No. 11/799,108, dated Sep. 14, 2012, 13 pp.
Office Action for U.S. Appl. No. 12/872,552, dated Jan. 15, 2013, 7 pp.
Office action from U.S. Appl. No. 12/872,552, dated Aug. 14, 2013, 4 pp.
Office Action from U.S. Appl. No. 12/872,552, dated May 14, 2014, 6 pp.
"baseband" entry, Academic Press Dictionary of Science and Technology, Oxford: Elsevier Science and Technology, 1992, 2 pp.
"baseband" entry and p. 86, Authoritative Dictionary of IEEE Standard Terms (Seventh Edition), New York: IEEE, 2000, 3 pp.
Rudell et al., "Recent developments in high integration multi standard CMOS transceivers for personal communication systems," Proceedings. 1998 International Symposium on Low Power Electronics and Design, The Association for Computing Machinery, Inc. (ACM), 1998, pp. 149-154, 6 pp.
Office Action from U.S. Appl. No. 12/872,552, dated May 10, 2013, 4 pp.
Office Action from U.S. Appl. No. 12/872,522, dated Dec. 19, 2013, 7 pp.
Response to Office Action dated Jan. 15, 2013, from U.S. Appl. No. 12/872,552, filed Apr. 15, 2013, 3 pp.
Notice of Allowance from U.S. Appl. No. 11/799,108, mailed Mar. 3, 2014, 5 pp.
Response to Office Action from U.S. Appl. No. 12/872,552, dated Dec. 19, 2013, filed Mar. 19, 2014, 7 pp.
Office Action from U.S. Appl. No. 12/872,552, dated Oct. 21, 2014, 4 pp.
Response to Office Action dated Oct. 21, 2014, from U.S. Appl. No. 12/872,552, dated Jan. 21, 2015, 15 pp.
Final Office Action from U.S. Appl. No. 12/872,552, dated Mar. 12, 2015, 6 pp.
Response to Office Action dated May 14, 2014, from U.S. Appl. No. 12/872,552, filed Jul. 14, 2014, 16 pp.
Office Action from U.S. Appl. No. 12/872,552, dated Jun. 24, 2015, 6 pp.

\* cited by examiner

CHOPPER-STABILIZED INSTRUMENTATION AMPLIFIER FOR IMPEDANCE MEASUREMENT

This application is a continuation of U.S. patent application Ser. No. 12/058,066, filed Mar. 28, 2008, which is a continuation of U.S. patent application Ser. No. 11/700,405, filed Jan. 31, 2007, now U.S. Pat. No. 7,391,257, the entire content of each of which is incorporated herein by reference.

TECHNICAL FIELD

The invention relates to amplifiers and, more particularly, to instrumentation amplifiers for accurate signal measurement.

BACKGROUND

Instrumentation amplifiers are used to accurately measure a variety of test and measurement signals. A medical instrumentation amplifier, for example, may be configured to measure physiological signals, such as electrocardiogram (ECG), electromyogram (EMG), electroencephalogram (EEG), pressure, impedance, and motion signals. Typically, instrumentation amplifiers are constructed as differential amplifiers exhibiting low offset, low drift, low noise, high common mode rejection, high loop gain, and high input impedance. In many cases, instrumentation amplifiers may require careful matching and trimming of circuit components to achieve a high degree of accuracy.

An instrumentation amplifier may be constructed with a discrete time switched capacitor architecture that obtains discrete signal samples. However, a discrete time architecture can produce undesirable aliasing of noise and signals, undermining the accuracy of measurement signals. Alternatively, an instrumentation amplifier may employ a chopper stabilized architecture in which a chopper circuit up-modulates a measurement signal into a higher frequency band to remove noise and offset. A chopper-stabilized architecture may have a limited bandwidth, however, producing a large ripple in the passband. The ripple may make implementation of chopper-stabilized designs difficult in low power applications.

SUMMARY

This disclosure describes a chopper stabilized instrumentation amplifier. The instrumentation amplifier is configured to achieve stable measurements at low frequency with very low power. The instrumentation amplifier uses a differential architecture and a mixer amplifier to substantially eliminate noise and offset from an output signal produced by the amplifier. Dynamic limitations, i.e., glitching, that result from chopper stabilization at low power are substantially eliminated or reduced through a combination of chopping at low impedance nodes within the mixer amplifier and feedback. The signal path of the instrumentation amplifier operates as a continuous time system, providing minimal aliasing of noise or external signals entering the signal pathway at the chop frequency or its harmonics. In this manner, the instrumentation amplifier can be used in a low power system, such as an implantable medical device, to provide a stable, low-noise output signal. The chopper stabilized instrumentation amplifier may be used for physiological signal sensing, impedance sensing, telemetry or other test and measurement applications.

In one embodiment, the invention provides a biomedical impedance sensing device comprising an alternating current (ac) source that generates an ac stimulation current at a clock frequency for application to a biological load, a mixer amplifier coupled to receive a differential input signal from the load in response to the stimulation current, wherein the mixer amplifier amplifies the differential input signal to produce an amplified signal and demodulates the amplified signal at the clock frequency to produce an output signal, a second modulator that modulates an amplitude of the output signal at the clock frequency, and a feedback path that applies the modulated output signal as a differential feedback signal to the differential input signal.

In another embodiment, the invention provides a method comprising generating an alternating current (ac) stimulation current at a clock frequency, applying the stimulation current to a load to produce a differential input signal, amplifying the differential input signal in a mixer amplifier to produce an amplified signal, demodulating the amplified signal in the mixer amplifier at the clock frequency to produce an output signal, modulating an amplitude of the output signal at the clock frequency to produce a differential feedback signal, and applying the modulated output signal as a differential feedback signal to the differential input signal via a first feedback path.

In an additional embodiment, the invention provides a chopper-stabilized instrumentation amplifier comprising an alternating current (ac) source that generates an ac stimulation current at a clock frequency for application to a load, a mixer amplifier coupled to receive a differential input signal from the load in response to the stimulation current, wherein the mixer amplifier amplifies the differential input signal to produce an amplified signal and demodulates the amplified signal at the clock frequency to produce an output signal, a second modulator that modulates an amplitude of the output signal at the clock frequency, and a feedback path that applies the modulated output signal as a differential feedback signal to the differential input signal.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
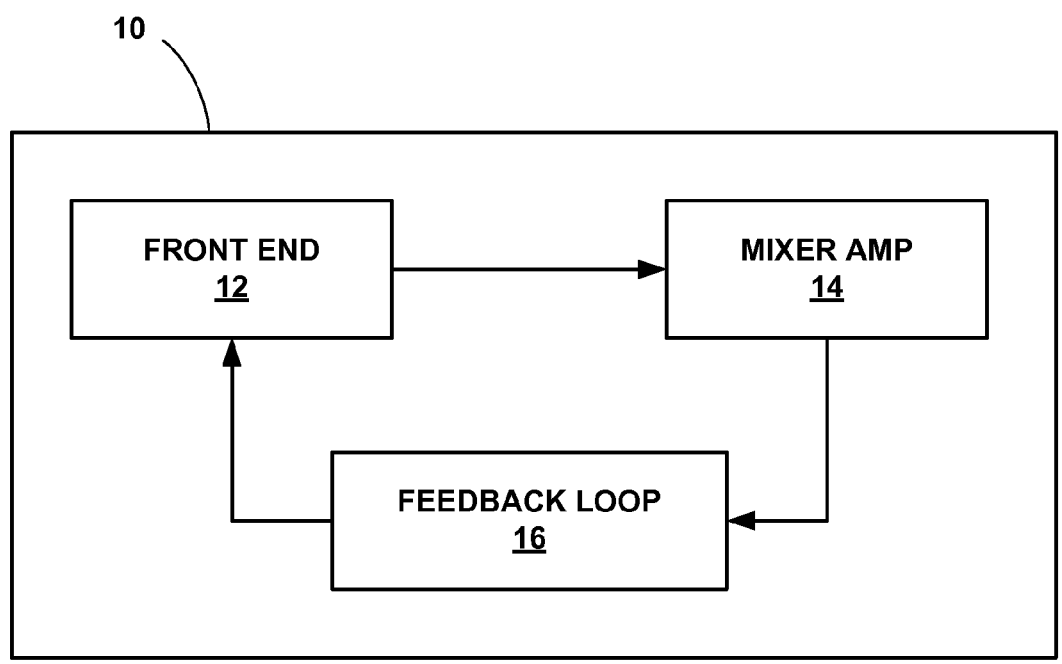
FIG. 1 is a block diagram illustrating a chopper-stabilized instrumentation amplifier configured to achieve stable measurement at low frequency with very low power.

This disclosure describes a chopper-stabilized instrumentation amplifier. The instrumentation amplifier is configured to achieve stable measurements at low frequency with very low power. The instrumentation amplifier uses a differential architecture and a mixer amplifier to substantially eliminate noise and offset from an output signal produced by the amplifier. Dynamic limitations, i.e., glitching, that result from chopper stabilization at low power are substantially eliminated through a combination of chopping at low impedance nodes within the mixer amplifier and feedback. The signal path of the instrumentation amplifier operates as a continuous time system, providing minimal aliasing of noise or external signals entering the signal pathway at the chop frequency or its harmonics. In this manner, the instrumentation amplifier can be used in a low power system, such as an implantable medical device, to provide a stable, low-noise output signal.

The chopper-stabilized instrumentation amplifier may be configured as a medical instrumentation amplifier, for example, to measure physiological signals, such as electrocardiogram (ECG), electromyogram (EMG), electroencephalogram (EEG), pressure, impedance, motion signals, and other signals. In some embodiments, the instrumentation amplifier may include a capacitor-based front end that is chopped to obtain low frequency voltage signals. In other embodiments, the instrumentation amplifier may include a current source-based front end that is chopped to obtain impedance measurements. In additional embodiments, the instrumentation amplifier may include an antenna-based front end to obtain telemetry signals from other devices. The instrumentation amplifier may be useful not only in biomedical measurement applications, but also in general purpose test and measurement applications and wireless telemetry applications.

In general, an instrumentation amplifier, as described in this disclosure, may be configured for very low power applications. An implantable medical device, for example, may be characterized by finite power resources that are required to last several months or years. Accordingly, to promote device longevity, sensing and therapy circuits are generally designed to consume very small levels of power. As an example, operation of a sensor circuit incorporating an instrumentation amplifier, as described in this disclosure, may require a supply current of less than 2.0 microamps, and more preferably less than 1.0 microamps. In some embodiments, such a sensor circuit may consume supply current in a range of approximately 100 nanoamps to 1.0 microamps. Such a sensor may generally be referred to as a micropower sensor. Although medical devices are described for purposes of illustration, a micropower sensor may be used in a variety of medical and non-medical test and measurement applications. In each case, a sensor may be required to draw very low power, yet provide precise and accurate measurement.

According to various embodiments of this disclosure, a chopper-stabilized instrumentation amplifier may include a front end, a first chopper, an AC amplifier, a second chopper, an integrator in the form of a baseband amplifier with high gain and compensation, and at least one feedback path. The amplifier, second chopper, and integrator may be referred to collectively as a mixer amplifier. The signal path of the instrumentation amplifier operates as a continuous time system, reducing aliasing of noise or other undesirable signals entering the signal pathway at the chop frequency or its harmonics. The front end generates a differential input signal in the baseband, i.e., the frequency band of interest for purposes of the test or measurement application. The baseband also may be referred to as the measurement band.

Amplification of the input signal can introduce DC offset and low frequency noise, such as 1/f or popcorn noise, due to amplifier imperfection or other factors. To reduce DC offset and low frequency noise, a first chopper stage in the front end modulates the input signal at a chopper frequency prior to application of the input signal to the mixer amplifier. After the input signal is amplified, the second chopper within the mixer amplifier demodulates the input signal at the chopper frequency to produce an amplified output signal in the baseband. This process confines the noise and offset generated by the amplifier to the chopper frequency band, thereby preventing it from entering the measurement band.

The mixer amplifier may have a modified folded cascode amplifier architecture in which the signal is chopped at low impedance nodes to provide fast modulation dynamics. The mixer amplifier substantially removes the noise and offset at the chopper frequency from the demodulated signal, and thereby passes a low noise signal to the measurement band. When the mixer amplifier is operating at low power, however, the bandwidth of the amplifier can be limited. Limited bandwidth can result in glitching, i.e., ripple or spikes, in the output signal. An instrumentation amplifier as described in this disclosure may provide negative feedback to keep the signal change at the input to the mixer amplifier relatively small. In addition, the feedback can be provided to both inputs of the mixer amplifier to provide differential-to-single conversion. As a result, an instrumentation amplifier can be configured to achieve a stable, low noise output while drawing very low current from a power source.

Additional feedback paths may be added to achieve increased performance. For example, a positive feedback path may used to increase input impedance of the instrumentation amplifier. As another example, another negative feedback path may allow for the construction of a high pass filter.

Each feedback path may be a differential feedback path. These additional feedback paths may not be necessary for the chopper stabilized amplifier to operate properly, but may enhance performance. For example, these feedback paths may be added to provide additional signal processing or conditioning that may be useful in various applications in which the instrumentation amplifier may be used.

Various example embodiments are presented. According to one example embodiment, which is useful when the instrumentation amplifier senses a difference in voltage across its inputs, the front end may include a continuous time switched capacitor network. The switched capacitor network includes a differential set of switched input capacitors that toggle between input voltages at a chop frequency. By chopping the switched input capacitors, the input differential signal is up-modulated to a chopper frequency, yielding a modulated signal at the differential input of the mixer amplifier. This embodiment may be useful as an instrumentation amplifier for electroencephalography (EEG) and physiological monitoring applications such as posture and activity monitoring with accelerometers, catheter monitoring with pressure sensors, other pressure-related physiological monitoring, monitoring of heart sounds, monitoring of brain signals, and other physiological monitoring applications that require micro power systems for precision sensor measurements.

According to another example embodiment, the instrumentation amplifier may be configured to measure impedances of physiologic importance, such as tissue impedance Measuring such impedances can be used to measure physiological conditions, such as pulmonary edema, minute ventilation respiration (e.g., for sleep apnea), cardiac dynamics, and general tissue impedance. It is important when measuring such impedances that the stimulation current be small, e.g., less than or equal to approximately 10 µA or less, to avoid stimulation of excitable cells, or cause other detrimental effects such as electrode corrosion. In this example embodiment, the front end produces an AC modulated signal that is AC coupled to the mixer amplifier through tissue of a patient. The front end modulates a stimulation current at the chopper frequency to modulate the amplitude of a tissue voltage signal in response to the stimulation current. In this way, the tissue is not exposed to DC current. The relative phase between the clock driving the stimulation current and the clock driving the chop frequency of the mixer amplifier can be changed to allow the instrumentation amplifier to measure either the resistance or reactance of the tissue. For resistance, the chop frequencies of the front end and the mixer amplifier ordinarily will be in-phase with one another.

According to an additional example embodiment, the instrumentation amplifier may be configured to be useful in telemetry applications, e.g., as a down mixer in a receiver. In this example embodiment, the instrumentation amplifier may be located in a patient or clinician programmer or an implantable pulse generator (IPG) or other implantable medical device (IMD) implanted within a patient that communicates, via wireless radio frequency (RF) telemetry, with the clinician or patient programmer. The front end in this example embodiment includes a transmitter located in a remote transmitting device, and a receive antenna in the receiving device for receiving a telemetry signal from the transmitter. The telemetry signal may, for example, have a frequency in a range of approximately 10 kHz to 1 GHz, and in some embodiments approximately 175 kHz, although other frequencies are possible. In this example, the first chopper actually resides in the transmitter of the remote device. The front end couples the transmitted signal, which is a signal modulated at the chopper frequency, to the mixer amplifier which directly down-modulates the signal to baseband while substantially eliminating 1/f noise and offset from the mixer. A phase locked loop, or other clock synchronization circuit, may be included to provide feedback to keep the transmitter (front end) and receiver (mixer amplifier) in phase with each other.

Telemetry signals may include data, programming instructions of the like. For example, a medical device programmer may transmit telemetry signals to an implanted medical device to download programming instructions that alter operational aspects of the implanted medical device, such as therapies delivered by the implanted medical device. The programming instructions may specify new stimulation or drug delivery programs or adjustments to existing programs. The programming instructions may specify adjustments to programming parameters, such as electrical stimulation pulse amplitude, pulse width, pulse rate, or duration, or drug delivery dosage, drug delivery rate, dosage limits, lockout intervals, or the like. Likewise, an implanted medical device may transmit data to an external programmer via the telemetry signals. The data may transmitted to the programmer may include operational data, diagnostic data, fault data, sensor data, or the like.

Physiological signals are generally found at low frequencies, e.g., less than or equal to approximately 100 Hz and, in many cases, less than or equal to approximately 2 Hz, or less than or equal to approximately 1 Hz. Measurement and analysis of physiological signals can be used to diagnose chronic or acute disease states and other medical conditions. Example physiological signals include EEG signals, ECG signals, EMG signals, pressure, impedance, and motion signals, as previously described. Such signals may be used to detect or measure cardiac ischemia, pulmonary edema, breathing, activity, posture, pressure, brain activity, gastrointestinal activity, and the like.

Implantable medical devices including instrumentation amplifiers used to measure such physiological signals may be required to operate with low noise and low power. Low power consumption may be especially important in chronically implanted medical devices designed for several years of services, and particularly those medical devices configured to sense physiological signals and deliver therapies. Examples of therapeutic medical devices are implantable cardiac pacemakers, implantable cardioverter-defibrillators, implantable electrical stimulators, such as neurostimulators, muscle stimulators or other tissue stimulators, implantable drug delivery devices, and other devices.

It is important that an instrumentation amplifier provide low noise performance so that noise does not result in reduced sensitivity or wrong or misleading diagnostic information. It is also important that the instrumentation amplifier operate with low power in order to conserve limited battery resources and thereby promote operational longevity of the implantable medical device. A chopper-stabilized instrumentation amplifier, as described in this disclosure, may be configured to achieve precise measurements at low frequency with low power. As will be described, a chopper-stabilized instrumentation amplifier can be configured to apply chopping at low impedance nodes and apply feedback to reduce ripple resulting from low bandwidth of the amplifier.

FIG. 1 is a block diagram illustrating a chopper stabilized instrumentation amplifier 10 that is configured to achieve stable measurement at low frequency with very low power. Instrumentation amplifier 10 uses a differential architecture and a mixer amplifier to substantially eliminate 1/f noise, popcorn noise, and offset. Dynamic limitations, i.e., glitching, that result from chopper stabilization at low power are eliminated through a combination of chopping at low impedance nodes within a mixer amplifier 14 and feedback via feedback path 16. The signal path of the instrumentation amplifier operates as a continuous time system, providing minimal aliasing of noise or external signals entering the signal pathway at the chop frequency or its harmonics. As a result, instrumentation amplifier 10 can provide stable measurements for low frequency signals, such as physiological signals and other signals having a frequency of less than approximately 100 Hz, and preferably less than or equal to approximately 2.0 Hz, and more preferably less than or equal to approximately 1.0 Hz, while operating under the constraints of a micro power system, e.g., drawing a supply current of less than or equal to approximately 2.0 microamps, and more preferably less than or equal to approximately 1.0 microamps, and requiring a supply voltage of less than or equal to approximately 2.0 volts, and more preferably less than or equal to approximately 1.5 volts.

As shown in FIG. 1, instrumentation amplifier 10 includes front end 12, mixer amplifier 14, and feedback path 16. In the example of FIG. 1, front end 12 may provide a switched or static capacitive differential interface to mixer amplifier 14, e.g., for measurement of a low frequency voltage amplitude. In other embodiments, front end 12 may be configured for impedance measurement or telemetry applications. Front end 12 couples a differential modulated (chopped) input signal that carries a low frequency signal of interest on a carrier (chopper) frequency. In other words, front end 12 shifts a low frequency signal that is subject to introduction of low frequency noise by mixer amplifier 14 to a carrier frequency at which the mixer amplifier 14 does not introduce substantial noise into the signal. The low frequency signal of interest may have, for example, a frequency within a range of 0 to approximately 100 Hz. In some embodiments, the carrier (chopper) frequency may be within a frequency range of approximately 4 kHz to 200 kHz. Front end 12 modulates the low frequency signal prior to introduction to mixer amplifier 14 so that the original baseband (low frequency) signal components are not corrupted by noise components introduced by mixer amplifier 14 at low frequency.

Noise generally enters the signal path of instrumentation amplifier 10 through mixer amplifier 14. However, mixer amplifier 14 should not introduce noise to the modulated signal at the carrier frequency. Rather, the noise components are typically present at low frequency and may include 1/f noise or popcorn noise. In addition, noise in the form of dc offset cannot be introduced at the carrier frequency. Mixer amplifier 14 receives and amplifies the up-modulated input signal from front end 12. Again, the up-modulated input signal is up-modulated to the chopper frequency to protect the input signal from low frequency noise and offset.

Mixer amplifier 14 demodulates the modulated input signal from the carrier frequency to the baseband of interest while upmodulating the mixer amp 1/f noise and offset out of the measurement band. Thus, the original low frequency signal components are demodulated back to baseband without the low frequency noise and offset components of the mixer amplifier 14. Mixer amplifier 14 passes only the baseband signals, i.e., signals with frequency components of approximately 100 Hz or less, as output and substantially reduces or eliminates the noise components located at the carrier frequency. Thus, the output of instrumentation amplifier 10 contains the low frequency signal components of interest. In addition, mixer amplifier 14 provides a gain amplifier that amplifies the input signal. In this way, instrumentation amplifier 10 provides a low noise output while operating at low power.

Instrumentation amplifier 10 operates under the constraints of a micro power system and therefore has limited bandwidth. The limited bandwidth of instrumentation amplifier 10 can cause glitching or ripple in the passband of the output signal. As will be described, mixer amplifier 14 may have a modified folded cascode architecture that provides switching, e.g., via CMOS switches, at low impedance nodes. Switching at low impedance nodes enables chopping at higher frequencies where the only limitation would be the charge injection residual offset.

Feedback path 16 is coupled between the output of mixer amp 14 and front end 12 to reduce the ripple. Feedback path 16 may have a differential configuration that substantially eliminates glitching in the output signal by driving the net input signal to mixer amplifier 14 toward zero. In this way, feedback path 16 keeps the signal change at the input of mixer amplifier 14 relatively small in steady state. As a result, instrumentation amplifier 10 achieves a stable, low noise, low distortion output while operating at low power.

Instrumentation amplifier 10 may be useful in many different applications. This disclosure presents various example embodiments of instrumentation amplifier 10. However, these example embodiments should not be considered limiting of the instrumentation amplifier 10 as broadly embodied and described in this disclosure. Rather, it should be understood that the example embodiments described in this disclosure are a subset of many different example embodiments within the scope of this disclosure.

In some embodiments, a device such as an implantable medical device may include multiple instrumentation amplifiers 10. For example, multiple instrumentation amplifiers 10 may be fabricated in parallel to provide multiple sensing channels. The multiple sensing channels may sense the same type of physiological information, e.g., at different positions or angles, or via different sensors. In addition, multiple sensing channels may sense different types of physiological information, such as impedance, ECG, EEG, EMG, pressure, motion, and the like.

According to one example embodiment, front end 12 of amplifier 10 may comprise a continuous time switched capacitor network. The switched capacitor network includes a differential set of switched input capacitors that toggle between input voltages at the positive and negative terminals of instrumentation amplifier 10. By toggling the switched input capacitors at the chopper frequency, the differential input signal is chopped. In this manner, the differential input signal is up-modulated to the carrier frequency, yielding a modulated signal at the differential input of mixer amplifier 14. In this example, instrumentation amplifier 10 may be implemented to measure physiological voltage signals such as ECG, EEG, EMG, pressure, motion, or the like. Accordingly, the inputs to front end 12 may be electrodes, or outputs from any of a variety of accelerometers, pressure sensors, strain gauge sensors, or the like.

According to another example embodiment, front end 12 of instrumentation amplifier 10 may comprise an impedance sensor. In particular, instrumentation amplifier 10 may form a biological impedance sensing device for measuring the impedance of tissue of a patient, e.g., muscle tissue, organ tissue, brain tissue, adipose tissue, or a combination of tissues. The impedance sensor formed by front end 12 produces an AC modulated signal that is AC coupled to mixer amplifier 14 through the tissue of the patient. In this case, front end 12 modulates a stimulation current to modulate the amplitude of a tissue voltage signal. In other words, front end 12 chops the stimulation current source. Thus, the patient is not exposed to a direct current (DC) signal. Moreover, the modulated signal may not substantially excite the tissue, thereby decreasing the likelihood that the patient may experience discomfort or other detrimental effects from the modulated signal. The relative phase between the clock driving the stimulation current and the clock driving the chop frequency of mixer amplifier 14 can be changed to allow the instrumentation amplifier to measure either the resistance or reactance of the tissue. Consequently, instrumentation amplifier 10 may be used to measure a variety of physiological signals, e.g., for pulmonary edema, minute ventilation (sleep apnea), cardiac dynamics, and general tissue impedance. For example, the relative phase between the stimulation current and mixer amplifier clocks may be dynamically adjusted to obtain different types of measurement, e.g., resistance or reactance, during the course of measurement.

According to an additional example embodiment, feedback 16 may include a second feedback path in addition to the previously described negative feedback path that reduces glitching in the output of instrumentation amplifier 10 and provides the nominal gain for amplifier 10. This second feedback path provides negative feedback to allow for the construction of a high pass filter. The second feedback path is dominant at low frequencies, i.e., frequencies lower than the cutoff frequency, and the chopper stabilized negative feedback path is dominant at passband frequencies. The high pass filter may have a cutoff frequency approximately equal to, e.g., approximately 2.5 Hz, or 0.5 Hz, or 0.05 Hz. In this case, the first feedback path, i.e., the "chopper stabilizing" feedback path that eliminates glitching at the output, is dominant at pass band frequencies and the second "high-pass filter" feedback path is dominant at low frequencies. The corner frequency of the high pass filter in the second feedback path can be set by the scaling of feedback capacitors in the first feedback path and the time-constant of a switched capacitor integrator in the second feedback path. As one example, the high pass filter provided by this feedback path may be useful for rejecting post-pacing artifacts in heart monitoring applications and filtering out electrode offsets. The second feedback path may include a high-pass integrator that is chopper stabilized for the lowest 1/f noise floor.

According to yet another embodiment, feedback 16 may include a third feedback path in addition to the first feedback path. The third feedback path provides positive feedback to increase the input impedance of instrumentation amplifier 10. The increased input impedance is achieved by sampling the output of instrumentation amplifier 10 and applying a scaled charge to the input of the switched capacitors in front end 12 to provide compensatory charge at the sensor input. The scaled charge may be applied at a point in the signal flow prior to chopping of the input signal. The injected current effectively "replaces" charge lost during the sampling of the input chopper capacitors in front end 12. This charge replacement feedback may be considered similar to base current compensation. The positive feedback may increase the equivalent low-frequency input impedance of instrumentation amplifier 10 by an order of magnitude or more. This third feedback path may not be necessary in various applications. If increased input impedance is desired, however, this third feedback path can be readily added.

According to a further example embodiment, instrumentation amplifier 10 may include the previously described second and third feedback paths in addition to the first (chopper stabilizing) feedback path. In this case, the third feedback path does not tap off of the output signal of instrumentation amplifier 10 as previously described. Rather, the third, positive feedback path may tap off of an integrated signal provided by the second, high-pass filter feedback path. Accordingly, various combinations of first, second, and/or third feedback paths may be provided to address glitching, low frequency rejection, and/or amplifier input impedance.

In another example embodiment, instrumentation amplifier 10 may be used in telemetry applications and, more particularly, telemetry applications operating at relatively low frequencies and low power, e.g., on the order of approximately 175 kHz in a medical device. For example, instrumentation amplifier 10 may be used as a telemetry receiver in an implantable pulse generator (IPG), implantable drug pump, or other implantable medical device (IMD) implanted within a patient that communicates, via wireless radio frequency (RF) telemetry, with a clinician or patient programmer, or with other implanted or external medical devices. Instrumentation amplifier 10 may also be used, in a reciprocal manner, as a telemetry receiver in a clinician or patient programmer that communicates with an IPG implanted within a patient. When implemented as a telemetry receiver, front end 12 may include a transmitter and a receive antenna for receiving a transmitted signal from the transmitter. However, the transmitter portion of front end 12 actually resides in the remote device that transmits the signal. Front end 12 couples the received signal to mixer amplifier 14, which directly-down mixes the received signal to baseband while substantially eliminating 1/f noise and offset. A phase locked loop may provide feedback to keep the clocks at the transmitter and receiver in phase with each other.

Instrumentation amplifier 10 can provide one or more advantages in a variety of embodiments. For example, as previously described, instrumentation amplifier 10 can achieve stable measurements at low frequency with low power. This is a result of the basic architecture of instrumentation amplifier 10. As another advantage, on-chip, poly-poly capacitors may be used to implement feedback capacitors in instrumentation amplifier 10. Poly-poly capacitors enable fast switching dynamics and can be formed on-chip with other amplifier components. A poly-poly capacitor may be formed on chip with other devices by combining two polysilicon electrodes and an intervening silicon dioxide dielectric. The gain of the instrumentation amplifier can be set by the ratio of the feedback capacitors to the input capacitors and centered around a selected reference voltage. Further, by modulating the input signal at front end 12, the common mode input voltage can swing from rail to rail and mixer amplifier 14 is still able to extract a differential voltage. These advantages are merely exemplary and should be considered a subset of potential advantages provided by instrumentation amplifier 10. Additional advantages are discussed in this disclosure or may occur to those skilled in the art upon consideration of this disclosure. Moreover, such advantages may not coexist in every embodiment.

Figure 2:
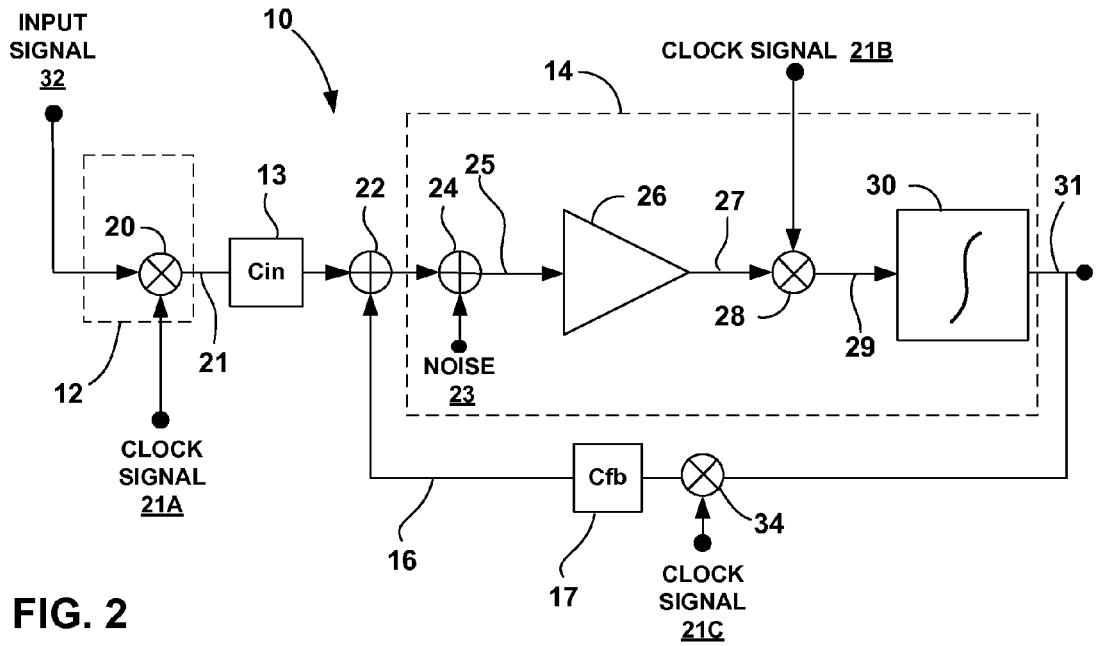
FIG. 2 is a diagram illustrating a signal flow path of the instrumentation amplifier of FIG. 1.

FIG. 2 is a block diagram illustrating a signal path flow of an exemplary instrumentation amplifier 10. In FIG. 2, front end 12 includes modulator 20 for modulating a low frequency input signal 32 to produce modulated input signal 21. An input capacitance (Cin) 13 couples the output of modulator 20 to summing node 22. For a differential input signal, Cin 13 may include a first input capacitor coupled to a first input of mixer amplifier 14 and a second input capacitor coupled to a second input of mixer amplifier 14. Modulator 20 modulates a differential amplitude of input signal 32 to a carrier frequency provided by clock signal 21A. Clock signal 21A, like other clock signals described in this disclosure, may be a square wave signal that effectively multiples the signal by plus 1 and minus 1 at a desired clock frequency. In this manner, module 20 chops the input signal 32 prior to application of the input signal to mixer amp 14. Modulator 20 may, in some embodiments, comprise a pair of complementary metal oxide semiconductor (CMOS) single pole, double throw (SPDT) switches that are driven by clock signal 21A to modulate (chop) input signal 32 to the carrier frequency. The CMOS SPDT switches may be cross-coupled to each other to reject common mode signals.

In one example embodiment, the CMOS switches may be coupled to a set of differential capacitors to form a continuous time switched capacitor network that forms input capacitance Cin at the input of mixer amplifier 14. In this case, front end 12 may be coupled to a physiological sensor that generates an input signal 32 proportional to a sensed physiological parameter at its outputs. For example, input signal 32 may be a differential output signal from a pair or electrodes, or from an accelerometer, pressure sensor, or the like. In another example embodiment, the CMOS switches may be coupled to capacitors that AC couple modulated input signal 21 to the input of mixer amplifier 14. In this case, front end 12 may be an impedance sensor that modulates a stimulation current which is applied across tissue of a patient. In an additional embodiment, front end 12 may be part of a telemetry transmitter. In this case, input signal 32 is an electrical signal encoded with data that is modulated to the carrier frequency by clock signal 21A for transmission over a wireless channel.

Feedback summing node 22 will be described below in conjunction with feedback path 16. Summing node 24 represents the introduction of offset and 1/f noise within mixer amplifier 14. At summing node 24, the original baseband components of input signal 32 are located at the carrier frequency. The baseband signal components of input signal 32 may have a frequency within a range of 0 to approximately 100 Hz and the carrier frequency may be approximately 4 kHz to approximately 10 kHz. Noise 23 enters the signal pathway at summing node 24 to produce noisy modulated input signal 25. Noise 23 may include 1/f noise, popcorn noise, offset, and any other external signals that may enter the signal pathway at low (baseband) frequency. At node 24, however, the original low frequency components have already been chopped to a higher frequency band by modulator 20. Thus, the low frequency noise 23 is segregated from the original low frequency components.

Mixer amplifier 14 receives noisy modulated input signal 25 from node 24. In the example of FIG. 2, mixer amplifier 14 includes gain amplifier 26, modulator 28, and integrator 30. Amplifier 26 amplifies noisy modulated input signal 25 to produce amplified signal 27. Modulator 28 demodulates amplified signal 27. That is, modulator 28 modulates noise 23 up to the carrier frequency and demodulates the original baseband signal components from the carrier frequency back to baseband. Modulator 28 may comprise switches, e.g., CMOS SPDT switches, located at low impedance nodes within a folded-cascode architecture of mixer amplifier 14. Modulator 28 is supplied with clock signal 21B to demodulate amplified signal 27 at the same carrier frequency as clock signal 21A. Hence, clock signals 21A, 21B should be synchronous with each other. In some embodiments, clock signal 21A and clock signal 21B may be the same signal, i.e., supplied by the same clock. In other embodiments, e.g., for measurement of reactance, the relative phasing of clock signals 21A, 21B and 21C may be altered.

In some embodiments, clock signal 21A and clock signal 21B may be supplied by different clocks. In such embodiments, modulators 20 and 28 may not be precisely in phase with each other and additional circuitry may be added to ensure that clock signals 21A and 21B remain in phase with each other. This is the case when instrumentation amplifier 10 is used as a telemetry receiver because modulator 20 may be used by a transmitter in a remote device to modulate the signal for transmission over a wireless channel while modulator 28 may be used by the receiver to demodulate the received signal. Thus, additional signal processing, such as a phase locked loop, may be used to keep modulators 20, 28 in phase with each other.

Figure 6:
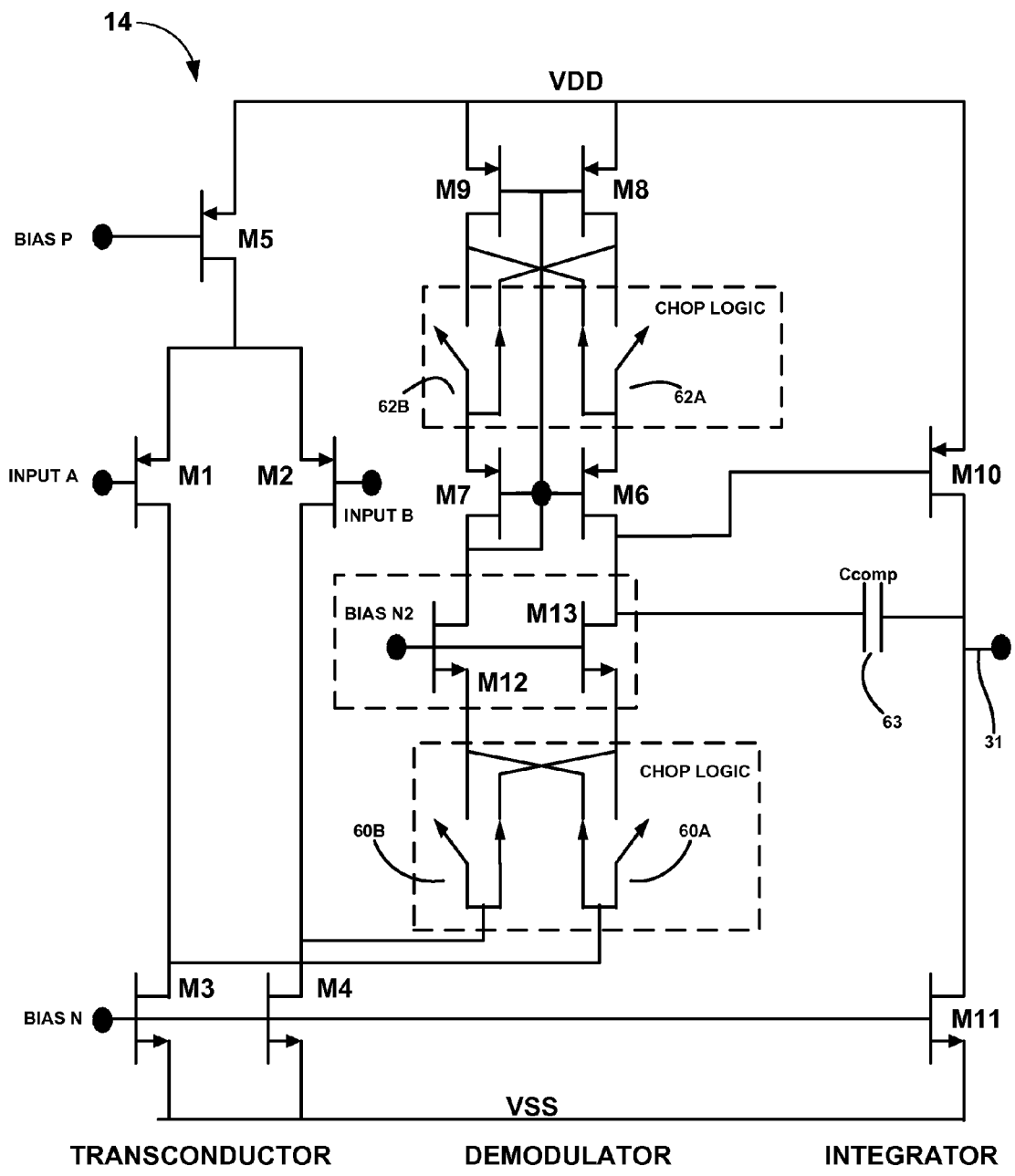
FIG. 6 is a circuit diagram illustrating a chopper-stabilized mixer amplifier forming part of an instrumentation amplifier.

Integrator 30 operates on demodulated signal 29 to pass the low frequency signal components at baseband and substantially eliminate noise components 23 at the carrier frequency. In this manner, integrator 30 provides compensation and filtering. In other embodiments, compensation and filtering may be provided by other circuitry. However, the use of integrator 30 as described in this disclosure may be desirable. FIG. 6 provides a detailed circuit diagram of an example embodiment of mixer amplifier 14. Feedback path 16, as shown in FIG. 2, provides negative feedback to the input of mixer amp 14 to reduce glitching in output signal 31. In particular, feedback path 16 drives modulated signal 25 toward zero in steady state. In this way, feedback 16 keeps the signal change at the input to mixer amplifier 14 small. Feedback path 16 includes a modulator 34, which modulates output signal 31 to produce a differential feedback signal 35 that is added to the signal path between front end 12 and mixer amplifier 14 at node 22.

Feedback path 16 provides capacitor scaling versus the input capacitance Cin of mixer amplifier 14 to produce attenuation and thereby generate gain at the output of amplifier 10. Accordingly, feedback path 16 may include a feedback capacitance (Cfb) 17 that is selected to produce desired gain, given the value of the input capacitance (Cin) 13 of mixer amplifier 14. Integrator 30 may be designed to provide a stable feedback path 16 with acceptable bandwidth while also filtering out the upmodulated offset and 1/f noise from the measurement band.

Clock signal 21C drives modulator 34 in feedback path 16 to modulate output signal 31 at the carrier frequency. Clock signal 21C may be derived from the same clock as clock signal 21B. However, because output signal 31 is single ended, feedback 16 includes two feedback paths that apply the negative feedback to the positive and negative input terminals of mixer amplifier 14. Thus, the two feedback paths should be 180 degrees out of phase with each other, with one of the feedback paths modulating synchronously with modulator 28. This ensures that a negative feedback path exists during each half of the clock cycle.

As an alternative, in some embodiments, mixer amplifier 14 may be configured to generate a differential output signal, rather than a single-ended output signal. A differential output signal may provide positive and negative outputs. In this case, feedback path 16 can feed back the positive output to the positive input of mixer amplifier 14 and feed back the negative output to the negative input of the mixer amplifier. For a differential output signal, feedback path 16 would modulate each of the positive and negative outputs. However, the positive and negative outputs could be modulated in-phase, rather than out of phase. Although a differential output is possible, a feedback path 16 configured to convert a single-ended output to differential feedback will be described herein for purposes of illustration.

In FIG. 2, only the previously described negative feedback path 16 is shown. That is, the previously described feedback paths for increasing input impedance and constructing a high pass filter are excluded from FIG. 2. These feedback paths are excluded in FIG. 2 because they are not necessary for proper operation of instrumentation amplifier 10. The feedback paths, however, are included in the signal flow path diagrams in FIGS. 10 and 12, and may be highly desirable in some applications.

Figure 3A:
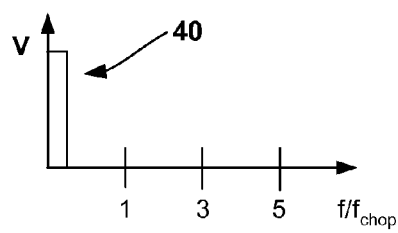
FIGS. 3A-D are graphs illustrating frequency components of a signal at various stages within the signal flow path of FIG. 2.

FIGS. 3A-3D are graphs illustrating the frequency components of a signal at various stages within the signal flow path of FIG. 2. In particular, FIG. 3A illustrates the frequency components of input signal 32. The frequency components are represented by block 40 and located at baseband in FIG. 3A.

Figure 3B:
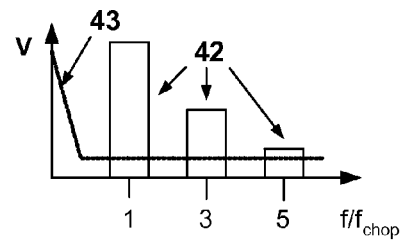

FIG. 3B illustrates the frequency components of noisy modulated input signal 25. In FIG. 3B, the original baseband frequency components of noisy modulated input signal 25 are modulated and represented by blocks 42 at the odd harmonics. The frequency components of noise 23 are represented by dotted line 43. It is clear in FIG. 3A that the energy of the frequency components of noise 23 is located at baseband and energy of the original low frequency components is located at the carrier (chop) frequency and its odd harmonics.

Figure 3C:
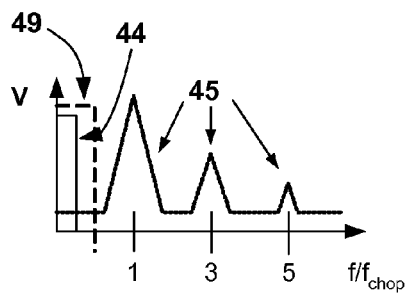

FIG. 3C illustrates the frequency components of demodulated signal 29. In particular, the original low frequency components of demodulated signal 29 are located back at baseband and represented by block 44. The frequency components of noise 23 are modulated and represented by dotted line 45. The frequency components of noise 23 are located at the carrier (chop) frequency odd harmonics in FIG. 3C. FIG. 3C also illustrates the effect of a low pass filter that may be applied to demodulated signal 29 by integrator 30. The low pass filter effect is represented by dashed line 49.

Figure 3D:
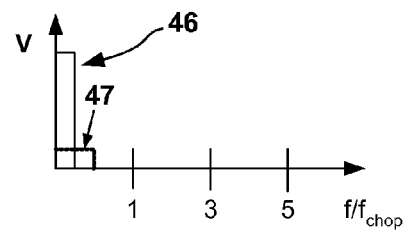

FIG. 3D is a graph that illustrates the frequency components of output signal 31. In FIG. 3D, the frequency components of the original low frequency components are represented by block 46 and the frequency components of noise 23 are represented by dotted line 47. FIG. 3D illustrates that integrator 30 removes the frequency components from noise 23 that were located outside of the passband of the low pass filter shown in FIG. 3C. Clearly, the energy from noise 23 is substantially eliminated from output signal 31, or at least substantially reduced relative to the original noise and offset that otherwise would be introduced.

Figure 4A:
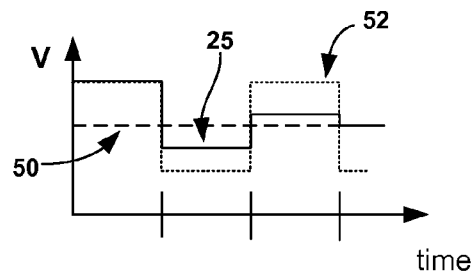
FIGS. 4A-D are graphs illustrating a signal at different stages within the signal flow path of FIG. 2.
Figure 4B:
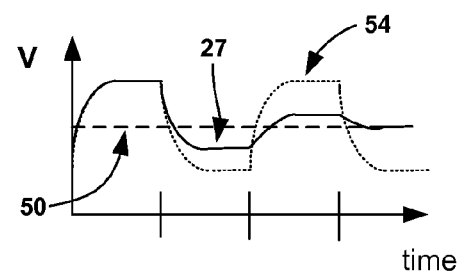
Figure 4C:
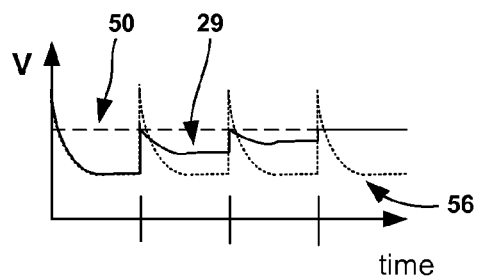
Figure 4D:
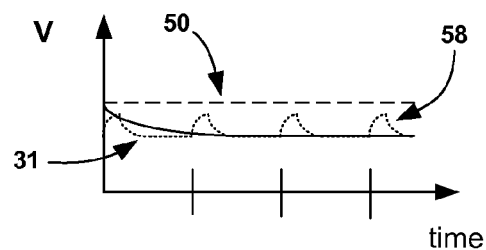

FIGS. 4A-4D are graphs illustrating the step response time domain behavior of a chopper stabilized signal at different stages within instrumentation amplifier 10. In particular, with reference to FIG. 2, FIGS. 4A-4D illustrate the time domain behavior of noisy modulated input signal 25, amplified signal 27, demodulated signal 29, and output signal 31, respectively. For reference, each of FIGS. 4A-4D also illustrate signals 52, 54, 56, 58 and a selected reference voltage 50. Signals 52, 54, 56, and 58 correspond to signals 25, 27, 29, and 31, respectively, and illustrate the time domain behavior without negative feedback via feedback path 16. In FIGS. 4A-4C, signals 25, 27, and 29 are centered around reference voltage 50 at time zero, and suppressed toward reference voltage 50 over time by negative feedback. Hence, by adding negative feedback via feedback path 16, ac signals are driven to zero in steady state.

In general, FIGS. 4A-4D illustrate elimination of transient glitches within instrumentation amplifier 10 through the use of feedback path 16 and switching at low impedance nodes within mixer amplifier 14. This glitching results from the dynamic limitations of instrumentation amplifier 10. However, feedback 16 substantially suppresses the glitching by driving the active signal within mixer amplifier 14 toward zero, or reference voltage 50 in FIGS. 4A-4D, in steady state.

The graph in FIG. 4A shows noisy modulated input signal 25 and corresponding signal 52 without negative feedback. Signals 25 and 52 are centered around reference voltage 50. Noisy modulated input signal 25 is amplified by mixer amplifier 14 to generate amplified signal 27.

As shown in FIG. 4B, the limited bandwidth of amplifier 26 tends to soften or round the edges of amplified signal 27 and corresponding signal 54 due to its finite rise time. When amplified signal 27 is demodulated with a square wave, demodulated signal 29 appears as a series of spikes superimposed on the desired signal, as shown in FIG. 4C. Accordingly, output signal 31 also appears as a series of spikes superimposed on the desired signal in FIG. 4D. The spikes in output signal 31 can create a significant sensitivity error because the spikes subtract energy from the desired signal. In addition, the spikes are difficult to suppress to an acceptable level without a very high order low pass filter. Moreover, the spikes are particularly problematic because the spikes may be similar to signals that may be of interest, such as intrinsic and evoked ECG heart potentials or EEG seizure activity.

Instrumentation amplifier 10 substantially suppresses the glitching in steady state through feedback 16. Feedback 16 applies output signal 31 back to the input of mixer amplifier 14 to drive noisy modulated signal 25 toward zero in steady state. Consequently, little dynamic performance is required of mixer amplifier 14. This is achieved through partitioning the modulation processes before the signal is integrated in mixer amplifier 14, which decouples the overall loop dynamics from the switching (modulating) dynamics. Moreover, by closing the feedback path, the overall gain of instrumentation amplifier 10 is set by the ratio of the input capacitors, i.e., capacitors Cin in front end 12, and feedback capacitors, i.e., capacitors Cfb in feedback path 16. Setting gain through capacitors ratios makes sensitivity generally immune to process variations in the transistors. In this way, feedback 16 enables instrumentation amplifier 10 to achieve stable (low-noise) measurements at low frequency with very low power.

The gain of instrumentation amplifier 10 may be different for different applications. For ECG sensing, for example, a gain of approximately 50 may be desirable. For EEG sensing, a gain closer to 500 may be desirable. As one example, Cin could be set to 20 picofarads (pF) and Cfb could be set to 40 femtofarads (fF) to achieve a gain of approximately 500, e.g., for EEG sensing. As another example, Cin could be set to 10 pF and Cfb could be set to 200 fF to achieve a gain of approximately 50.

Figure 5:
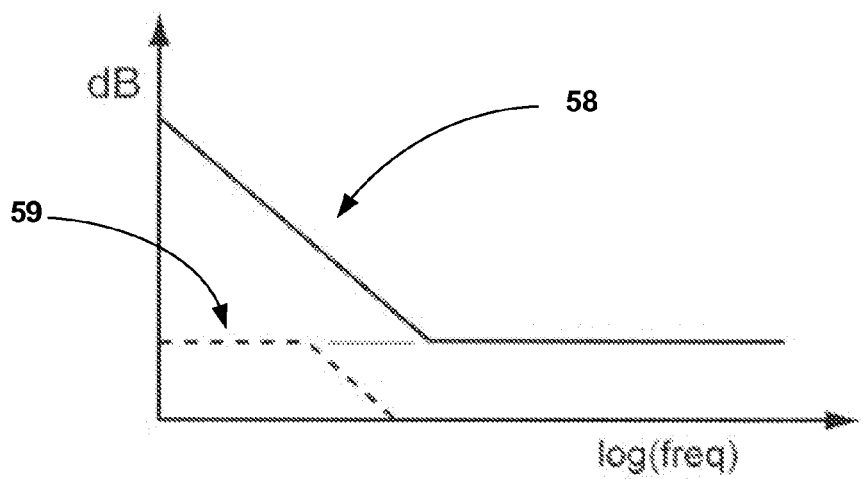
FIG. 5 is graph illustrating exemplary noise performance of a chopper-stabilized instrumentation amplifier.

FIG. 5 is a bode plot illustrating exemplary noise performance of instrumentation amplifier 10. In particular, lines 58 and 59 in the bode plot represent the noise prior to chopping (prior to the input of mixer amplifier 14), and the noise after chopping (at the output of mixer amplifier 14), respectively. Line 58 shows that the noise content prior to chopping is primarily located at low frequency. At high frequency, only white noise is present. In a preferred embodiment, the chop frequency is above the corner of the 1/f noise and thermal noise intercept point. Accordingly, line 59 shows that the noise contained in the signal after chopping is substantially eliminated. The noise that is contained in the signal after chopping is essentially the theoretical white noise limit.

FIG. 6 is a circuit diagram illustrating an example embodiment of mixer amplifier 14 of instrumentation amplifier 10 in greater detail. As previously described, mixer amplifier 14 amplifies noisy modulated input signal 25 to produce an amplified signal and demodulates the amplified signal. Mixer amplifier 14 also substantially eliminates noise from the demodulated signal to generate output signal 31. In the example of FIG. 6, mixer amplifier 14 is a modified folded-cascode amplifier with switching at low impedance nodes.

The modified folded-cascode architecture allows the currents to be partitioned to maximize noise efficiency. In general, the folded cascode architecture is modified in FIG. 6 by adding two sets of switches. One set of switches is illustrated in FIG. 6 as switches 60A and 60B (collectively referred to as "switches 60") and the other set of switches includes switches 62A and 62B (collectively referred to as "switches 62").

Switches 60 are driven by chop logic to support the chopping of the amplified signal for demodulation at the chop frequency. In particular, switches 60 demodulate the amplified signal and modulate front-end offsets and 1/f noise. Switches 62 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The output 31 of amplifier 26 is at baseband, allowing an integrator formed by transistor M10 and capacitor 63 (Ccomp) to stabilize feedback path 16 (not shown in FIG. 6) and filter modulated offsets.

Mixer amplifier 14 has three main blocks: a transconductor, a demodulator, and an integrator. The core is similar to a folded cascode. In the transconductor section, transistor M5 is a current source for the differential pair of input transistors M1 and M2. In some embodiments, transistor M5 may pass approximately 800 nA, which is split between transistors M1 and M2, e.g., 400 nA each. Transistors M1 and M2 are the inputs to amplifier 14. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 60 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 63 (Ccomp). Switches 62 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 66 suppressed. Bias N2 transistors M12 and M13 form a common gate amplifier that presents a low impedance to the chopper switching and passes the signal current to transistors M6 and M7 with immunity to the voltage on the drains.

The output DC signal current and the upmodulated error current pass to the integrator, which is formed by transistor M10, capacitor 63, and the bottom NFET current source transistor M11. Again, this integrator serves to both stabilize the feedback path and filter out the upmodulated error sources. The bias for transistor M10 may be approximately 100 nA, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 6 may be field effect transistors (FETs), and more particularly CMOS transistors.

Figure 7:
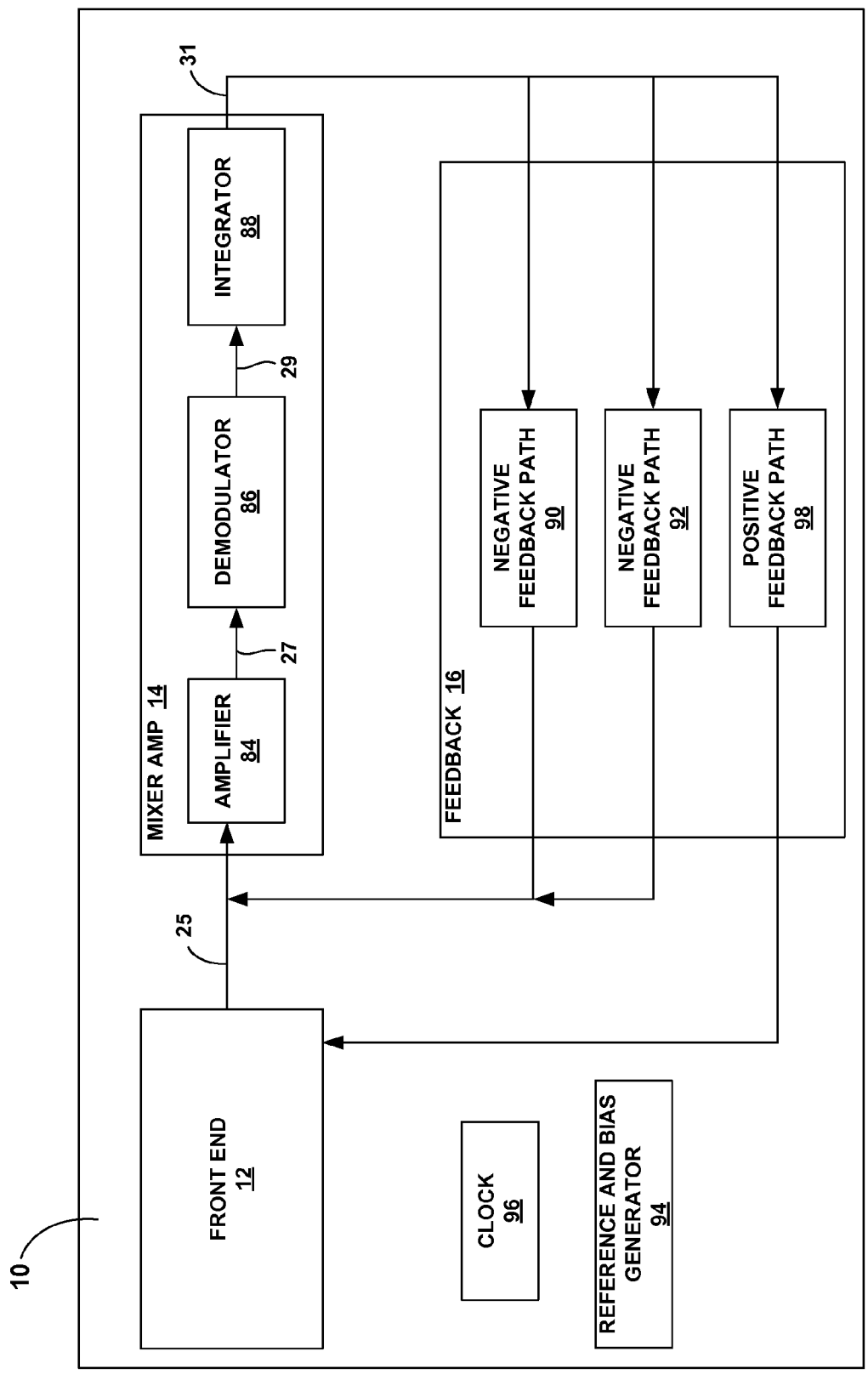
FIG. 7 is a block diagram illustrating an example embodiment of the instrumentation amplifier of FIG. 1 in greater detail.

FIG. 7 is a block diagram illustrating instrumentation amplifier 10 in greater detail. It should be understood that FIG. 7 is merely exemplary and should not be considered limiting of the invention as described in this disclosure in any way. Rather, it is the purpose of FIG. 7 to provide an overview that is used to describe the operation of instrumentation amplifier 10 in greater detail. This overview is used as a framework for describing the previously mentioned example embodiments with respect to the detailed circuit diagrams provided in this disclosure.

In FIG. 7, front end 12 outputs a modulated differential input signal 25. The modulated differential input signal carries the signal of interest at a carrier frequency. As previously described, front end 12 may take the form of various different components. Front end 12 may, for example, be a continuous time switched capacitor network that modulates (chops) an input signal from a physiological sensor, an impedance sensor that modulates a stimulation current to produce an AC modulated signal that is AC coupled to mixer amplifier 14 through tissue of a patient, or part of a telemetry transmitter that modulates the data encoded output signal to a carrier frequency for transmission over a wireless channel. Thus, it should be understood that front end 12 may be any component or combination of components that produces a differential modulated input signal as broadly described in this disclosure.

In particular, when implemented with a continuous time switched capacitor network coupled to a physiological sensor, the continuous time switched capacitor network operates as a modulator that modulates (chops) the differential signal output by the physiological sensor to a carrier frequency. The physiological sensor may be a set of electrodes, an accelerometer, a pressure sensor, a voltage sensor or other sensor that outputs a differential voltage signal. In particular, the physiological sensor may, for example, generate a differential signal proportional to physiological signals such as, ECG signals, EMG signals, EEG signals, or other signals. The differential signal generated by the sensor is a low frequency signal. Using physiological signals as an example, the frequency of the differential signal may be within a range of approximately 0 Hz to approximately 100 Hz, and may be less than approximately 2 Hz, and in some cases less than approximately 1 Hz.

Sensors other than physiological sensors may also be used. That is, the sensor does not need to output a differential signal proportional to a physiological signal. Rather, the sensor may be any electrode, accelerometer, pressure sensor, voltage sensor or other sensor that outputs a differential signal, which may or may not represent a physiological signal or serve a medical sensing application. However, in the case of a physiological sensor, the carrier frequency may be within a range of approximately 4 kHz to approximately 10 kHz, although other frequencies are possible. It is important, however, that the carrier frequency be sufficiently higher than the frequency of the baseband signal of interest and within a range that does not introduce significant noise into the signal, i.e., a frequency at which mixer amplifier 14 operates without introducing noise into the signal.

In this case, the modulator in front end 12 may include a differential set of switches, e.g., CMOS switches, that are toggled between the outputs of the physiological sensor to modulate (chop) an amplitude of the input signal. Clock 96 supplies the clock signal that the modulator in the front end 12 and demodulator 86 in mixer amplifier 14 use to modulate the differential input signal at the carrier (chop) frequency. At one end, the switches are cross coupled to each other and toggle between the output terminals of the sensor to reject common mode signals and operate as continuous time process, i.e., a non-sampling process. The switches are coupled at the other end to input capacitors of mixer amplifier 14 to form a continuous time switched capacitor network. In this way, front end 12 amplitude modulates (chops) the differential input signal at the inputs to mixer amplifier 14. Consequently, the modulated differential input signal produced by front end 12 is a square wave with a frequency equal to the carrier frequency. A circuit diagram for this example embodiment is provided in FIG. 8.

When front end 12 is implemented as an impedance sensor, front end 12 may include a set of CMOS SPDT switches that are coupled at one end to reference potentials and to corresponding resistors at the other end. The switches toggle between the reference potentials and are cross-coupled to each other to modulate (chop) a stimulation current through the resistors and reject common-mode signals. The resistors may be connected in series to respective capacitors that are AC coupled to mixer amplifier 14 through tissue of a patient. The chopped stimulation current produces a chopped voltage on the tissue with an amplitude modulated at the carrier frequency that is AC coupled to mixer amplifier 14. A circuit diagram is provided for this example embodiment in FIG. 9.

When instrumentation amplifier 10 is used to demodulate telemetry signals, front end 12 may be viewed as part of a transmitter in the telemetry system. In particular, front end 12 may be implemented using any circuitry known in the art of telemetry that modulates a data encoded signal to a carrier frequency for transmission over a wireless channel. For example, front end 12 may be viewed as part of a receiver located in an IPG that is implanted within a patient and communicates with a clinician or patient programmer. Alternatively, front end 12 may be part of a receiver of the clinician or patient programmer that communicates with the IPG implanted within the patient. A detailed block diagram for this example embodiment is provided in FIG. 15A.

In any case, front end 12 generates a differential input signal for mixer amplifier 14. Noise, e.g., 1/f noise, popcorn noise, and offset, enters the signal path of instrumentation amplifier 10 at mixer amplifier 14 to produce noisy modulated input signal 25. Noisy modulated input signal 25 includes the original low frequency components modulated up to the carrier frequency and noise components at baseband.

As previously described, mixer amplifier 14 may be implemented using the modified folded-cascode amplifier architecture illustrated in FIG. 6. Reference and bias generator 94 supplies bias and reference voltages to mixer amplifier 14. In the interest of simplicity, mixer amplifier 14 is illustrated in FIG. 7 as including amplifier 84, demodulator 86, and integrator 88, which correspond to amplifier 26, demodulator 28, and integrator 30 in FIG. 2. Accordingly, amplifier 84 amplifies noisy modulated input signal 25 and demodulator 86 demodulates amplified signal 27. More specifically, demodulator 86 demodulates the original low frequency signal components of the amplified signal back down to baseband and modulates noise 23 up to the carrier frequency, thereby maintaining separation between the desired signal and noise. Clock 96 supplies a clock signal to drive demodulator 86. For example, with respect to the circuit diagram of FIG. 6, clock 96 supplies a clock signal to drive switches 60 and 62 which operate as demodulator 86. Integrator 88 integrates demodulated signal 29 with respect to a reference voltage supplied by reference and bias generator 94 and acts as a low pass filter that substantially eliminates signal components with a frequency outside of the baseband. Consequently, noise sitting at the carrier frequency of demodulated signal 29 is substantially eliminated from the output of integrator 88, i.e., output signal 31.

In FIG. 7, feedback 16 includes negative feedback path 90, negative feedback path 92, and positive feedback path 98. To provide a differential-to-single conversion, each of feedback paths 90, 92, and 98 may include two symmetrical feedback path branches to provide feedback to respective positive and negative differential inputs of mixer amplifier 14. In particular, negative feedback path 90 provides negative feedback at the input to mixer amplifier 14 to keep the signal change small. Each of the feedback path branches of negative feedback path 90 modulates output signal 31 with a reference voltage provided by reference and bias generator 94. To ensure that a negative feedback path exists in negative feedback path 90 at all times, the chop frequency applied to the negative feedback path branches of feedback path 90 should be 180 degrees out of phase with each other with one of the feedback paths synchronous with front end 12. In this way, one of the feedback path branches of negative feedback path 90 is applying negative feedback during each half of the clock cycle. As a result, the differential signals at the input of mixer amplifier 14 are small and centered about the reference voltage. Negative feedback 90 substantially eliminates the dynamic limitation of instrumentation amplifier 10, i.e., glitching in output signal 31.

Negative feedback path 92 allows for the construction of a high pass filter. In particular, negative feedback path 92 integrates the output of instrumentation amplifier 10, i.e., output signal 31, with respect to a reference voltage supplied by reference and bias generator 94 and applies the integrated signal to the inputs of mixer amplifier 14 through a capacitor. Each of the feedback path branches of negative feedback path 92 modulates the integrated output signal with the reference voltage. Similar to the previously described feedback paths of negative feedback path 90, relative phasing of feedback path branches of negative feedback path 92 should ensure that a negative feedback path exists for each half of the clock cycle. In operation, negative feedback path 92 is dominant at low frequency and suppresses the DC response of instrumentation amplifier 10. However, negative feedback path 90 is dominant at passband frequencies. The scaling of feedback capacitors in feedback path 90 and the time constant of feedback path 92 set the high pass corner of the filter. In other words, capacitors in feedback paths 90 and 92 are used to set the high pass corner.

As an example, a high pass filter may be useful for rejecting post-pacing artifacts when instrumentation amplifier 10 is used for heart monitoring applications and filtering out electrode offsets when instrumentation amplifier is used for monitoring brain signals. As an example, feedback path 92 may be used to construct a high pass filter with a cutoff frequency equal to approximately 2.5 Hz, 0.5 Hz, or 0.05 Hz. In this case, feedback path 92 may be dominant at frequencies below cutoff frequencies of 2.5 Hz, 0.5 Hz, or 0.05 Hz, while feedback path 90 may be dominant at frequencies above the cutoff frequencies. In one example, feedback path 92 may have a cutoff frequency of approximately 0.5 Hz, permitting feedback path 90 to dominate at frequencies above approximately 0.5 Hz, e.g., approximately 5 Hz to 100 Hz Positive feedback path 98 increases the input impedance of instrumentation amplifier 10. More specifically, positive feedback path 98 samples output signal 31 and provides feedback to front end 12 before chopper modulation is applied to the input signal. The positive feedback effectively "replaces charge" on the input capacitors to mixer amplifier 14 that is lost during the sampling process. Positive feedback path 98 may increase the input impedance of instrumentation amplifier 10 by an order of magnitude or more. Each feedback path branch of positive feedback path 98 may include a switched capacitor arrangement to add compensatory charge to the input capacitors.

Although FIG. 7 depicts feedback path 16 as including negative feedback path 90, negative feedback path 92, and positive feedback path 98, only negative feedback path 90 may be provided for instrumentation amplifier 10 to achieve stable measurements at low frequency with very low power. Accordingly, feedback paths 92, 98 may be considered optional, auxiliary feedback paths that enable instrumentation amplifier 10 to achieve additional performance enhancements. Consequently, various example embodiments of the invention described in this disclosure may include one, both, or neither of feedback paths 92, 98. When the instrumentation amplifier includes feedback paths 92 and 98, positive feedback path 98 may sample the integrated output signal from negative feedback path 92 instead of sampling the output signal of mixer amplifier 14. The relative arrangement of feedback paths 90, 92, 98 may be more apparent from the circuit diagrams that follow in the additional figures.

In some embodiments, clock 96 may comprise one or more clocks. For example, when instrumentation amplifier 10 is implanted on a single chip, a single clock may supply clock signals to front end 12, mixer amplifier 14, and feedback path 16. However, in some embodiments, such as when instrumentation amplifier 10 is used to demodulate telemetry signals, front end 12 may be implemented on a separate chip than mixer amplifier 14 and feedback 16. In this case, front end 12 may be supplied with a clock signal from one clock while a different clock provides clock signals to mixer amplifier 14 and feedback 16. In this case, the two clocks may not be in phase with each other. Since the clocks should be in phase with each other to ensure that the transmitted signal can be recovered, additional circuitry may be required at the receiver to synchronize the clocks.

Reference and bias generator 94 supplies bias voltages to front end 12, mixer amplifier 14, negative feedback path 90, and negative feedback path 92. When front end 12 includes a physiological sensor, reference and bias generator 94 may supply reference voltages that drive the physiological sensor. Reference and bias generator 94 may also supply the reference voltages to electrodes for an impedance sensor. With respect to mixer amplifier 14, reference and bias generator 94 may supply bias voltages for biasing the transistors as shown in FIG. 6. The reference voltages that are mixed with the signals in feedback paths 90 and 92 as previously described may also be supplied by reference and bias generator 94. Bias voltages of 0 volts to 1.2 volts (bandgap) or 0 volts to 0.6 volts (half bandgap) may be used as bias points.

Figure 8:
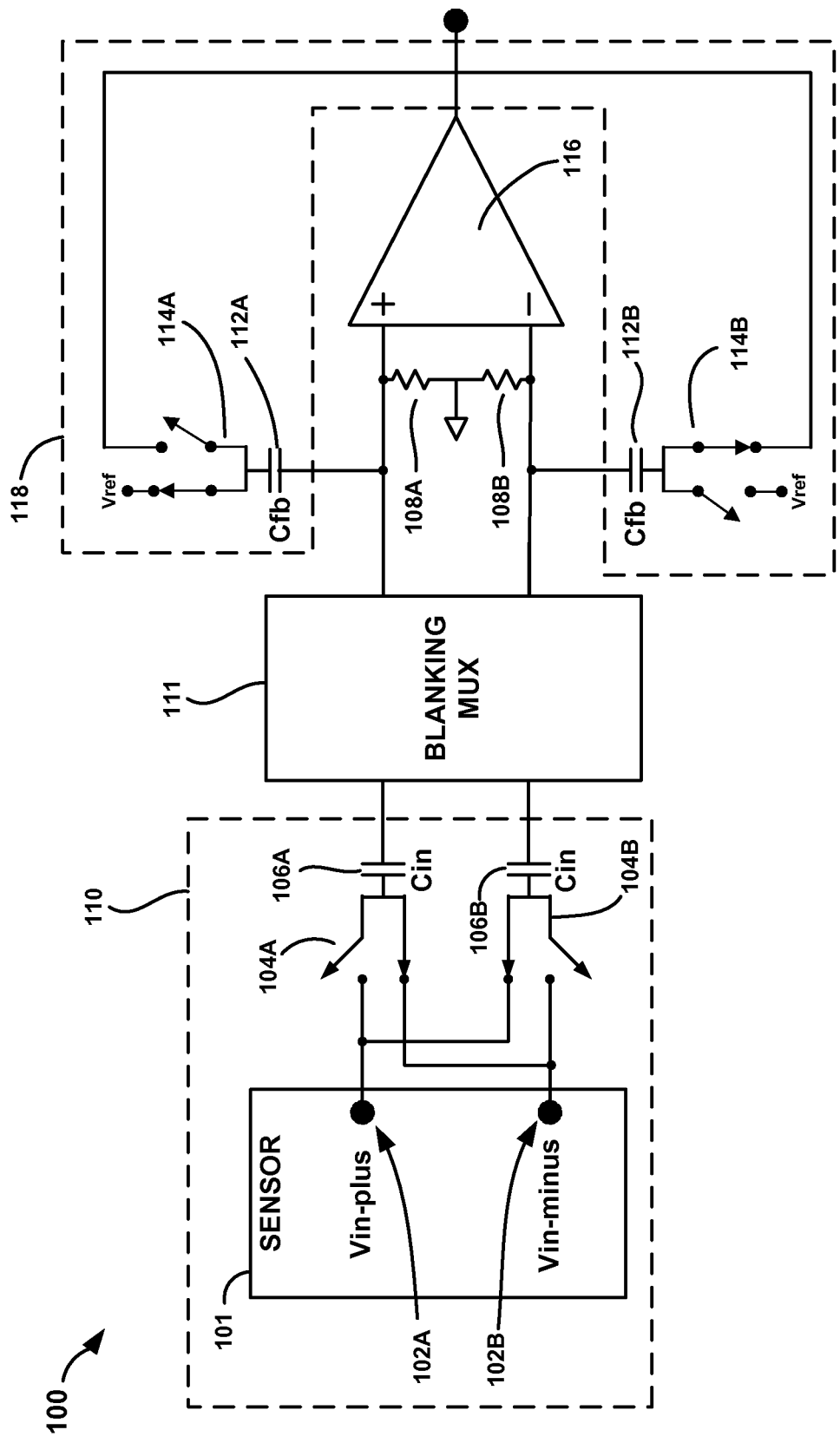
FIG. 8 is a circuit diagram illustrating an example embodiment of the instrumentation amplifier of FIG. 1 for measurement of voltage signals.

FIG. 8 is a circuit diagram illustrating an instrumentation amplifier 100. Instrumentation amplifier 100 is an example embodiment of instrumentation amplifier 10 previously described in this disclosure. In FIG. 8, instrumentation amplifier 100 includes sensor 101 which generates a differential voltage across its outputs 102A and 102B (collectively referred to as "outputs 102"). Outputs 102A and 102B provide voltages Vin-plus and Vin-minus, respectively. Sensor 101 may be a physiological sensor that translates biophysical signals to a differential electrical voltage across outputs 102. For example, sensor 101 may be an accelerometer, a pressure sensor, a force sensor, a gyroscope, a humidity sensor, a pair of electrodes, or the like.

Inputs 102A and 102B are connected to capacitors 106A and 106B (collectively referred to as "capacitors 106") through switches 104A and 104B (collectively referred to as "switches 104"), respectively. Switches 104 are driven by a clock signal provided by a system clock (not shown) and are cross-coupled to each other to reject common-mode signals. Capacitors 106 are coupled at one end to a corresponding one of switches 104 and to a corresponding input of mixer amplifier 116 at the other end. In particular, capacitor 106A is coupled to the positive input of mixer amplifier 116, and capacitor 106B is coupled to the negative input of amplifier 116, providing a differential input.

In FIG. 8, sensor 101, switches 104, and capacitors 106 form front end 110. Front end 110 generally corresponds to front end 12 of instrumentation amplifier 10. In particular, front end 110 operates as a continuous time switched capacitor network as previously described with respect to front end 12. Switches 104 toggle between an open state and a closed state in which inputs 102 are coupled to capacitors 106 at a clock frequency to modulate (chop) the output of sensor 101 to the carrier (clock) frequency. As previously described, the output of sensor 101 may be a low frequency signal within a range of approximately 0 Hz to approximately 100 Hz. The carrier frequency may be within a range of approximately 4 kHz to approximately 10 kHz. Hence, the low frequency sensor output is chopped to the higher chop frequency band.

Switches 104 toggle in-phase with one another to provide a differential input signal to mixer amplifier 116. During a first phase of the clock signal, switch 104A connects sensor output 102B to capacitor 106A and switch 104B connects sensor output 102A to capacitor 106B. During a second phase, switches 104 change state such that switch 104A couples port 102A to capacitor 106A and switch 104B couples port 102B to capacitor 106B. Switches 104 synchronously alternate between the first and second phases to modulate the differential voltage at outputs 102 at the carrier frequency. The resulting chopped differential signal is applied across capacitors 106, which couple the differential signal across the inputs of mixer amplifier 116.

Resistors 108A and 108B (collectively referred to as "resistors 108") provide a DC conduction path that controls the voltage bias at the input of mixer amplifier 116. In other words, resistors 108 may be selected to provide an equivalent resistance that is used to keep the bias impedance high. Resistors 108 may, for example, be selected to provide a 5 GΩ equivalent resistor, but the absolute size of the equivalent resistor is not critical to the performance of instrumentation amplifier 100. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF. In light of this, a stronger motivation for keeping the impedance high is the rejection of high frequency harmonics which can alias into the signal chain due to settling at the input nodes of mixer amplifier 116 during each half of a clock cycle.

It is important to note that resistors 108 are merely exemplary and serve to illustrate one of many different biasing schemes for controlling the signal input to mixer amplifier 116. In fact, the biasing scheme is flexible because the absolute value of the resulting equivalent resistance is not critical. In general, the time constant of resistor 108 and input capacitor 106 may be selected to be approximately 100 times longer than the reciprocal of the chopping frequency.

Mixer amplifier 116 may produce noise and offset in the differential signal applied to its inputs. For this reason, the differential input signal is chopped via switches 104A, 104B and capacitors 106A, 106B to place the signal of interest in a different frequency band from the noise and offset. Then, mixer amplifier 116 chops the amplified signal a second time to demodulate the signal of interest down to baseband while modulating the noise and offset up to the chop frequency band. In this manner, instrumentation amplifier 100 maintains substantial separation between the noise and offset and the signal of interest. Mixer amplifier 116 and feedback path 118 process the noisy modulated input signal to achieve a stable measurement of the low frequency signal output by sensor 101 while operating at low power.

As previously described, operating at low power tends to limit the bandwidth of mixer amplifier 116 and creates distortion (ripple) in the output signal. Mixer amplifier 116 and feedback path 118 correspond to and, thus, operate in a manner similar to previously described mixer amplifier 14 and feedback path 16. More specifically, feedback path 118 corresponds to negative feedback path 90 described in FIG. 7 Mixer amplifier 116 and feedback path 118 substantially eliminate the dynamic limitations of chopper stabilization through a combination of chopping at low-impedance nodes and AC feedback, respectively.

In FIG. 8, mixer amplifier 116 is represented with the circuit symbol for an amplifier in the interest of simplicity. However, it should be understood that mixer amplifier 116 may be implemented in accordance with the circuit diagram provided in FIG. 6. Consequently, mixer amplifier 116 provides synchronous demodulation with respect to front end 12 and substantially eliminates 1/f noise, popcorn noise, and offset from the signal to output a signal that is an amplified representation of the differential voltage produced by sensor 101.

Without the negative feedback provided by feedback path 118, the output of mixer amplifier 116 would include spikes superimposed on the desired signal because of the limited bandwidth of the amplifier at low power. However, the negative feedback provided by feedback path 118 suppresses these spikes so that the output of instrumentation amplifier 100 in steady state is an amplified representation of the differential voltage produced by sensor 101 with very little noise.

Feedback path 118 in FIG. 8 may include two feedback paths that provide a differential-to-single ended interface. The top feedback path branch modulates the output of mixer amplifier 116 to provide negative feedback to the positive input terminal of mixer amplifier 116. The feedback path branch includes capacitor 112A and switch 114A. Similarly, the bottom feedback path branch of feedback path 118 includes capacitor 112B and switch 114B that modulate the output of mixer amplifier 116 to provide negative feedback to the negative input terminal of mixer amplifier 116. Capacitors 112A and 112B are connected at one end to switches 114A and 114B, and at the other end to the positive and negative input terminals of mixer amplifier 116, respectively.

Switches 114A and 114B toggle between a reference voltage (Vref) and the output of mixer amplifier 116 to place a charge on capacitors 112A and 112B, respectively. The reference voltage may be, for example, a mid-rail voltage between a maximum rail voltage of amplifier 116 and ground. For example, if the amplifier circuit is powered with a source of 0 to 2 volts, then the mid-rail Vref voltage may be on the order of 1 volt. Importantly, switches 114A and 114B should be 180 degrees out of phase with each other to ensure that a negative feedback path exists during each half of the clock cycle. One of switches 114 should also be synchronized with mixer amplifier 116 so that the negative feedback suppresses the amplitude of the input signal to mixer amplifier 116 to keep the signal change small in steady state. By keeping the signal change small and switching at low impedance nodes of mixer amplifier 116, e.g., as shown in the circuit diagram of FIG. 6, the only significant voltage transitions occur at switching nodes. Consequently, glitching (ripples) is substantially eliminated or reduced at the output of mixer amplifier 116.

Switches 104 and 114, as well as the switches at low impedance nodes of mixer amplifier 116, may be CMOS SPDT switches. CMOS switches provide fast switching dynamics that enables switching to be viewed as a continuous process. The transfer function of instrumentation amplifier 100 may be defined by the transfer function provided in equation (1) below, where Vout is the voltage of the output of mixer amplifier 116, Cin is the capacitance of input capacitors 106, ΔVin is the differential voltage at the inputs to mixer amplifier 116, Cfb is the capacitance of feedback capacitors 112, and Vref is the reference voltage that switches 114 mix with the output of mixer amplifier 116.

$$V\text{out}=C\text{in}(\Delta V\text{in})/C\text{fb}+V\text{ref} \quad (1)$$

From equation (1), it is clear that the gain of instrumentation amplifier 100 is set by the ratio of input capacitors Cin and feedback capacitors Cfb, i.e., capacitors 106 and capacitors 112. The ratio of Cin/Cfb may be selected to be on the order of 100. Capacitors 112 may be poly-poly, on-chip capacitors or other types of MOS capacitors and should be well matched, i.e., symmetrical.

Although not shown in FIG. 8, instrumentation amplifier 100 may include shunt feedback paths for auto-zeroing amplifier 100. The shunt feedback paths may be used to quickly reset amplifier 100. An emergency recharge switch also may be provided to shunt the biasing node to help reset the amplifier quickly. The function of input capacitors 106 is to up-modulate the low-frequency differential voltage from sensor 101 and reject common-mode signals. As discussed above, to achieve up-modulation, the differential inputs are connected to sensing capacitors 106A, 106B through SPDT switches 104. The phasing of the switches provides for a differential input to the ac transconductance mixing amplifier 116. These switches 104 operate at the clock frequency, e.g., 4 kHz. Because the sensing capacitors 106 toggle between the two inputs, the differential voltage is up-modulated to the carrier frequency while the low-frequency common-mode signals are suppressed by a zero in the charge transfer function. The rejection of higher-bandwidth common signals relies on this differential architecture and good matching of the capacitors.

As further shown in FIG. 8, for applications in which measurements are taken in conjunction with stimulation pulses delivered by a cardiac pacemaker, cardiac defibrillator, or neurostimulator, blanking circuitry may be added to instrumentation amplifier 100 the inputs of mixer amplifier 116 and coupling capacitors 106 to ensure that the input signal settles before reconnecting mixer amplifier 116 to front end 110. For example, the blanking circuitry may be a blanking multiplexer (MUX) 111 that selectively couples and de-couples mixer amplifier 116 from front end 110. This blanking circuitry selectively decouples the mixer amplifier from the differential input signal and selectively disables the first and second modulators, i.e., switches 104, 114, e.g., during delivery of a stimulation pulse.

Blanking MUX 111 is optional but may be desirable. The clocks driving switches 104, 114 to function as modulators cannot be simply shut off because the residual offset voltage on mixer amplifier 116 would saturate the amplifier in a few milliseconds. For this reason, blanking MUX 111 may be provided to decouple amplifier 116 from the input signal for a specified period of time during and following application of a stimulation by a cardiac pacemaker or defibrillator, or by a neurostimulator.

To achieve suitable blanking, the input and feedback switches 104, 114 should be disabled while mixer amplifier 116 continues to demodulate the input signal. This holds the state of the integrator within mixer amplifier 116 because the modulated signal is not present at the inputs of the integrator, while the demodulator continues to chop the DC offsets. Accordingly, blanking MUX 111 may further include circuitry or be associated with circuitry configured to selectively disable switches 104, 114 during a blanking interval. Post blanking, mixer amplifier 116 may require additional time to resettle because some perturbations may remain. Thus, the total blanking time includes time for demodulating the input signal while the input and switches 104, 114 are disabled and time for settling of any remaining perturbations. An example blanking time following application of a stimulation pulse may be approximately 8 ms with 5 ms for mixer amplifier 116 and 3 ms for the AC coupling components.

Figure 9:
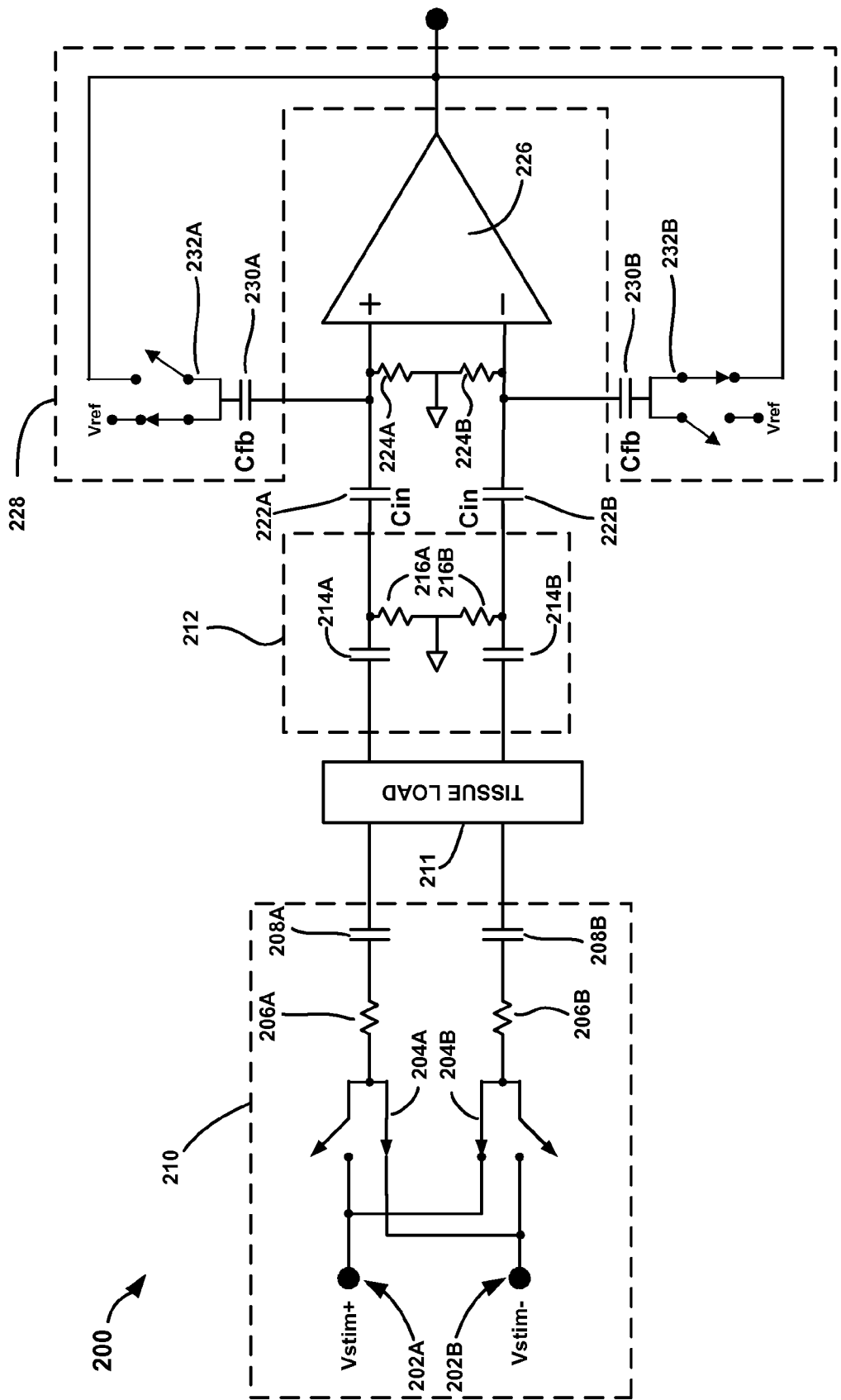
FIG. 9 is a circuit diagram illustrating another example embodiment of the instrumentation amplifier of FIG. 1 for measurement of impedance.

FIG. 9 is a circuit diagram illustrating an instrumentation amplifier 200 for measuring impedance across a tissue load 211. Tissue load 211 represents the tissue of a patient for which impedance is measured by instrumentation amplifier 200. Tissue 211 may be organ tissue, such as heart tissue, lung tissue, or brain tissue, muscle tissue, adipose tissue, or other tissue for which the impedance may be measured to diagnose chronic or acute disease states or other medical conditions. Some example applications for impedance measurements include detection of pulmonary edema, minute ventilation measurements for respiration, measurement of cardiac dynamics, and measurement of brain signals. In general, it is important that instrumentation amplifier 200 does not stimulate excitable cells in the tissue or cause other detrimental effects such as electrode corrosion.

Instrumentation amplifier 200 may generally conform to instrumentation amplifier 10 described with reference to FIGS. 1-7. In the example of FIG. 9, instrumentation amplifier 200 applies synchronous detection principles to accurately measure the impedance of tissue load 211 with low power, inherent charge balancing, rejection of electrode potentials, and small stimulation currents. Instrumentation amplifier 200 is an example embodiment of previously described instrumentation amplifier 10. Like instrumentation amplifier 10, instrumentation amplifier 200 includes a front end 210, mixer amplifier 226, and feedback path 228. These features may generally correspond to front end 12, mixer amplifier 14, and feedback path 16 of instrumentation amplifier 10.

In FIG. 9, front end 210 includes input voltages at ports 202A and 202B (collectively referred to as "ports 202"), switches 204A and 204B (collectively referred to as "switches 204"), resistors 206A and 206B (collectively referred to as "resistors 206"), and capacitors 208A and 208B (collectively referred to as "capacitors 208"). In general, front end 210 modulates a stimulation current that creates a voltage on tissue load 211. The stimulation current may be applied across tissue load 211 via two or more electrodes, which may be mounted on one or more leads or carried on a surface of an implantable medical device housing. Similarly, the resulting voltage signal across tissue load 211 may be sensed by two or more electrodes deployed on one or more leads or on a device housing. The voltage on tissue load 211 is AC coupled to positive and negative inputs of mixer amplifier 226 by capacitors 222A and 222B (collectively referred to as "capacitors 222"), respectively. Thus, the tissue represented by tissue load 211 is not exposed to DC current. Moreover, the small modulated (AC) stimulation current, which may be approximately 10 μA or less, may not substantially excite the tissue represented by tissue load 211.

Switches 204 toggle between input voltages at ports 202 (Vstim+ and Vstim−) to generate stimulation current through resistor-capacitor (RC) pairs of resistor 206A and capacitor 208A and resistor 206B and capacitor 208B. Switches 204, resistors 206 and capacitors 208 may form an alternating current (ac) source that generates an ac stimulation current at a clock frequency for application to a load, such as 211. In particular, switches 204, resistors 206 and capacitors 208 form a modulator that modulates first and second voltages Vstim+ and Vstim− at the clock frequency to produce the stimulation current for application to the load. However, other types of ac current sources may be use to provide the ac stimulation current for impedance measurement.

The input voltages Vstim+ and Vstim− may be provided by regulated power supplies within a device in which instrumentation amplifier 200 is employed, such as an implantable medical device. Switches 204 open and close at a chopper frequency to, in effect, chop the input stimulation current delivered by input voltages at ports 202 via the RC pairs (206, 208) to measure tissue impedance. In this manner, front end 210 generates a modulated differential input signal that is processed by mixer amplifier 226 and feedback path 228. Stimulation currents at ports 202 may be provided by electrodes carried on leads that are connected to an IPG implanted within a patient. This is one example of delivery of stimulation current for impedance measurements. As an alternative, stimulation current for impedance measurement could be generated by one or more switched current sources. The reference voltages at ports 202 and the sizes of resistors 206 and capacitors 208 may be determined by the constraints on the stimulation current, linearity of the measurement, and the time constant of instrumentation amplifier 200 compared to the clock (not shown) that drives switches 204.

As an example, using a stimulation current of 10 μA, voltages at ports 202A and 202B may provide 2V and 0V, respectively, and resistors 206 may be selected as 100 kΩ resistors. Alternatively, using 2000 kΩ resistors yields a 0.5 μA stimulation current with 100 kΩ resistors. Using 10 nF capacitors for capacitors 208 results in a stimulation current having a time constant of 1 ms, which requires a stimulation current with a frequency of approximately 5 kHz to ensure minimal error from settling dynamics. The nonlinearity of the measurement, assuming 1 kHz loads, is bounded to under 0.5% in this case.

The input to mixer amplifier 226 may include a high pass filter 212 and coupling capacitors 222A, 222B. In some embodiments, high pass filter 212 assists in keeping postpace recovery to a minimum for cardiac dynamic measurements. In FIG. 9, high pass filter 212 includes capacitors 214A, 214B (collectively referred to as "capacitors 214") and resistors 216A, 216B (collectively referred to as "resistors 216"). The values of capacitors 214 and resistors 216 may be selected such that high pass filter 212 has a high pass corner frequency that ensures minimal phase error, e.g., less than 1% equivalent measurement error, occurs at mixer amplifier 226 while settling any residual pacing errors in 2.5 ms to 5 time constants. For some applications, such as cardiac impedance analysis, the high pass corner frequency may, for example, be within a range of approximately 300 Hz to approximately 800 Hz.

Resistors 224A and 224B (collectively referred to as "resistors 224") control the voltage at the input of mixer amplifier 226. Accordingly, resistors 224 are similar to resistors 108 in FIG. 7 and are merely exemplary. As previously described, resistors 224 or a different bias scheme may be selected to provide a 5 GΩ equivalent resistor although the absolute value is not critical.

Mixer amplifier 226 and feedback path 228 process the noisy modulated input signal to achieve a stable measurement of the differential voltage on tissue load 211 while operating at low power. Mixer amplifier 226 and feedback path 228 generally correspond to mixer amplifier 116 and feedback path 118 in FIG. 7. Accordingly, mixer amplifier 226 provides synchronous demodulation with respect to front end 12 and substantially eliminates noise, i.e., 1/f noise, popcorn noise, and offset, from the amplified output signal. Mixer amplifier 226 may be implemented using the modified folded-cascode architecture with switching at low impedance nodes, e.g., substantially as shown in FIG. 6.

As shown in FIG. 9, feedback path 228 includes top and bottom feedback path branches that provide negative feedback and a single-to-differential interface. The top and bottom feedback path branches include capacitors 230A and 230B (collectively referred to as "capacitors 230") which are connected to switches 232A and 232B (collectively referred to as "switches 232"), respectively. Switches 232A and 232B are 180 degrees out of phase with each other and toggle between the output of mixer amplifier 226 and a reference voltage (Vref) to modulate the output of mixer amplifier 226. Consequently, feedback path 218 provides negative feedback to keep the signal change at the input to mixer amplifier 226 small as previously described in this disclosure.

Switches 206, switches 232, and the switches at low impedance nodes in mixer amplifier 226 may be CMOS SPDT switches or other switches that provide fast switching dynamics. The transfer function for instrumentation amplifier 200 is the same as that for instrumentation amplifier 100, which is provided in the above description of FIGS. 7 and 8. Thus, the ratio of the capacitance of feedback capacitors, i.e., capacitors 230, to the capacitance of input capacitors, i.e., capacitors 222, sets the gain of instrumentation amplifier 226. Capacitors 222 and 230 may be poly-poly capacitors or other types of MOS capacitors and should be well matched, i.e., symmetrical. Capacitors 222 and 230 may be placed on chip with the other instrumentation amplifier components.

In operation, instrumentation amplifier 200 may fold electromagnetic interference (EMI) into the modulated input signal at the carrier frequency and odd harmonics. In order to determine if the channel is corrupt, the output of instrumentation amplifier 200 can be monitored with no stimulation current applied to front end 210. Alternatively, spread-spectrum techniques may be used to break up the synchronous clock detection between front end 210 and mixer amplifier 226. Spread-spectrum clocking breaks up the uncorrelated noise into a broadband noise signal that is substantially eliminated by mixer amplifier 226, while maintaining the correlated impedance measurement.

The output of instrumentation amplifier 200 may be sent to an analog-to-digital converter (ADC) (not shown) that applies additional processing for measuring the impedance of tissue load 211. Further, when instrumentation amplifier 200 is implanted within a patient, the tissue-electrode interface (front end 12) may be galvanically isolated from the measurement circuit (mixer amplifier 226 and feedback path 228). Isolation helps to reject electrode polarization and ensure net charge balance across the electrodes.

Instrumentation amplifier 200 can be used to separate the measurement of lead impedances from impedance measurements for edema, minute ventilation, and cardiac dynamics. The reason for this is that the requirements are different for the two measurements. Lead impedances ordinarily require a quick sample to be taken just prior to delivery of a pacing or stimulation pulse, with several vectors requiring measurement. Perturbation of the sensing channel is not a major issue since the stimulation pulse immediately follows the measurement. This favors the application of large, fast, sampled stimulation current. The measurement of edema, minute ventilation and cardiac dynamics, however, occur at low frequency where the sensing channel should be free of perturbations and noise. Significant perturbations from this measurement, i.e., measurement of lead impedances, compromises the ability of the sense channel to accurately detect evoked potentials post-pace and can result in oversensing. Edema, minute ventilation and cardiac dynamic measurements therefore favor low level stimuli, averaged with continuous time methods. Instrumentation amplifier 200 enables edema, minute ventilation and cardiac dynamic measurements to be separate from measurement of lead impedances.

Although not shown in FIG. 9, for applications in which measurements are taken in conjunction with stimulation pulses delivered by a cardiac pacemaker or neurostimulator, blanking circuitry such as the blanking MUX 111 shown in FIG. 8 may be added to instrumentation amplifier 200. For example, a blanking MUX may disconnect input capacitors 222 from the inputs of mixer amplifier 226. In addition, input and feedback modulators may be disabled during the blanking period. In some embodiments, the blanking MUX may be placed between high pass filter 212 and coupling capacitors 222 to ensure that the input signal settles before reconnecting mixer amplifier 226 to front end 210. Hence, the blanking circuitry may be a multiplexer (MUX) that selectively couples and de-couples mixer amplifier 226 from front end 210. As mentioned with reference to FIG. 8, blanking circuitry may be desirable because the clocks driving the switches cannot be simply shut off since the residual offset voltage on mixer amplifier 226 would saturate the amplifier in a few milliseconds.

To achieve suitable blanking, the input and feedback switches 222, 232, should be disabled while mixer amplifier 226 continues to demodulate the input signal. This holds the state of the integrator within mixer amplifier 226 because the modulated signal is not present at the inputs of the integrator, while the demodulator continues to chop the DC offsets. Post blanking, mixer amplifier 226 may require additional time to resettle because some perturbations may remain. Thus, the total blanking time includes time for demodulating the input signal while the input and feedback switches are disabled and time for settling of any remaining perturbations. An example blanking time may be approximately 8 ms with 5 ms for mixer amplifier 226 and 3 ms for the AC coupling components.

Through experimentation, it has been found that the linearity of measurement via instrumentation amplifier 200 meets a theoretical limit of 0.05% for a 500 nA stimulation current and 1.5% for a 10 μA stimulation current. The worst-case linearity is at high impedance, due to finite output impedance of mixer amplifier 226. In other words, higher stimulation currents result in greater non-linearity. In practice, the observable nonlinearity is small for reasonable stimulation vectors through a tissue load on the order of 1 kΩ.

Experimentation has also shown the measured noise floor of an instrumentation amplifier including a mixer amplifier and negative feedback, such as instrumentation amplifier 100 and 200, to be approximately 100 nV/rt Hz. This is in line with theoretical expectations form Johnson noise in the input transistors of the mixer amplifier 226 operating with 1 μA of stimulation current. For a 10 μA stimulation current, this translates into an equivalent noise floor of 0.01 ohms/rtHz, which is well below the requirements in many physiological applications.

Figure 10:
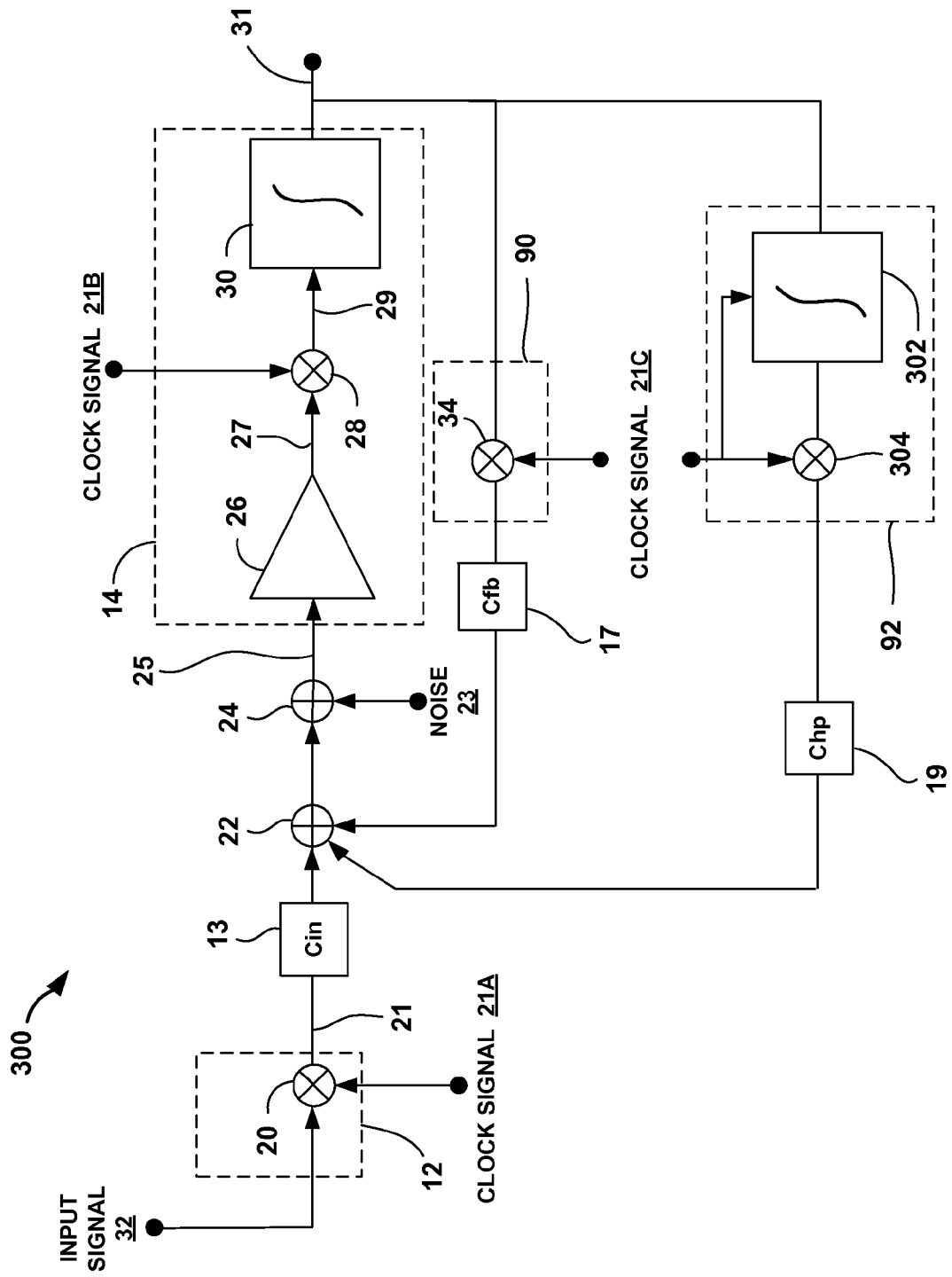
FIG. 10 is a diagram illustrating a signal path flow for an instrumentation amplifier in accordance with an embodiment of the invention that includes a negative feedback path for constructing a high pass filter.

FIG. 10 is a diagram illustrating an example signal flow for an instrumentation amplifier 300 that includes negative feedback for constructing a high pass filter. With respect to FIG. 2, the architecture of instrumentation amplifier 300 in FIG. 10 may be substantially the same as that of instrumentation amplifier 10, but with the addition of negative feedback path 92. Accordingly, similar number components in FIG. 2 and FIG. 10 share similar functionality. In the interest of brevity and to avoid redundancy, the signal flow through front end 10, mixer amplifier 14 and feedback path 90 is not described in detail. Instead, the flow of output signal 31 which is produced by mixer amplifier 14 through negative feedback path 92 is described.

In general, negative feedback path 92 performs additional signal processing on output signal 31 to construct a high pass filter at the input to mixer amplifier 14. The high pass filter substantially eliminates signal components that have a frequency below the corner frequency of the high pass filter. For example, feedback path 92 may set a corner frequency of approximately equal to 2.5 Hz, 0.5 Hz, or 0.05 Hz. In general, negative feedback path 92 suppresses signals between the corner frequency and DC. As previously described, feedback path 92 provides differential feedback to respective input terminals of mixer amplifier 14 through symmetrical feedback paths. The feedback paths should be 180 degrees out of phase with each other so that negative feedback is applied during each half cycle of the clock cycle.

As shown in FIG. 10, negative feedback path 92 includes an integrator 302 and modulator 304. Integrator 302 integrates output signal 31 with respect to a reference voltage. This reference voltage should be the same reference voltage that is modulated with the signal in instrumentation amplifier 300 by modulators 20, 28, and 34. In some embodiments, a switched capacitor integrator may be used for integrator 302. In other embodiments, a standard RC integrator may be used. The switched capacitor integrator may, however, provide certain advantages.

Modulator 304 modulates the output of integrator 302 to provide a differential voltage into mixer amplifier 14. Since modulator 304 should be synchronized with feedback path 90, clock signal 21C also drives modulator 304. Clock signal 21C is also supplied to integrator 302, as shown in FIG. 10, when integrator 302 is implemented as a switched capacitor integrator. Also shown in FIG. 10 are input capacitance (Cin) 13, feedback capacitance (Cfb) 17 for feedback path 90, high pass filter capacitance (Chp) 10 for feedback path 92.

In operation, integrator 302 produces a voltage on the switched capacitor of modulator 304 that counters the charge on the switched capacitor of modulator 34. When an input step is applied to mixer amplifier 14, the signal is integrated by integrator 30. Initially, the voltage difference between demodulated signal 29 and the reference voltage of integrator 30 is relatively large. In contrast, the difference between the voltage of output signal 31 and the reference voltage for integrator 302 is relatively small. As a result, integrator 30 builds up charge on the switched capacitor of modulator 34 more quickly than integrator 302 builds up charge on the switched capacitor of modulator 304.

Over time, however, the voltage difference between demodulated signal 29 and the reference voltage at integrator 30 decreases and integrator does not build up as much charge. At the same time, the voltage difference between output signal 31 and the reference voltage at integrator 302 increases and integrator 302 builds up more charge on the switched capacitor at modulator 304. Thus, in steady state, feedback path 92 dominates feedback path 90 and the feedback counter charge is mostly provided via negative feedback path 92. As a result, feedback path 92 can set the high pass corner through a ratio of capacitors 17 and 19 (Cfb and Chp) and a time constant set by the capacitors and clock frequency of integrator 302. Importantly, since instrumentation amplifier 300 may be implemented entirely on a single chip, off chip capacitors may not be needed for high pass filtering.

Figure 11:
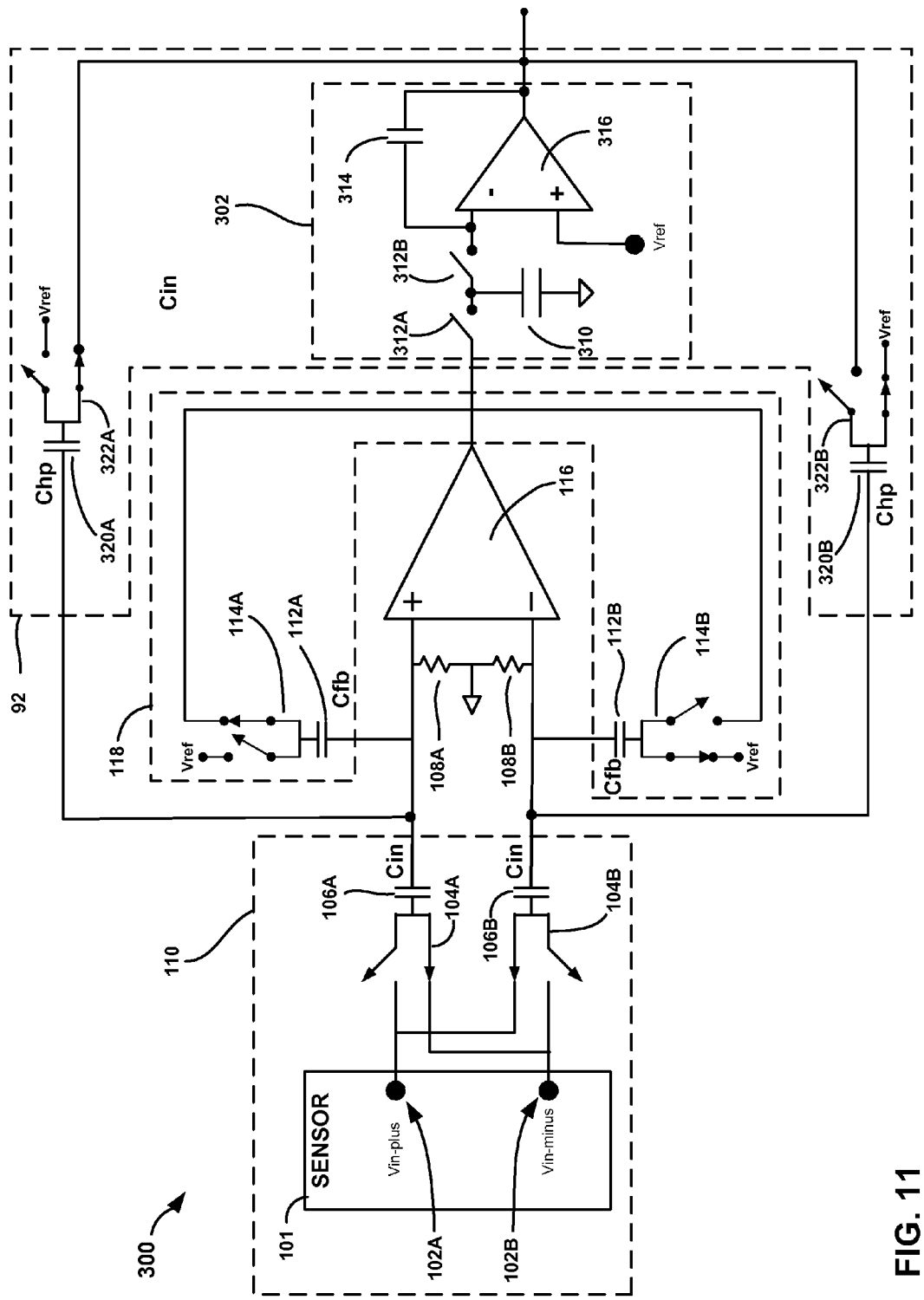
FIG. 11 is a circuit diagram illustrating the instrumentation amplifier of FIG. 10.

FIG. 11 is a circuit diagram illustrating instrumentation amplifier 300. As shown in FIG. 11, the architecture of instrumentation amplifier 300 is substantially the same as that of instrumentation amplifier 100, but with the addition of negative feedback path 92. Accordingly, similar number components in FIG. 7 and FIG. 10 share the same functionality. The operation of these shared components is not described in the interest of brevity and to avoid redundancy. However, the operation of feedback path 92 is described.

Negative feedback path 92 taps off of the output of mixer amplifier 116 and applies negative feedback to the inputs of mixer amplifier 116. In the example of FIG. 11, integrator 302 is a switched capacitor integrator. Integrator 302 may be in addition to the integrator and demodulator provided within mixer amplifier 116. The switched capacitor integrator includes a capacitor 310 coupled between the output of amplifier 116 and ground via switch 312A, and between the negative input of amplifier 316 and ground via switch 312B. Switch 312A and 312B toggle at the chop frequency, but are out of phase with one another. The clocking frequency of switches 312A and 312B can be adjusted to set the time constant of integrator 302. The positive terminal of amplifier 316 is coupled to a reference voltage (Vref), which may be the same reference voltage that is mixed with the signal at other stages in instrumentation amplifier 300. Capacitor 314 couples the output of amplifier 316 to the negative terminal of amplifier 316.

The two feedback paths of feedback path 92 tap off of the output of integrator 302 to provide negative feedback to mixer amplifier 116. In particular, the top feedback path branch modulates the output of integrator 302 to provide negative feedback to the positive terminal of mixer amplifier 116. The top feedback path branch includes capacitor 320A and switch 322A. Similarly, the bottom feedback path branch of feedback path 92 includes capacitor 320B and switch 322B, which modulate the output of integrator 302 to provide negative feedback to the negative terminal of mixer amplifier 116.

Capacitors 320A and 320B are connected at one end to switches 322A and 322B, and to the positive and negative input terminals of mixer amplifier 116 at the other end, respectively. Switches 322A and 322B toggle between a reference voltage (Vref) and the output of mixer integrator 302 to place a charge on capacitors 320A and 320B, respectively. Switch 322A and 322B toggle 180 degrees out of phase with one another. Importantly, switches 322A and 322B should be synchronized with switches 114A and 114B, respectively. In this way, a negative feedback path exists during each half cycle of the clock signal and is synchronized with the negative feedback path.

As previously described in FIG. 10, integrator 302 builds up a voltage that is placed on capacitors 320A and 320B (collectively referred to as "capacitors 320") by switches 322A and 322B (collectively referred to as "switches 322"). The charge on capacitors 320 counters the charge on capacitors 106 in steady state. More specifically, the charge on capacitors 320 dominates the feedback path in steady state for low frequencies. Thus, current substantially flows through negative feedback path 92 at steady state and little or no current flows through negative feedback path 118. As a result, the ratio of feedback capacitors 112 and 320 and the time-constant of integrator 302 sets the corner frequency of the high pass filter provided by negative feedback path 92. The corner frequency may be set to equal to approximately 2.5 Hz, 0.5 Hz, or 0.05 Hz, or other desired frequencies. With feedback capacitors 112 on chip, the high-pass filter characteristics can be dynamically changed to help with recovery from an overload or transient.

Switches 312 and 322 may be CMOS SPDT switches or other switches that provide fast switching dynamics. Capacitors 310, 314, and 320 may be poly-poly capacitors or other types of MOS capacitors.

It should be understood that feedback path 92, as shown in FIG. 11, may be generally applied to an instrumentation amplifier as broadly described in this disclosure. Accordingly, instrumentation amplifier 300 should not be considered limiting in any way. Instead, instrumentation amplifier 300 is one of many example instrumentation amplifiers that may include a negative feedback path for constructing a high pass filter as described in this disclosure. For example, feedback path 92, as shown in FIG. 11, may be added to instrumentation amplifier 200 in FIG. 9.

Figure 12:
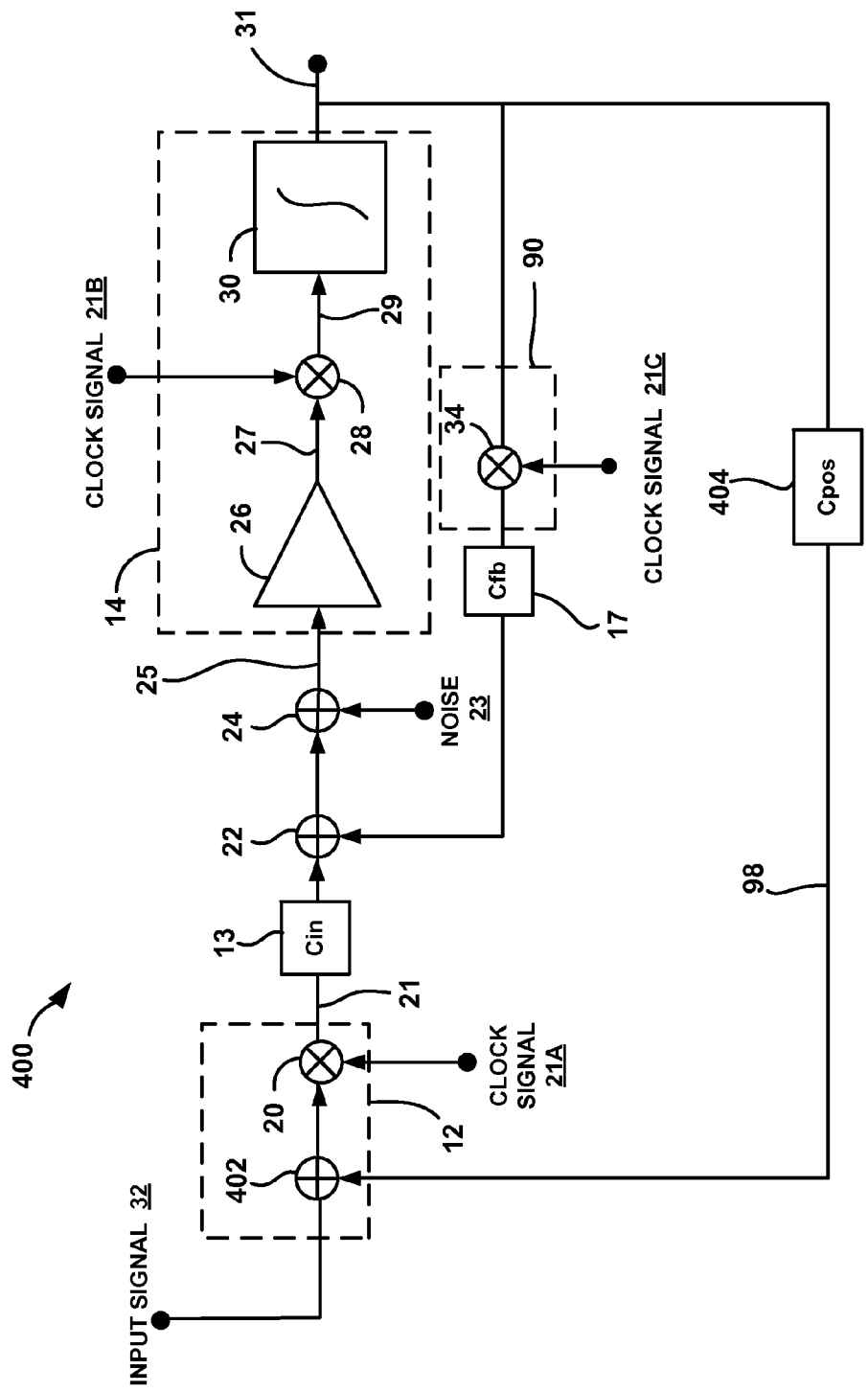
FIG. 12 is a diagram illustrating a signal path flow for an instrumentation amplifier in accordance with an embodiment of the invention that includes a positive feedback path for increasing input impedance.

FIG. 12 is a diagram illustrating an exemplary signal flow for an instrumentation amplifier 400 that includes a positive feedback path for increasing the input impedance of the instrumentation amplifier. The architecture of instrumentation amplifier 400 may be substantially the same as that of instrumentation amplifier 10 with respect to FIG. 2, but with positive feedback path 98 included to provide additional signal processing. Accordingly, similar numbered components in FIG. 12 share the same functionality of those in FIGS. 2 and 10. In the interest of brevity and to avoid redundancy, the signal flow through front end 10, mixer amplifier 14, and feedback path 90 is not described in detail. Instead, the flow of output signal 31 which is produced by mixer amplifier 14 through positive feedback path 98 is described.

In general, positive feedback path 98 taps off of the output of mixer amplifier 14 or optionally the output of the integrator 302 in feedback path 92, if provided. Positive feedback path 98 provides feedback to front end 12 prior to modulator 20, i.e., prior to application of chopping input signal 32. As shown in FIG. 12, positive feedback path 98 includes a switched capacitor arrangement 404 (Cpos) that is driven by clock signal 21C. In particular, switched capacitor 404 is used to create a resistance that is substantially equal to the effective resistance at the input of instrumentation amplifier 400. The effective input resistance (Reff) of instrumentation amplifier is given in equation (2) below, where the frequency of clock signals 21A-C is Fclock, and Cin is the capacitance of the input capacitors 106A, 106B at modulator 20. Accordingly, the charge draw looking into instrumentation amplifier 400 is described by equation (3), where Q is the electric charge, and ΔVin is the change in voltage.

$$Reff = 1/(Fclock \cdot Cin) \quad (2)$$

$$\frac{dQ}{df} = Cin \cdot Fclock \cdot \Delta Vin \quad (3)$$

Positive feedback path 98 compensates for the current passing through the effective resistance by "replacing" or putting charge back onto the switched input capacitors 13 of modulator 20. Because the output voltage of instrumentation amplifier 400 without feedback path 98 is proportional to the differential input voltage multiplied by the ratio of the capacitance Cin of the input capacitors 106A, 106B of modulator 20 to the capacitance Cfb of the feedback capacitors 112A, 112B of modulator 34, switched capacitor arrangement 404 (Cpos) samples output of mixer amplifier 14 and uses positive feedback to replace the lost charge. In other words, positive feedback path 98 injects current that compensates for current passing through the effective input resistance. Positive feedback path 98 may raise the equivalent low frequency input impedance by an order of magnitude or more.

Positive feedback path 98 may also be used at the same time as positive feedback path 92. In this case, positive feedback path 98 may tap off of the output of the integrated signal output by positive feedback path 92. With respect to FIG. 10, positive feedback path 98 could tap off of the output of integrator 302, rather than the output of mixer amplifier 116.

Figure 13:
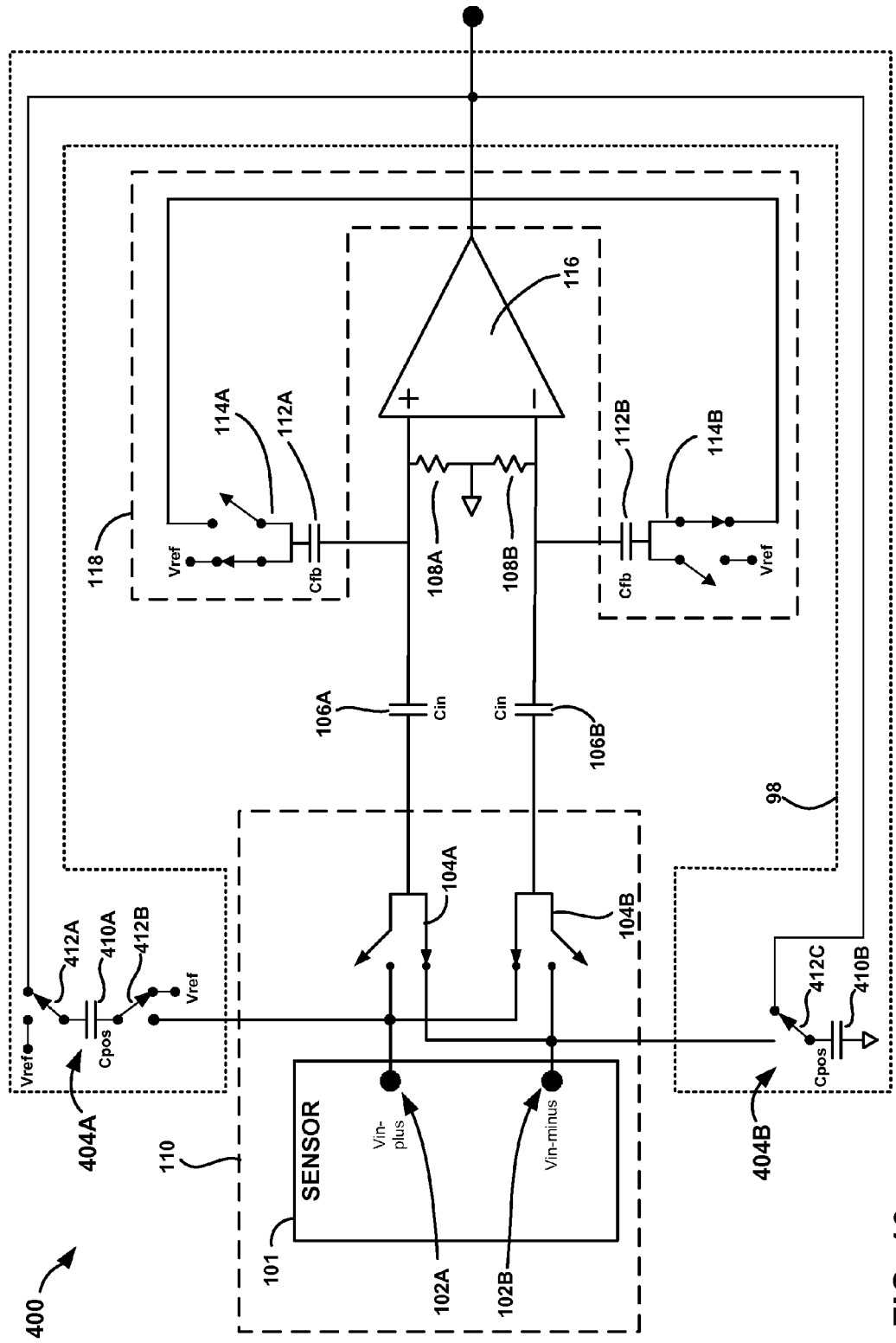
FIG. 13 is a circuit diagram illustrating the instrumentation amplifier of FIG. 12.

FIG. 13 is a circuit diagram illustrating instrumentation amplifier 400. In FIG. 13, the architecture of instrumentation amplifier 400 is substantially identical to that of instrumentation amplifier 300, but with positive feedback path 98 tapping off of the output of mixer amplifier 116 and providing positive feedback to capacitors 106 of front end 110. Components that share same number between FIG. 13 and FIGS. 8 and 11 share the same functionality. Accordingly, the operation of these components is not described in the interest of brevity and to avoid redundancy. However, the operation of positive feedback path 98 is described.

In FIG. 13, positive feedback path 98 provides differential feedback through a first feedback path branch and a second feedback path branch. The first feedback path branch (top branch) modulates the output of mixer amplifier 116 to provide positive feedback to the positive input terminal of mixer amplifier 114. The first feedback path branch (top branch in FIG. 13) includes capacitor 410A, switch 412A, and switch 412B. Switch 412A selectively couples one side of capacitor 410A to either a reference voltage Vref or the output of mixer amplifier 116. Switch 412B selectively couples the other side of capacitor 410A to either Vref or input port 102A of sensor 101. The second feedback path branch (bottom branch in FIG. 13) includes capacitor 410B and switch 412C. One side of capacitor 410B is coupled to ground. Switch 412C selectively couples the other side of capacitor 410B to either the output of mixer amplifier 116 or input port 102B of sensor 101.

Capacitors 410A and 410B are both coupled to the output of mixer amplifier 116 during a first clock phase. Thus, during the first clock phase, capacitors 410A and 410B sample the output of mixer amplifier 116. One end of capacitor 410A is coupled to Vref during the first phase. During a second clock phase, capacitors 410A and 410B are coupled at one end to input ports 102A, 102B, respectively. At the other end, during the second clock phase, capacitor 410A is coupled to Vref, while capacitor 410B is coupled to ground. The sizes of capacitors 410A and 410B are selected according to the charged needed to compensate for the sampling of the input capacitors 106A, 106B during front end modulation. As an example, each capacitor 410A, 410B may have a capacitance value that is approximately twice the value of the feedback capacitance Cfb of each respective feedback capacitor 112A, 112B. Capacitors 410A, 410B may be provided on-chip for close matching to capacitors 106A, 106B and 112A, 112B.

In the second feedback path branch (bottom), charge is delivered to the front end switch 104b during a second clock phase, i.e., after the first clock phase in which capacitor 410B is coupled to sample the output of mixer amplifier 116. Similarly, in the first feedback path branch (top), charge is delivered to front end switch 104A during the second clock phase.

To create a differential charge transfer from the single ended output of mixer amplifier 116, a different switching scheme is employed in the first feedback path branch (top) than in the bottom feedback path branch). The clock frequency used to actuate switches 412A, 412B, 412C may be the same as the chopping frequency. The reference voltages used for feedback path 98, and particularly the reference voltages to which capacitor 410A is coupled in phase 1 and phase 2, should match the reference voltage used in feedback path 118.

Switches 412A, 412B and 412C may be CMOS SPDT switches or other switches that provide fast switching dynamics. Capacitors 410A and 410B may be poly-poly capacitors or other types of MOS capacitors, and may be formed on-chip with capacitors 112A, 112B, 106A and 106B.

As previously described, positive feedback path 98 may also be used with negative feedback path 92 at the same time. In this case, using FIG. 11 as a reference, positive feedback path 98 could sample off of the output of integrator 302. That is, switches 412A and 412C could be connected to the output of integrator 302 instead of the output of mixer amplifier 116.

Figure 14A:
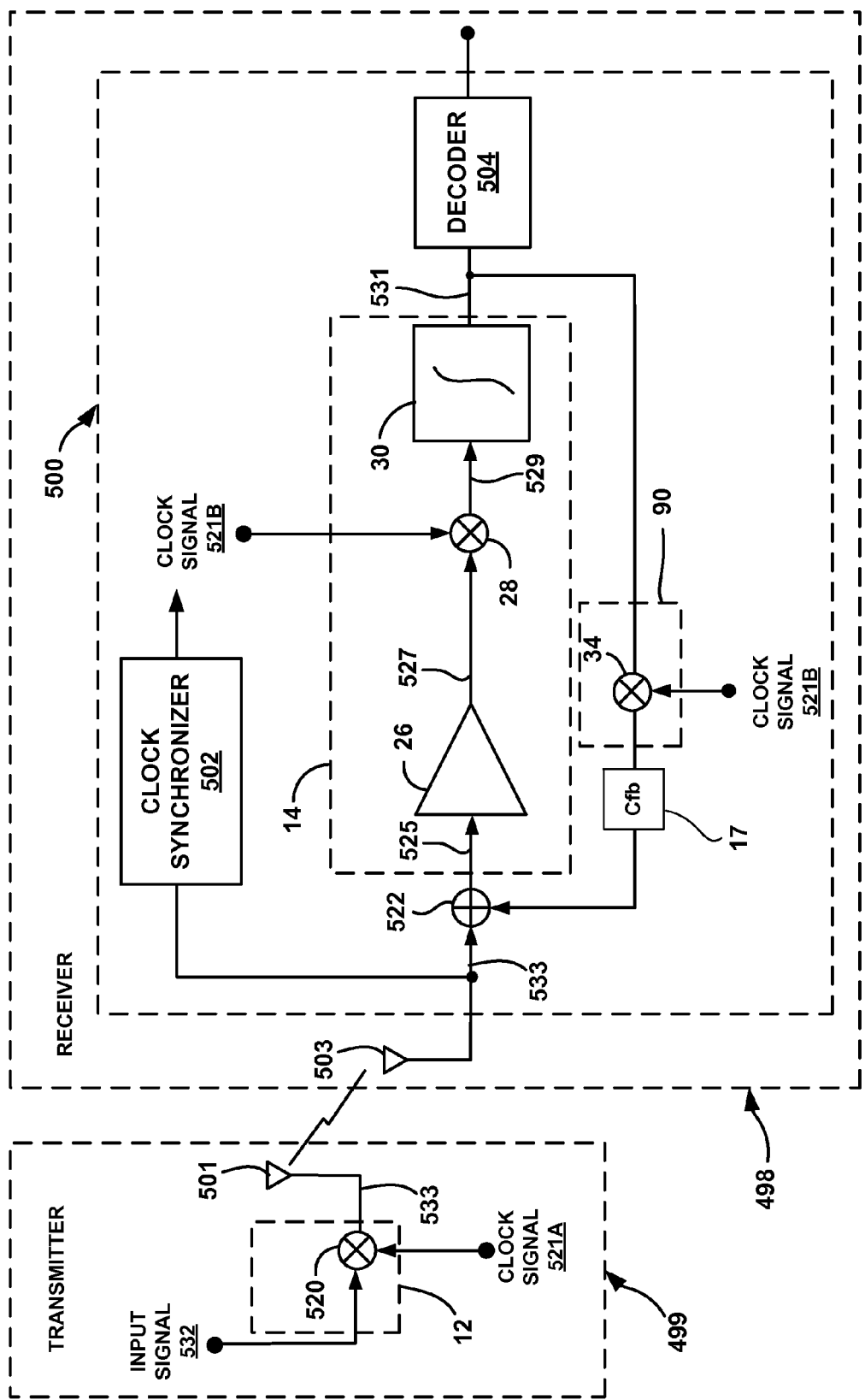
FIG. 14A is a diagram illustrating a signal flow path for an instrumentation amplifier in accordance with an embodiment of the invention that is used to demodulate received telemetry signals.

FIG. 14A is a diagram illustrating the signal flow for an instrumentation amplifier 500 that is used as part of a receiver 498 in a telemetry system. Instrumentation amplifier 500 may be used, for example, as part of a receiver 498 in an implantable pulse generator (IPG), implantable drug delivery device, or other type of implantable medical device (IMD) implanted within a patient that communicates, via telemetry, with an external programming device, such as a clinician or patient programmer. In addition, instrumentation amplifier 500 may also be located in an external programming device that communicates with an IPG or other type of IMD implanted within the patient. Receiver 498 may receive signals from a transmitter 499 associated with an IMD or external programmer. Receiver 498 and transmitter 499 together form a telemetry system that makes use of an instrumentation amplifier 500 as described in this disclosure. As will be described, a first chopper stage resides in the transmitter 499 while a second chopper stage and feedback path reside in instrumentation amplifier 500 in receiver 498.

In general, instrumentation amplifier 500 may be implemented as part of telemetry circuitry in an IMD or programming device for an IMD that communicates using "arms length telemetry." Arms length telemetry (ALT) refers to telemetry over distances of approximately 10 cm or greater. For example, ALT may operate over a distance of approximately 50 cm or a distance of approximately 1 meter. Accordingly, ALT eliminates the burden of placing a programming device directly over the IMD for communication. However, the signal level for ALT is on the order of hundreds of microvolts as a result of the signal level dropping off as a cubic power of distance between the programming device and the IMD. Consequently, ALT requires micropower circuits to extract the transmitted signal while suppressing or rejecting out of band aggressors, i.e., noise. Aggressors include stimulation loop aggressors and similar phenomena.

Instrumentation amplifier 500 may be configured to provide synchronous demodulation for the detection of on-off-keyed (OOK) signals. As an example, such signals may be transmitted by transmitter 499 in a 175 kHz industry-scientific-medical (ISM) band. The chopper stabilized mixer amplifier described in this disclosure, i.e., mixer amplifier 14 with negative feedback path 90, can be implemented in instrumentation amplifier 500 to provide synchronous demodulation with very low offset and stable gain. Moreover, the gain of instrumentation amplifier 500 can be conveniently determined by on-chip capacitor ratios, i.e., the ratio of the capacitance of the feedback capacitors in negative feedback path 90 to the capacitance of the input capacitors. As shown in FIG. 14A, instrumentation amplifier 500 also includes a clock synchronizer 502 to correct for phase mismatch between clocks at the transmitter 499 and receiver 498. Clock synchronizer 502 may include another chopper stabilized mixer amplifier in accordance with an embodiment of this disclosure.

In one example embodiment, the received signals may be transmitted using on-off keying of a 175 kHz signal to send data between a programming device and the IMD in which a receiver 498 incorporating instrumentation amplifier 500 resides. The 175 kHz signal falls within the ISM band. The data may be framed with a fixed interval of 22 μs to provide a 4.4 kbps rate. The duty cycle of the signal within the frame signifies whether the data bit is a one or a zero.

It should be understood that instrumentation amplifier 500 is not limited to the above protocol. Instead, this protocol is one of many example protocols that may be used for ALT. Accordingly, instrumentation amplifier 500 and the signal flow for instrumentation 500 in FIG. 14A should be viewed as examples for broadly teaching how a chopper stabilized instrumentation amplifier 500 described in this disclosure can be used for synchronous demodulation of signals for arms length telemetry and, therefore, should not be considered limiting in any way.

The signal flow of instrumentation amplifier 500 in FIG. 14A begins with transmitter 499, which includes modulator 520. Modulator 520 receives an input data signal 532 containing data to be transmitted, and chops the input signal at a chopping frequency defined by clock signal 521A to produce an output signal for transmission to receiver 498 via transmit antenna 501 and receiver antenna 503. Additional amplifier or filter components may be provided to permit transmission of the modulated signal produced by modulator 520 In terms of an analog to the other instrumentation amplifier embodiments described in this disclosure, transmitter 499 and modulator 520 form, in effect, a front end 12 that provides the first chopping stage for the signal flow. Hence, in this case, front end 12 of the overall instrumentation amplifier 500 is a transmitter 499 associated with a separate device, e.g., an IMD or programmer. The transmitter 499 produces a digital bit stream and converts the digital bit stream into an analog waveform (input signal 532) that is modulated to the carrier frequency, e.g., 175 kHz, by modulator 520 to produce wireless signal 533 for transmission over a wireless channel. The wireless channel, in this case, is the path of the wireless signal 533 between the programming device and the IMD implanted within the patient.

Wireless signal 533 is received by receive antenna 502. Mixer amplifier 14 receives a signal 525 from summing node 522. As previously described with respect to FIGS. 2, 10 and 12, mixer amplifier 14 may include an amplifier 26, a demodulator 28, and an integrator 30. Components with similar numbers in each of these figures may operate in a similar manner. For example, amplifier 26 amplifies input signal 525 to produce an amplified signal, i.e., amplified signal 527. Modulator 28 demodulates amplified signal 527 at the chop frequency to produce demodulated signal 529, which carries the original data stream located back at baseband and noise modulated up to 175 kHz. Integrator 30 suppresses the signal components that are out of band with the baseband components, thereby producing output signal 531 which is substantially free of noise 523.

As previously described with respect to FIG. 10, negative feedback path 90 provides negative feedback that keeps the signal change at the input to mixer amplifier 14 small. In particular, negative feedback path 90 includes modulator 34 which modulates output signal 531 to produce a differential feedback signal that is added to the signal path at summing node 522. Clock signal 521C drives modulator 34 to modulate output signal 531 at the chopping carrier frequency via feedback capacitor 17 (Cfb). Negative feedback path 90 may include two feedback path branches that apply the negative feedback to the positive and negative input terminals of differential mixer amplifier 14. The feedback paths are out of phase with each other to ensure that a negative feedback path exists during each half of the clock cycle. In this way, mixer amplifier 14 provides a stable, low noise output while operating at low power.

In FIG. 14A, however, the clocks that provide clock signals 521A and 521B are not located in the same physical location. In particular, clock signal 521A is provided by a clock located in the transmitter 498 and clock signal 521B is located in instrumentation amplifier 500 in receiver 499. Accordingly, clock signal 521B may not be synchronized with clock signal 521A. The phase shift between clock signals 521A, 521B may result in a signal null in demodulated signal 529 when the shift is 90 degrees, or a beat frequency that makes decoding the received signal very difficult if not impossible. Clock synchronizer 503 corrects for the phase mismatch between clock signals 521A, 521B.

As shown in FIG. 14A, clock synchronizer 502 uses the received signal, i.e., input signal 533 to correct for phase mismatch between clock signals 521A and 521B. Clock signal 521B is used by modulator 528 to chop amplified signal 527, and by modulator 34 in feedback path 90 to chop output signal 531 for feedback to summing node 522. With clock signal 521B and clock signal 521A substantially synchronized with each other, decoder 504 can produce a digital bitstream from output signal 531. Decoder 504 may be a slicer or similar component that can convert an analog baseband signal into a digital bitstream. For example, decoder 504 may include a slicer formed from a comparator that detects a level of the output signal. The comparator may have a dynamic level adjustment to account for variations in the background noise floor. Mild hysteresis may be added to the slicer to prevent multiple triggers in the digital waveform for small amplitude transitions over short periods of time.

Clock synchronizer 502 may be implemented as a phase lock loop or other component known in the radio frequency (RF) communication arts that corrects for a phase mismatch between the clocks at the transmitter and receiver. In one example embodiment, clock synchronizer 502 may include a chopper stabilized mixer amplifier as described in this disclosure. The chopper stabilized mixer amplifier can be used to derive the mixer clock, the clock that provides clock signal 521B to mixer amplifier 14, from the received signal thereby eliminating the need for quadrature reconstruction. In other words, the core feature of the instrumentation amplifier described in this disclosure can be used as a key building block in clock synchronizer 502 for building a synchronous clock derived from the received signal. This core feature has been described in detail with respect to mixer amplifier 14 with negative feedback 90.

Using a chopper stabilized mixer amplifier in clock synchronizer 502 to derive the clock signal may have several advantages. First, the mixer amplifier is chopper stabilized, providing minimal referred to the antenna offset (RTAO). This provides a clean signal for extracting the small amplitude received signals, which may be on the order of 100 microvolts. The use of feedback path 90 and a compensation network allows loop dynamics to be adjusted to suppress out-of-band transients while maintaining lock on the received signal. In addition, signal processing is achieved with the chopper mixer elements, which keep current drawn from a power supply to a minimum. For example, the net standby current for instrumentation amplifier 500 with no polling may be approximately 5 µA or less in some embodiments.

In summary, receiver 498 may have three major building blocks. The front end at antenna 503 is attached to two chopper stabilized mixers, one of which is used in a phase-lock loop 502 to derive the reference clock, and the other of which is used in mixer amplifier 14 to translate the received signal to baseband, and amplify it while suppressing out-of-band aggressors. In general, a chopper-stabilized mixer amplifier is provided in clock synchronizer 502 as a linear mixer to operate as a phase detector in a voltage controlled oscillator (VCO), while the other chopper-stabilized mixer amplifier operates as a linear mixer to provide demodulation, amplification, and lowpass filtering for data extraction. The output of the in-phase mixer amplifier 14 is passed to decoder 504 for digitization. The architecture of FIG. 14A provides a synchronous demodulator that may be capable of high sensitivity to received signals in the transmission band while rejecting out-of-band aggressors. Low-power synchronous demodulation is made possible by the chopper-stabilized mixer architecture, which may be used in mixer amplifier 14 and clock synchronizer 502.

Figure 14B:
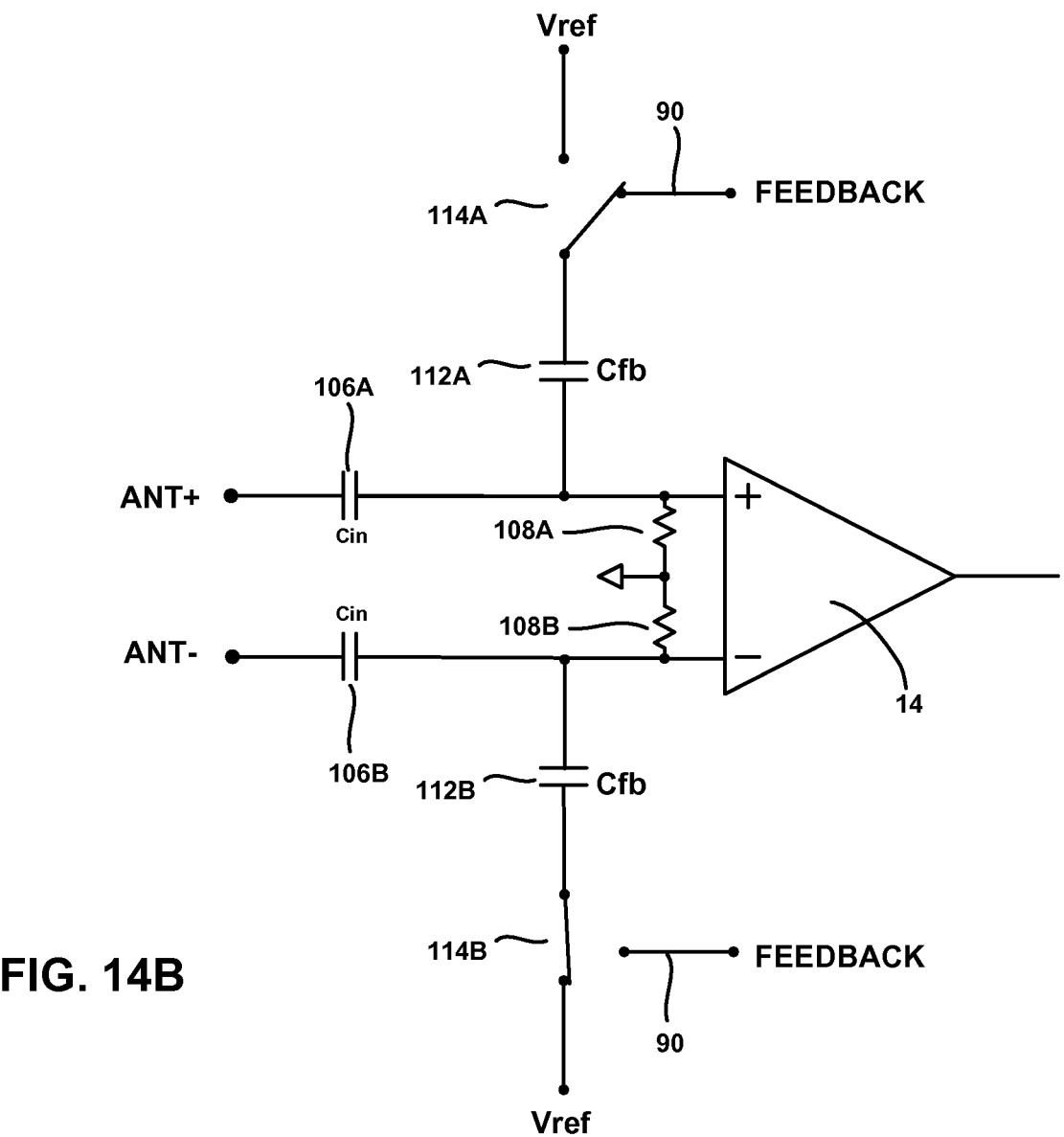
FIG. 14B is a circuit diagram illustrating antenna input and feedback circuitry for the telemetry-configured instrumentation amplifier of FIG. 14A.

FIG. 14B is a circuit diagram illustrating input and feedback circuitry for the telemetry-configured instrumentation amplifier of FIG. 14A. As shown in FIG. 14B, mixer amplifier 14 receives a modulated differential input signal via input capacitors 106A, 106B (Cin). Input capacitor 106A feeds a positive end of the differential antenna signal (ANT+) to the positive input of mixer amplifier 14. Input capacitor 106B feeds a negative end of the differential antenna signal (ANT−) to the negative input of mixer amplifier 14. Resistors 108A, 108B may be provided to set the inputs of mixer amplifier 14 to set an input bias impedance. Positive and negative inputs of mixer amplifier 14 may be coupled to feedback path branches of feedback path 90 via feedback capacitors 112A, 112B (Cfb) and switches 114A, 114B, as in other embodiments. The capacitance of the feedback capacitor 112 (Cfb) in relation to the capacitance of the input capacitor 106 (Cin) sets the nominal gain of the overall instrumentation amplifier. As in other embodiments, negative feedback path 92 also may be provided to set a highpass cutoff for the instrumentation amplifier.

Figure 15A:
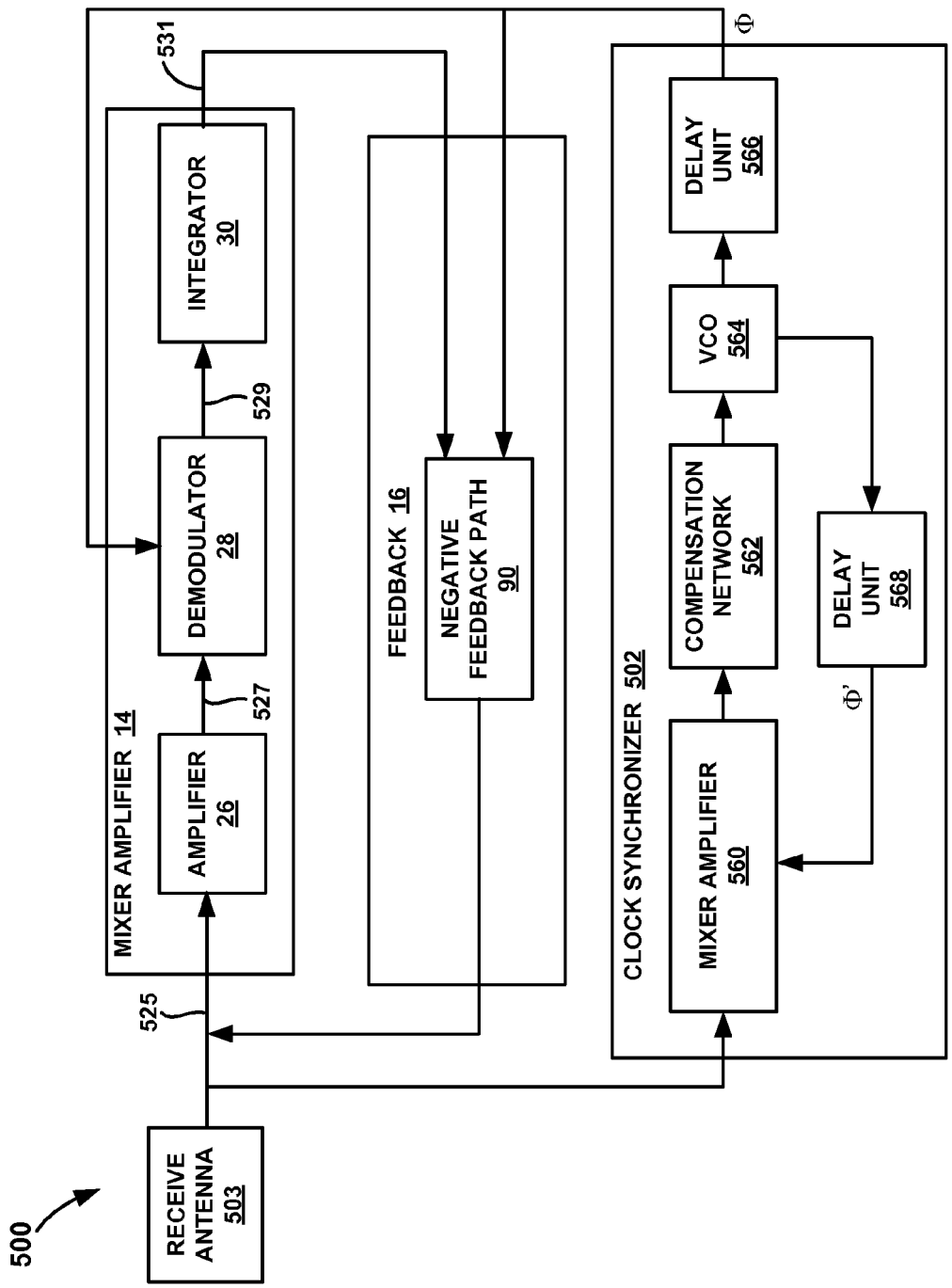
FIG. 15A is a block diagram illustrating the telemetry-configured instrumentation amplifier of FIG. 14A.

FIG. 15A is a block diagram illustrating instrumentation amplifier 500. In accordance with this disclosure, instrumentation amplifier 500 is illustrated in FIG. 15A as including mixer amplifier 14 and feedback path 16. Unlike the previously described embodiments, however, front end 12 is in a different physical location, consistent with FIGS. 14A and 14B. In particular, as described with reference to FIG. 14A, front end 12 resides within a transmitter 499 in a remote IMD or programmer. The signal received by receive antenna 503 of instrumentation amplifier 500 has already been chopped at the remote IMD or programmer. Instrumentation amplifier 500 includes clock synchronizer 502 which corrects for the phase mismatch between the clock that drives front end 12 in the remote device and the clock that drives mixer amplifier 14. Clock synchronizer 502 provides a linear mixer that extracts the phase reference for use in the data demodulation path provided by mixer amplifier 14.

As shown in FIG. 15A, receive antenna 503 receives the wireless signal output by the remote transmitter. Mixer amplifier 14 of instrumentation amplifier 500 operates as previously described and may be implemented as a modified folded cascode amplifier with switching at low impedance nodes. Thus, mixer amplifier 14 is illustrated in FIG. 15A as including amplifier 26, demodulator 28, and integrator 30. In FIG. 15A, mixer amplifier 14 receives modulated input signal 525 from receive antenna 503. Amplifier 26 amplifies modulated input signal 525 to produce amplified signal 527. Demodulator 28 demodulates amplified signal 527 to produce demodulated signal 529 using switching at low impedance nodes of the folded cascode amplifier. However, demodulated signal 529 may experience signal nulls or a beat frequency unless the clock driving demodulator 28 is synchronized with the clock driving the modulator at the transmitter. This is the reason that instrumentation amplifier includes clock synchronizer 502.

Demodulated signal 29 may contain 1/f noise, popcorn noise, and offset at the carrier frequency (175 kHz) and the original signal content at baseband. Integrator 30 integrates demodulated signal 529 to produce output signal 531. In particular, integrator 30 integrates demodulated signal 529 with respect to a reference voltage provided by a receiver reference and bias generator and acts as a low pass filter to suppress signal components with a frequency outside of the baseband. Consequently, noise sitting at the carrier frequency of demodulated signal 529 is substantially eliminated to produce a stable, low noise output signal 531.

Again, output signal 531 is stable because of the negative feedback provided by negative feedback path 90. Without negative feedback path 90, output signal 531 includes a series of spikes superimposed on the desired signal that make it very difficult to slice the signal into a digital bitstream and decode the data. These spikes are a result of operating with very low power which limits the bandwidth of mixer amplifier 14. Providing negative feedback at the input to mixer amplifier 14 keeps the signal change small in steady state so that the only significant voltage transitions occur at switching nodes. Negative feedback path 90 includes symmetrical feedback path branches to provide the negative feedback to respective positive and negative differential inputs of mixer amplifier 14. Each feedback path branch modulates output signal 531 with a reference voltage provided by a receiver bias and reference voltage generator. The feedback path branches are 180 degrees out of phase with each other provide feedback during each half of the clock cycle. In this way, mixer amplifier 14 and negative feedback path 90 substantially eliminate glitching to provide stable, low noise output signal 531.

Output signal 531 may experience signal nulls or a beat frequency if the transmitter clock and receiver clock are not in phase with each other. The transmitter clock signal drives the modulator that modulates the baseband signal to the carrier frequency, e.g., 175 kHz. The receiver clock supplies a clock signal to mixer amplifier 14 and negative feedback path 90. More specifically, the receiver clock supplies the clock signal that drives demodulator 28 to demodulate the received, amplified signal 527 and the signal(s) that drive modulation of the output signal 531 in negative feedback path 90.

Clock synchronizer 502 corrects for the phase mismatch between the transmitter clock and the receiver clock. In particular, clock synchronizer builds a synchronous clock derived from the received signal, i.e., modulated input signal 525, to produce a correction signal that is used by demodulator 28 in mixer amplifier 14 and the modulator in negative feedback path 90 to compensate for the phase mismatch.

Clock synchronizer 502 in FIG. 15A avoids problems that may be associated with using a comparator to derive the mixer clock from the received signal. The problems associated with using a comparator may include difficulty producing a square wave because of the low power received signal. That is, it may be difficult for a comparator to square up millivolt signals at the 175 kHz clock frequency. The comparator also typically requires an AC coupled preamplifier or other mechanism for removing DC offsets on the front-end, which would otherwise lead to a significant duty cycle error and/or dead zone for signals on the order of millivolts or less. Further, a comparator has no memory and, therefore, any signal crossing results in the signal mixing into the baseband. This is a problem with signals on the order of hundreds of millivolts and, more particularly, signals on the order of hundreds of microvolts with sensitivity at the 175 kHz ISM band.

In FIG. 15A, clock synchronizer 502 operates as a phase lock loop and includes chopper stabilized mixer amplifier 560, compensation network 562, voltage controlled oscillator (VCO) 564, and delay units 566 and 568. Mixer amplifier 560 includes a mixer amplifier, arranged in a manner similar or identical to mixer amplifier 14. Instead of receiving negative feedback to the inputs of the mixer amplifier, however, mixer amplifier 560 receives a quadrature phase clock feedback that is applied to a demodulator in mixer amplifier 560. Hence, in some embodiments, chopper stabilized mixer amplifier 560 may include similar components and operate similar to mixer amplifier 14 described in this disclosure. For example, chopper stabilized mixer amplifier 560 may include, with respect to FIG. 15A, an amplifier, a demodulator, and an integrator that form a mixer amplifier and be coupled to receive a negative feedback path that provides the chopper stabilization for producing a stable output. As mentioned above, however, the negative feedback received by mixer amplifier 560 may be a quadrature phase feedback to adjust the clock frequency of the demodulator. The quadrature phase feedback is out of phase with the input signal received by mixer amplifier 560. Thus, chopper stabilized mixer amplifier 560 includes a mixer amplifier having the modified folded cascode amplifier architecture with switching at low impedance nodes. This architecture is illustrated in FIG. 6. Chopper stabilized mixer amplifier 560 is illustrated as a single block in FIG. 15A.

In general, clock synchronizer 502 provides a feedback path between its output and demodulator 28 of mixer amplifier 14. Chopper stabilized mixer amplifier 560 receives modulated input signal 525 from receive antenna 503 and produces a stable, low noise signal. Importantly, chopper stabilized mixer amplifier 560 substantially removes offset from the received signal and outputs a signal that substantially or closely approximates a square wave. As a result, chopper stabilized mixer amplifier 560 may avoid the previously discussed problems associated with using a comparator.

Compensation network 562 receives the output of chopper stabilized mixer amplifier 560 and applies an integrator and high-pass zero. By using an integrator in compensation network 562, the output adjusts VCO 564 such that the feedback clock (output of VCO 564) is in quadrature with the received signal. In other words, because zero net signal is output by chopper stabilized mixer amplifier 560 in steady state, the transmitter clock and the output of VCO 564 are in quadrature. The key is that by using an integrator in compensation network 562, the integrator holds the VCO value while the received signal is in the "off state" (output of chopper stabilized mixer amplifier 560 still zero since signal is gone), and reacquires the VCO quickly when the signal goes high again. In this way, clock synchronizer 502 can be viewed as a "phasor fly wheel" that is locked onto the received signal, i.e., modulated input signal 25, in quadrature.

VCO 564 may operate at approximately 350 kHz (2*175 kHz ISM frequency) for the purpose of this example embodiment. The output of VCO 564 is processed by delay units 566 and 568 to provide quadrature signals to the chopper stabilized mixer amplifier 560, demodulator 28, and the demodulator in negative feedback path 90. Delay unit 568 feeds the output of VCO 564 back to the demodulator of chopper stabilized mixer amplifier 560. Delay unit 566 is tied to the opposite phase of VCO 564 to create an in-phase clock for demodulator 28 and negative feedback path 90. That is, because the output of VCO 564 is locked onto the input signal in quadrature, delay unit 566 introduces delay of half a clock cycle to create an in-phase clock for mixer amplifier 14 (demodulator 28) and negative feedback path 90. Hence, delay unit 566 is configured to feed the output of VCO 564 with a first phase (d) to demodulator 28 of mixer amplifier 14 and modulator 34 of negative feedback path 90, while delay unit 568 is configured to feed the output of VCO 564 with a second phase of $\Phi'$ to the demodulator in mixer amplifier 560. The outputs of delay units 566 and 568 are 90 degrees out of phase with one another. With demodulator 28 using a clock signal that is in phase with the transmitter clock, signal processing can be applied to the output of mixer amplifier 14 to recover and decode the transmitted bits. Delay units 566 and 568 may be D-type flip flops or other components that can be used to introduce delay into the signal.

In general, clock synchronizer 502 may be a phase-locked-loop that extracts the phase reference for the data demodulation path of mixer amplifier 14 and negative feedback path 90. The feedback from VCO 564 adjusts the modulation clock of chopper stabilized mixer amplifier 560 such that it is 90 degrees out of phase with the clock frequency of the input signal 525. In this case, chopper stabilized mixer amplifier 560 may act as a linear phase detector having an output that scales as Vin*cos($\Phi$), where Vin is the input voltage from receive antenna 503, and $\Phi$ is the phase difference between the chopper stabilized mixer amplifier 560 and the input signal. The resulting transfer function has a null at 90 degrees. For purposes of feedback compensation, small variations about that point can be approximated as a linear relationship.

The compensation of VCO 560 by compensation network 562 may be complicated by the fact that loop gain scales with the input voltage. By using a simple integrator with a zero in compensation network 562, a stable phase lock can be obtained for small signals at the antenna 503. For large voltages, however, the compensation zero creates a large signal at the clock frequency that can saturate the channel and throw off the VCO. The origin of this signal is the "hidden state" of the mixer output at lock, which has no DC component, but a significant signal at the mixer frequency. To eliminate this problem, a second pole can be added to the compensation network 562 beyond loop cross-over. The purpose of this pole is to suppress the signal at the mixer frequency and minimize VCO jitter. As long as the loop gain is not too high, the additional pole should not be a problem. The extra pole is pulled into the compensation zero, which acts to pull the double integrator (one from the mixer amplifier 560 and one from the phase integration of VCO 564) off the imaginary axis and into the left half plane.

As VCO 564 is carefully compensated, a robust lock can be achieved across the dynamic range of the telemetry link. In this way, the loop may be optimally compensated in that it responds more slowly and therefore more heavily filters disturbances as the telemetry link distance increases and signals fall off. In practice, a mode switch driven by received signal strength (RSSI) may be provided to maintain somewhat uniform dynamics over a typical telemetry link range. The mode switch may operate to adjust the loop gain of clock synchronizer 502 based on the level of the input signal. Hence, the loop gain may be decreased for higher input signal levels and increased for lower input signal levels.

Figure 15B:
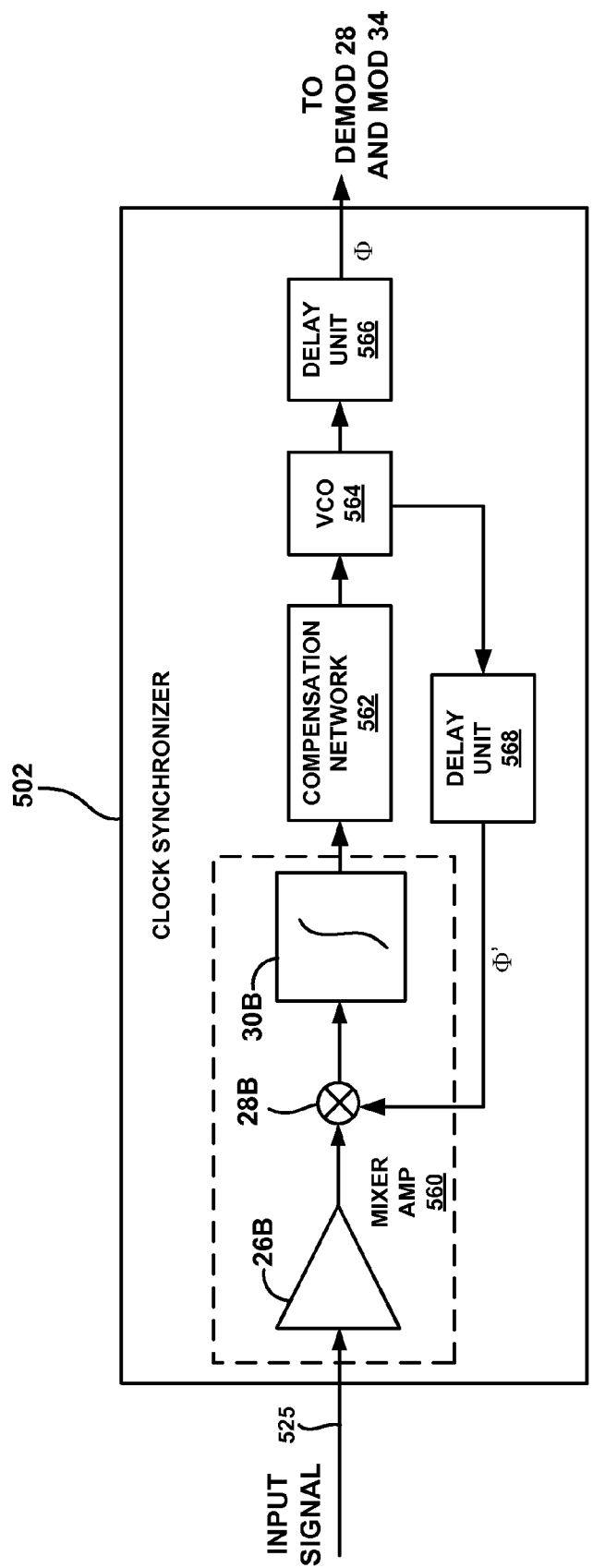
FIG. 15B is a block diagram illustrating a clock synchronizer in FIG. 15A in greater detail.

FIG. 15B is a block diagram illustrating a clock synchronizer 502 in FIG. 15A in greater detail. FIG. 15B illustrates clock synchronizer 502 substantially as shown in FIG. 15A, but further illustrates example components of mixer amplifier 560. In particular, mixer amplifier 560 may include amplifier 26B, modulator 28B, and integrator 30B, all of which may function in a manner similar to amplifier 26, modulator 28 and integrator 30 of mixer amplifier 14. As shown in FIG. 15B, however, delay unit 568 feeds the output of VCO 564 in quadrature phase with input signal 525 to adjust modulator 28B of mixer amplifier 560. Hence, the feedback signal for modulator 28B is 90 degrees out of phase with the input signal 525, and is used to adjust the clock frequency of modulator 28B and thereby maintain chopper stabilization of mixer amplifier 560.

Figure 16:
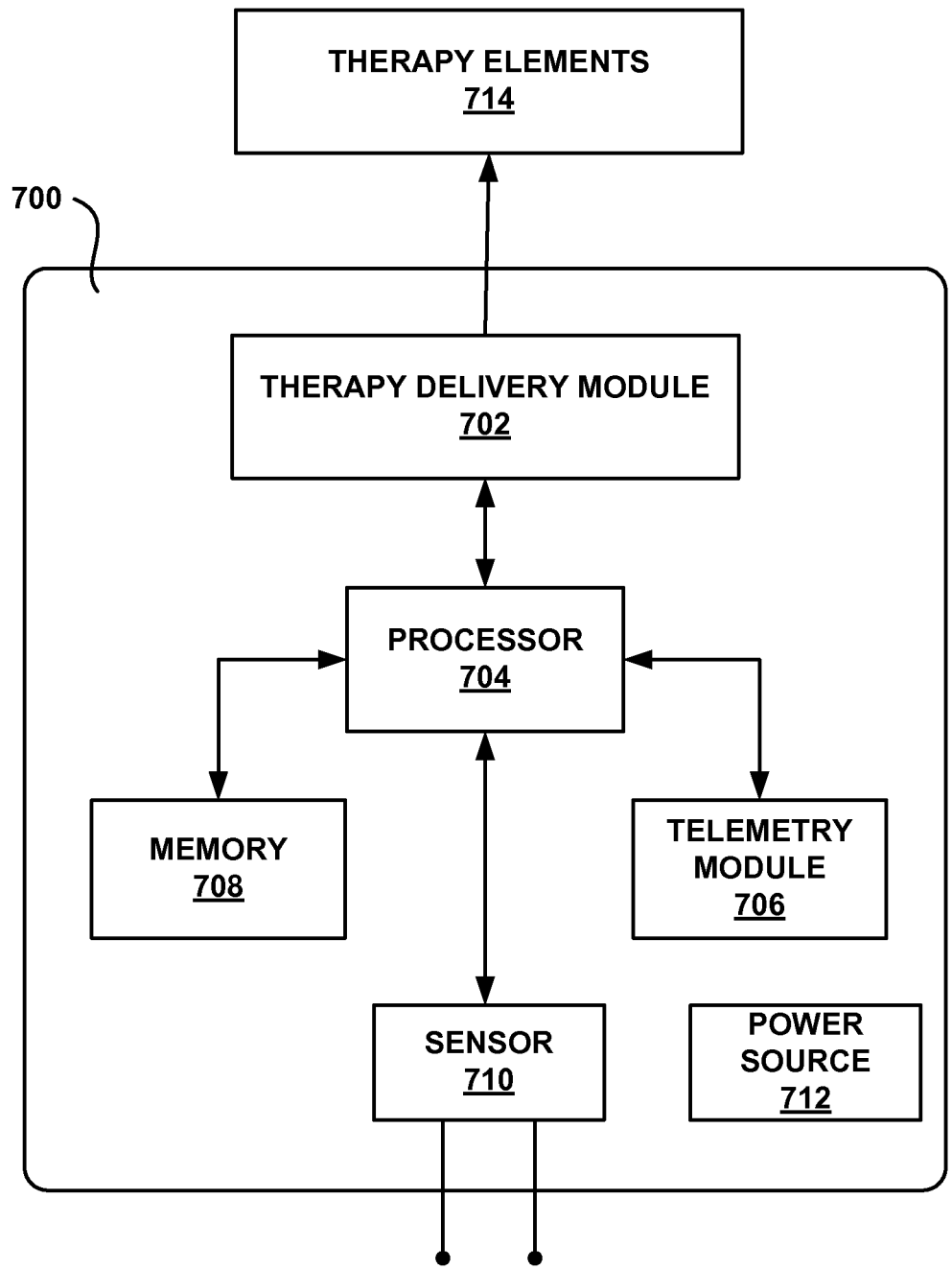
FIG. 16 is a block diagram illustrating an implantable medical device including one or more instrumentation amplifiers for measurement and/or telemetry.

FIG. 16 is a block diagram illustrating various components of an implantable medical device (IMD) 700 including an instrumentation amplifier as described in this disclosure. IMD 700 includes therapy delivery module 702, processor 704, memory 708, telemetry module 706, sensor 710, power source 712, and therapy elements 714. In general, IMD 700 includes a chopper stabilized instrumentation amplifier as part of sensor 710, telemetry module 76, or both.

Sensor 710 may be a pressure sensor, accelerometer, activity sensor, impedance sensor, electrical signal sensor or other sensor configured to monitor heart sounds, brain signals, and/or other physiological signals. Although illustrated in FIG. 16 as contained within IMD 700, a portion of sensor 710 may be located outside of IMD 700. For example, a sensor transducer or one or more electrodes may be located on a distal tip of a lead implanted at a target site within the patient and electrically coupled to IMD 700 via conductors. Alternatively, a sensor transducer or one or more electrodes may be provided on or within a housing of IMD 700. For example, an accelerometer may be provided within an IMD housing or within a lead that extends from the IMD. To sense electrical signals, sensor 710 may include two or more electrodes arranged on a lead, an electrode on a lead and an electrode on an IMD housing, two or more electrodes arranged on an IMD housing, or other electrode arrangements. Sensor circuitry associated with sensor 710 may be provided within sensor 710 in the housing of IMD 700.

In general, sensor 710 provides a measurement of a physiological signal or parameter by translating signal or parameter to an output voltage or current. A chopper stabilized instrumentation amplifier amplifies and filters the sensor output as described in this disclosure to produce a stable, low noise signal with very low power requirements. In this way, the chopper stabilized instrumentation amplifier may enable IMD 700 to operate for several months or years relying on power from a finite power source 712, such as a rechargeable or nonrechargeable battery. In either case, power conversation is desirable.

The output of sensor 710 and, more particularly, the output of the chopper stabilized instrumentation amplifier associated with sensor 710 may be received by processor 704. Processor 704 may apply additional processing, e.g., convert the output to digital values for processing, prior to storing the values in memory 708, and/or transmitting the values to an external programmer via telemetry module 706. Telemetry module 706 also may include at least a portion of a chopper-stabilized instrumentation amplifier. Processor 704 may also control delivery of therapy to the patient based on the output of sensor 710.

IMD 700 may deliver therapy to a patient via therapy elements 714. In other embodiments, IMD 700 may be dedicated to sensing and may not include therapy delivery module 702. Therapy delivery elements 714 may be electrodes carried on one or more leads, electrodes on the housing of IMD 700, one or more fluid delivery devices, or any combination thereof. Accordingly, therapy delivery module 702 may include an implantable stimulation generator or other stimulation circuitry that delivers electrical signals, e.g., pulses or substantially continuous signals, such as sinusoidal signals, to the patient via at least some of the electrodes that form therapy elements 714 under the control of processor 704.

The stimulation energy generated by therapy delivery module 40 may be formulated as stimulation energy for treatment of any of a variety of cardiac or neurological disorders, or disorders influenced by patient neurological response. Example stimulation therapies include cardiac pacing, cardiac defibrillation, deep brain stimulation (DBS), spinal cord stimulation (SCS), peripheral nerve field stimulation (PNFS), pelvic floor stimulation, gastrointestinal stimulation, and the like.

Therapy delivery module 702, processor 704, telemetry module 706, memory 708, and sensor 710 receive operating power from power source 712. Power source 712 may take the form of a small, rechargeable or non-rechargeable battery, or an inductive power interface that transcutaneously receives inductively coupled energy. In the case of a rechargeable battery, power source 712 similarly may include an inductive power interface for transcutaneous transfer of recharge power.

In embodiments in which one or more fluid delivery devices are part of therapy elements 714, therapy delivery module 702 may include a one or more fluid reservoirs and one or more pump units that pump fluid from the fluid reservoirs to the target site through the fluid delivery devices. The fluid reservoirs may contain a drug or mixture of drugs. The fluid reservoirs may provide access for filling, e.g., by percutaneous injection of fluid via a self-sealing injection port. The fluid delivery devices may comprise, for example, catheters that deliver, i.e., infuse or disperse, drugs from the fluid reservoirs to the same or different target sites.

Processor 704 may include a microprocessor, microcontroller, digital signal processor (DSP), application specific integrated circuit (ASIC), field programmable gate array (FPGA), discrete logic circuitry, or a combination of such components. Processor 704 is programmed to control delivery of therapy according to a selected parameter set stored in memory 708. Specifically, processor 704 controls therapy delivery module 702 to deliver electrical stimulation, drug therapy, or a combination of both. For example, processor 704 may control which drugs are delivered and the dosage of the drugs delivered.

Processor 704 may also control therapy delivery module 702 to deliver electrical stimulation with pulse amplitudes, pulse widths, and frequencies (i.e., pulse rates) specified by the programs of the selected parameter set. Processor 704 may also control therapy delivery module to deliver each pulse according to a different program of the parameter set. In some embodiments, processor 704 may control therapy delivery module 702 to deliver a substantially continuous stimulation waveform rather than pulsed stimulation.

Memory 708 may store parameter sets that are available to be selected by the patient for delivery of electrical stimulation and/or drug therapy. Memory 42 may also store schedules. Memory 708 may include any combination of volatile, non-volatile, removable, magnetic, optical, or solid state media, such as read-only memory (ROM), random access memory (RAM), electronically-erasable programmable ROM (EEPROM), flash memory, or the like.

Processor 704 also controls telemetry module 706 to exchange information with an external programmer, such as a clinician programmer and/or patient programmer by wireless telemetry. Processor 704 may control telemetry module 706 to communicate with the external programmer on a continuous basis, at periodic intervals, or upon request from the programmer. In addition, in some embodiments, telemetry module 706 may support wireless communication with one or more wireless sensors that sense physiological signals and transmit the signals to IMD 700.

Telemetry module 706 may operate as a transceiver that receives telemetry signals from an external programmer and transmits telemetry signals to an external programmer. In some embodiments, telemetry module 706 may include a chopper stabilized instrumentation amplifier. More specifically, with respect to FIGS. 14 and 15, the receiver portion of telemetry module 706 may include the back end of a chopper stabilized instrumentation amplifier, referred to as a chopper stabilized mixer amplifier and feedback path, that produces a baseband signal from a received telemetry signal. The receiver portion is described in this disclosure as including only the back end (chopper stabilized mixer amplifier) because the corresponding front end is located in the transmitter portion of the external programmer in communication with IMD 700.

The receiver portion may also include a clock synchronizer that includes another chopper stabilized mixer amplifier, e.g., as described with reference to FIG. 15A. This chopper stabilized mixer amplifier produces an output that can be used by a phase lock loop to generate a correction signal that is used to synchronize the receiver portion of telemetry module 706 with the transmitter of the external programmer.

Telemetry module 706 also may include a transmitter to transmit signals from IMD 700 to an external programmer or to another IMD or external medical device. The transmitter may include a front end of a chopper-stabilized instrumentation amplifier in the sense that it may include a first chopper stage that modulates an input signal with an RF frequency for transmission to an external programmer or another implanted or external medical device.

Importantly, the instrumentation amplifiers in sensor 710 and telemetry module 706 are micropower circuits that provide stable, low noise signals. Thus, IMD 700 may operate over a longer duration of time than would be possible using instrumentation amplifiers that require more power for operation.

Figure 17:
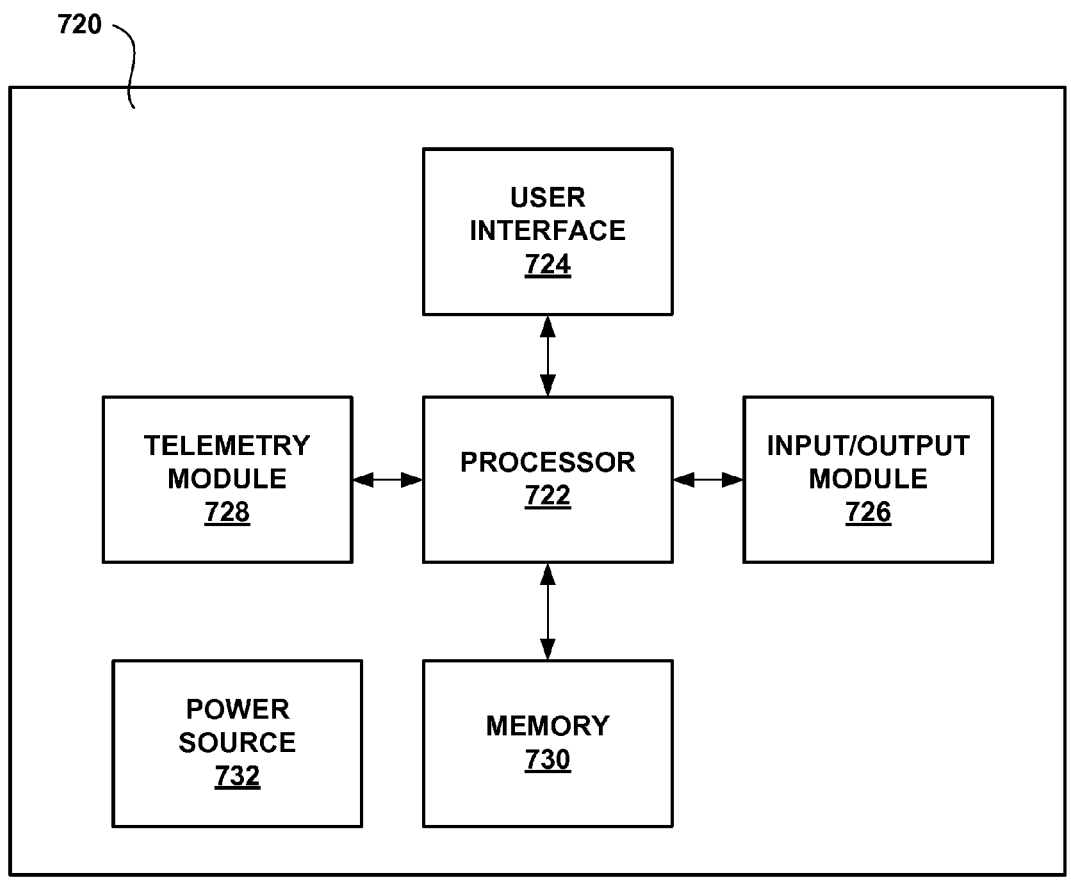
FIG. 17 is a block diagram illustrating a medical device programmer including one or more instrumentation amplifiers for telemetry.

FIG. 17 is a block diagram illustrating an example patient or clinician programmer 720 that allows a patient or clinician to communicate with IMD 700. A patient or clinician may interact with programmer 720 to program therapy, e.g., electrical stimulation, drug therapy, or a combination of both. In the illustrated example, programmer 720 includes processor 722, user interface 724, input/output 726, telemetry module 728, memory 730, and power source 732. Programmer 720 may include a chopper stabilized instrumentation amplifier as part of telemetry module 728.

A patient or clinician, referred to as a user herein, may interact with processor 722 via user interface 724 in order to control delivery of electrical stimulation, drug therapy, or a combination of both. User interface 724 may include a display and a keypad, and may also include a touch screen or peripheral pointing devices as described above. Processor 722 may also provide a graphical user interface (GUI) to facilitate interaction with the user, as will be described in greater detail below. Processor 722 may include a microprocessor, a controller, a DSP, an ASIC, an FPGA, discrete logic circuitry, or the like.

Programmer 720 also includes memory 730. In some embodiments, memory 730 may store parameter sets that are available to be selected by the user for delivery of therapy. Memory 730 may also store schedules. Hence, parameter sets and schedules may be stored in IMD 700, programmer 720, or both. Programmer 720 also includes a telemetry module 728 that allows processor 722 to communicate with IMD 700, and, optionally, input/output circuitry module 726 that allows processor 722 to communicate with another programmer.

Processor 722 may receive parameter set selections made by the user via user interface 724, and may either transmit the selection or the selected parameter set to IMD 700 via telemetry circuitry 728 to deliver therapy according to the selected parameter set. Where programmer 720 stores parameter sets in memory 730, processor 722 may receive parameter sets from another programmer via input/output module 726 during programming by a clinician. For example, a patient programmer may receive parameter sets from a clinician programmer.

Telemetry module 728 may include a transceiver for wireless communication, appropriate ports for wired communication or communication via removable electrical media, or appropriate drives for communication via removable magnetic or optical media. If wireless communication is used, telemetry module 728 may support both wireless communication with IMD 700 and wireless communication with another programmer.

Similar to telemetry module 706 of IMD 700, telemetry module 728 operates as a transceiver for transmitting and receiving signals to and from IMD 700 and possibly another programmer. The receiver portion of telemetry module 728 may include a chopper stabilized mixer amplifier in the main signal path for producing a baseband signal that can be processed to recover the transmitted signal. The corresponding front end to this chopper stabilized mixer amplifier is located in the transmitter portion of IMD 700.

The receiver portion may also include a chopper stabilized mixer amplifier in a clock synchronizer or phase lock loop for the main signal path. This chopper stabilized mixer amplifier down mixes the received signal to baseband to produce a signal that is processed by the phase lock loop to derive a synchronous clock. The transmitter portion of telemetry module 728 may include a first chopper stage that chops an input signal at an RF frequency for transmission to IMD 700 or other programmers or devices.

Power source 732 provides power to programmer 720. That is, power source 732 provides power to processor 722, user interface 724, input/output module 726, telemetry module 728, and memory 730. Because chopper stabilized mixer amplifiers in telemetry module 728 operate at very low power, they may increase the life of power source 732.

Power source 732 may take the form of a small, rechargeable or non-rechargeable battery, or an inductive power interface that transcutaneously receives inductively coupled energy. In the case of a rechargeable battery, power source 732 similarly may include an inductive power interface for transcutaneous transfer of recharge power.

The invention, including instrumentation amplifiers and associated circuitry, devices, systems and methods, may be useful in a variety of applications, For example, the invention may be applied to support sensing relating to therapies for a variety of symptoms or conditions such as cardiac arrhythmia, cardiac fibrillation, chronic pain, tremor, Parkinson's disease, epilepsy, urinary or fecal incontinence, sexual dysfunction, obesity, or gastroparesis, and may provide information useful in controlling electrical stimulation or drug delivery to a variety of tissue sites, such as the heart, the brain, the spinal cord, pelvic nerves, peripheral nerves, or the gastrointestinal tract of a patient.

Hence, an instrumentation amplifier as described in this disclosure may be integrated with, housed in, coupled to, or otherwise associated with an external or implantable medical device, such as a cardioverter/defibrillator, spinal cord stimulator, pelvic nerve stimulator, deep brain stimulator, gastrointestinal stimulator, peripheral nerve stimulator, or muscle stimulator, and also may be used in conjunction with implantable or external drug delivery devices. For example, an instrumentation amplifier and/or associated sensing devices may reside within an implantable medical device housing or a lead or catheter coupled to such a device.

The instrumentation amplifier may be used in conjunction with different therapeutic applications, such as cardiac stimulation, deep brain stimulation (DBS), spinal cord stimulation (SCS), pelvic stimulation for pelvic pain, incontinence, or sexual dysfunction, gastric stimulation for gastroparesis, obesity or other disorders, or peripheral nerve stimulation for pain management. Stimulation also may be used for muscle stimulation, e.g., functional electrical stimulation (FES) to promote muscle movement or prevent atrophy.

Various embodiments of the invention have been described. These and other embodiments are within the scope of the following claims.

The invention claimed is:

1. A medical device comprising:
a current source configured to generate a modulated current at a modulation frequency for application to a load to produce an input signal, wherein the current source comprises a voltage source and a switch that modulates a current produced by the voltage source to produce the modulated current;
an amplifier configured to amplify the input signal to produce an amplified signal; and
a demodulator configured to demodulate the amplified signal at the modulation frequency to produce an output signal indicating an impedance of the load.

2. The device of claim 1, further comprising a modulator configured to modulate the output signal at the modulation frequency to produce a feedback signal.

3. The device of claim 2, further comprising a feedback path that applies the feedback signal to the input signal.

4. The device of claim 3, further comprising an input capacitor that couples the input signal to an input of the amplifier, wherein the feedback path is coupled to apply the feedback signal to the input signal at a node between the input capacitor and the input of the amplifier via a feedback capacitor.

5. The device of claim 4, wherein the input capacitor and the feedback capacitor are arranged such that a ratio of the feedback capacitor to the input capacitor sets a gain of the amplifier.

6. The device of claim 3, wherein the amplifier includes a differential amplifier, the input signal is a differential input signal, the output signal is a differential output signal, and the current source includes a differential current source.

7. The device of claim 6, wherein the modulator includes a first modulator that modulates a first component of the differential output signal at the modulation frequency and a second modulator that modulates a second component of the differential output signal at the modulation frequency, and wherein the feedback path includes a first feedback path branch that couples the first component of the differential output signal to the first input of the differential amplifier and a second feedback path branch that couples the second component of the differential output signal to the second input of the differential amplifier.

8. The device of claim 1, wherein the load includes a biological load, the device further comprising first implantable electrodes coupled to apply the modulated current across a biological load, and second implantable electrodes coupled to sense the input signal produced across the biological load.

9. A medical device comprising:
means for applying a modulated current at a modulation frequency across a load to produce an input signal, wherein the means for applying comprises a voltage source and a switch that modulates a current produced by the voltage source to produce the modulated current;
means for amplifying the input signal to produce an amplified signal; and
means for demodulating the amplified signal at the modulation frequency to produce an output signal indicating an impedance of the load.

10. The device of claim 9, further comprising means for modulating the output signal at the modulation frequency to produce a feedback signal.

11. The device of claim 10, further comprising means for applying the feedback signal to the input signal.

12. The device of claim 11, further comprising an input capacitor that couples the input signal to an input of the means for amplifying, and means for applying the feedback signal to the input signal at a node between the input capacitor and the input of the amplifying means via a feedback capacitor.

13. The device of claim 12, wherein the input capacitor and the feedback capacitor are arranged such that a ratio of the feedback capacitor to the input capacitor sets a gain of the amplifier.

14. The device of claim 11, wherein the amplifying means includes a differential amplifier, the input signal is a differential input signal, and the output signal is a differential output signal.

15. The device of claim 14, wherein the modulating means includes a first modulator that modulates a first component of the differential output signal at the modulation frequency and a second modulator that modulates a second component of the differential output signal at the modulation frequency, and wherein the means for applying the feedback signal includes a first feedback path branch that couples the first component of the differential output signal to the first input of the differential amplifier and a second feedback path branch that couples the second component of the differential output signal to the second input of the differential amplifier.

16. The device of claim 9, wherein the load includes a biological load, the device further comprising first implantable electrodes coupled to apply the modulated current across a biological load, and second implantable electrodes coupled to sense the input signal produced across the biological load.

17. A method for sensing impedance of a load, the method comprising:
switching, with a medical device, a current produced by a voltage source at a modulation frequency to produce a modulated current;
applying, with the medical device, the modulated current at the modulation frequency across a load to produce an input signal;
amplifying, with the medical device, the input signal with an amplifier to produce an amplified signal; and
demodulating, with the medical device, an amplitude of the amplified signal at the modulation frequency to produce an output signal indicating an impedance of the load.

18. The method of claim 17, further comprising modulating an amplitude of the output signal at the modulation frequency to produce a feedback signal.

19. The method of claim 18, further comprising applying the feedback signal to the input signal via a feedback path.

20. The method of claim 19, further comprising coupling the input signal to an input of the amplifier via an input capacitor, wherein applying the a feedback signal to the input signal comprises applying the feedback signal to the input signal at a node between the input capacitor and the input of the amplifier via a feedback capacitor.

21. The method of claim 20, wherein the input capacitor and the feedback capacitor are arranged such that a ratio of the feedback capacitor to the input capacitor sets a gain of the amplifier.

22. The method of claim 19, wherein the amplifier includes a differential amplifier, the input signal is a differential input signal, and the output signal is a differential output signal.

23. The method of claim 22, further comprising modulating a first component of the differential output signal at the modulation frequency and modulating a second component of the differential output signal at the modulation frequency, applying the first component of the differential output signal to the first input of the differential amplifier, and applying the second component of the differential output signal to the second input of the differential amplifier.

24. The method of claim 17, wherein the load includes a biological load, the method further comprising applying the modulated current across the biological load via first implantable electrodes, and sensing the input signal produced across the biological load via second implantable electrodes.

* * * * *